US008598113B2

(12) United States Patent
Nilsson et al.

(10) Patent No.: US 8,598,113 B2
(45) Date of Patent: Dec. 3, 2013

(54) POLYPEPTIDES

(75) Inventors: Fredrik Nilsson, Stockholm (SE); Tove Eriksson, Nacka (SE); Andreas Jonsson, Bromma (SE); Stefan Stahl, Stockholm (SE); Mikaela Friedman, Stockholm (SE)

(73) Assignee: Affibody AB, Solna (SE)

( * ) Notice: Subject to any disclaimer, the term of this patent is extended or adjusted under 35 U.S.C. 154(b) by 0 days.

(21) Appl. No.: 13/549,588

(22) Filed: Jul. 16, 2012

(65) Prior Publication Data

US 2013/0005653 A1    Jan. 3, 2013

Related U.S. Application Data

(62) Division of application No. 12/085,576, filed on Aug. 20, 2008, now Pat. No. 8,247,375.

(30) Foreign Application Priority Data

Dec. 5, 2005   (GB) .................................. 0524788.7
Dec. 5, 2006   (EP) .................. PCT/EP2006/011669

(51) Int. Cl.
*A61K 38/22*    (2006.01)
*C07K 14/485*   (2006.01)

(52) U.S. Cl.
USPC .............................. 514/1.1; 514/7.6; 514/9.6

(58) Field of Classification Search
None
See application file for complete search history.

(56) References Cited

FOREIGN PATENT DOCUMENTS

| SE | WO95/19374 A1 | 7/1995 |
| SE | WO00/63243 A1 | 10/2000 |
| SE | WO2005/000883 A1 | 1/2005 |
| SE | WO2005/003156 A1 | 1/2005 |
| SE | WO2005/075507 A1 | 8/2005 |

OTHER PUBLICATIONS

Ciardiello et al. "EGFR Antagonists in Cancer Treatment." The New England J. of Med. vol. 358, No. 11, pp. 1160-1174. 2008.*
Vivanco et al. "Differential Sensitivity of Glioma-versus Lung Cancer—Specific EGFR Mutations to EGFR Kinase Inhibitors." Cancer Discovery, vol. 2, pp. 458-471. 2012.*
Nord, K. et al. "Binding proteins selected from combinatorial libraries of an alpha-helical bacterial receptor domain", Nature Biotechnology, Nature Publishing Group, vol. 15, No. 8, pp. 772-777, XPO02149252 (1997).
Nord, K. et al., "A combinatorial library of an alpha-helical bacterial receptor domain", Protein Engineering, Oxford University Press, vol. 8, No. 6, pp. 601-608, XP000615264 (1995).
Wikman, M. et al., "Selection and characterization of HER2/neu-binding affibody ligands", Protein Engineering, Design and Selection, Oxford Journal, London, GB, vol. 17, No. 5, pp. 455-462, XP002982293 (2004).
Friedman, M. et al., "Directed Evolution to Low Nanomolar Affinity of a Tumor-Targeting Epidermal Growth Factor Receptor-Binding Affibody Molecule", Journal of Molecular Biology, vol. 376, pp. 1388-1402 (2008).

\* cited by examiner

*Primary Examiner* — Cecilia J Tsang
*Assistant Examiner* — Sergio Coffa
(74) *Attorney, Agent, or Firm* — Cantor Colburn LLP

(57) ABSTRACT

This invention relates to polypeptides which bind to EGFR family receptors and to applications of those polypeptides in medicine, veterinary medicine, diagnosis diagnostics and imaging.

34 Claims, 28 Drawing Sheets

| Polypeptide | Amino acid sequence | SEQ ID NO: |
|---|---|---|
| EBM00940 | EWSAAASEISGLPNLNKLQAFAFIVSLVD | 1 |
| EBM00942 | EMLIAMEEIGSLPNLNWGQEQAFLLSLMD | 2 |
| EBM00947 | ETGAAMREINDLPNLNNLQFFAFIVSLVD | 3 |
| EBM00948 | EFYAAITEINRLPNLNGWQMVAFISSLSD | 4 |
| EBM00949 | EHAKAMWEIGNLPNLNLVQLAAFIFSLRD | 5 |
| EBM00951 | ESLAASVEISHLPNLNGSQCKAFIRSLMD | 6 |
| EBM00955 | ELEKAYNEIRNLPNLNGWQMTAFIASLVD | 7 |
| EBM00956 | EAAPAWTEIVRLPNLNRGQKQAFIVSLHD | 8 |
| EBM00957 | ELWIATSEIVELPNLNMHQGVAFIRSLLD | 9 |
| EBM01239 | EVQNAVAEIVKLPNLNGWQSTAFIASLSD | 10 |
| EBM01831 | EYEEAWNEIRNLPNLNGWQMTAFIASLVD | 11 |
| EBM01832 | EIERAMQEIRNLPNLNGWQMTAFIASLVD | 12 |
| EBM01833 | EVETAWMEIRNLPNLNGWQMTAFIASLVD | 13 |
| EBM01834 | ETETAIQEIRSLPNLNGWQMTAFIASLFD | 14 |
| EBM01835 | ETDRAVEEIRNLPNLNGWQMTAFIASLFD | 15 |
| EBM01836 | EMWRAWEEIRNLPNLNGWQMTAFIASLVD | 16 |
| EBM01837 | ESQDAWEEIRSLPNLNGWQMTAFIASLVD | 17 |
| EBM01838 | EREEAIKEIHNLPNLNGWQMTAFIASLFD | 18 |
| EBM01839 | ESWEAWHEIRNLPNLNGWQMTAFIASLVD | 19 |
| EBM01840 | ELYDAMIEINHLPNLNGWQMTAFIASLVD | 20 |
| EBM01841 | ETDKAVQEIHNLPNLNGWQMTAFIASLFD | 21 |
| EBM01842 | EQVRAWEEIRNLPNLNGWQMTAFIASLFD | 22 |
| EBM01843 | ELWGAWEEIHNLPNLNGWQMTAFIASLVD | 23 |
| EBM01844 | ERDAAWEEIRHLPNLNGWQMTAFIASLVD | 24 |
| EBM01845 | EVFPALQEIRNLPNLNGWQMTAFIASLFD | 25 |
| EBM01846 | EVEMATQEIRNLPNLNGWQMTAFIASLFD | 26 |
| EBM01847 | ELYQAMDEIRSLPNLNGWQMTAFIASLVD | 27 |
| EBM01848 | EATEAWDEIRNLPNLNGWQMTAFIASLFD | 28 |
| EBM01849 | EVEWALQEIRNLPNLNGWQMTAFIASLFD | 29 |
| EBM01850 | EVSPALEEIRSLPNLNGWQMTAFIASLFD | 30 |
| EBM01851 | ERERAIEEIHNLPNLNGWQMTAFIASLED | 31 |
| EBM01852 | EAESAWNEIHNLPNLNGWQMTAFIASLVD | 32 |

FIGURE 1A

| Polypeptide | Amino acid sequence | SEQ ID NO: |
|---|---|---|
| EBM01853 | EFWASDEIRNLPNLNGWQMTAFIASLAD | 33 |
| EBM01854 | EMWSAWEEIHNLPNLNGWQMTAFIASLVD | 34 |
| EBM01855 | EHWNAMHEIRSLPNLNGWQMTAFIASLFD | 35 |
| EBM01856 | EVEKAWSEIRSLPNLNGWQMTAFIASLVD | 36 |
| EBM01857 | EREKAWMEIRNLPNLNGWQMTAFIASLVD | 37 |
| EBM01858 | EMWSAWSEIHNLPNLNGWQMTAFIASLVD | 38 |
| EBM01859 | EMWSAWAEIRNLPNLNGWQMTAFIASLVD | 39 |
| EBM01860 | ERSLAIREIHNLPNLNGWQMTAFIASLFD | 40 |
| EBM01861 | ERDTAISEIRNLPNLNGWQMTAFIASLFD | 41 |
| EBM01862 | EMWAAWGEIHSLPNLNGWQMTAFIASLVD | 42 |
| EBM01863 | ERDTAIYEIRNLPNLNGWQMTAFIASLFD | 43 |
| EBM01864 | EPWLAWAEIRNLPNLNGWQMTAFIASLVD | 44 |
| EBM01865 | EMWDAWEEIHNLPNLNGWQMTAFIASLFD | 45 |
| EBM01866 | EDMEAVDEIRNLPNLNGWQMTAFIASLFD | 46 |
| EBM01867 | EAEHAWEEIRNLPNLNGWQMTAFIASLVD | 47 |
| EBM01868 | ELWIAWDEIRNLPNLNGWQMTAFIASLVD | 48 |
| EBM01869 | EMWNAWSEIRNLPNLNGWQMTAFIASLVD | 49 |
| EBM01870 | EINSAIGEIHNLPNLNGWQMTAFIASLFD | 50 |
| EBM01871 | EMWRAWEEIHNLPNLNGWQMTAFIASLFD | 51 |
| EBM01872 | ESWKAWEEIRNLPNLNGWQMTAFIASLVD | 52 |
| EBM01873 | ETEWAIQEIRNLPNLNGWQMTAFIASLFD | 53 |
| EBM01874 | EAEFAWTEIRNLPNLNGWQMTAFIASLVD | 54 |
| EBM01875 | ELLVAMLEINHLPNLNGWQMTAFIASLVD | 55 |
| EBM01876 | ERDFAIDEIHSLPNLNGWQMTAFIASLFD | 56 |
| EBM01877 | EMWIAWEEIRNLPNLNGWQMTAFIASLVD | 57 |
| EBM01878 | ESNSAWQEIRNLPNLNGWQMTAFIASLVD | 58 |
| EBM01879 | EVWTAWEEIHNLPNLNGWQMTAFIASLVD | 59 |
| EBM01880 | EPWMAWDEIRSLPNLNGWQMTAFIASLVD | 60 |
| EBM01881 | ERDGAIQEIRNLPNLNGWQMTAFIASLFD | 61 |
| EBM01882 | EKWTAWEEIRSLPNLNGWQMTAFIASLVD | 62 |
| EBM01883 | EMWHAWDEIRHLPNLNGWQMTAFIASLVD | 63 |
| EBM01884 | EVDQAVAEIRNLPNLNGWQMTAFIASLFD | 64 |

FIGURE 1B

| Polypeptide | Amino acid sequence | SEQ ID NO: |
|---|---|---|
| EBM01885 | ERYWAIEEIRNLPNLNGWQMTAFIASLFD | 65 |
| EBM01886 | EREEAISEIHSLPNLNGWQMTAFIASLFD | 66 |
| EBM01887 | EMEWAWQEIRNLPNLNGWQMTAFIASLVD | 67 |
| EBM01888 | EVEPAIREIHNLPNLNGWQMTAFIASLFD | 68 |
| EBM01889 | EQDEAVKEIRNLPNLNGWQMTAFIASLFD | 69 |
| EBM01890 | EADSAWTEIRNLPNLNGWQMTAFIASLVD | 70 |
| EBM01891 | ETDYAIGEIHSLPNLNGWQMTAFIASLFD | 71 |
| EBM01892 | EADKAVQEIRNLPNLNGWQMTAFIASLFD | 72 |
| EBM01893 | ETDKAVQEIRNLPNLNGWQMTAFIASLFD | 73 |
| EBM01894 | ELWAAWSEIRNLPNLNGWQMTAFIASLVD | 74 |
| EBM01895 | EAWAAWSEIRNLPNLNGWQMTAFIASLVD | 75 |
| EBM01896 | EVDRAVVEIRSLPNLNGWQMTAFIASLFD | 76 |
| EBM01897 | EAESAIEEIHNLPNLNGWQMTAFIASLFD | 77 |
| EBM01898 | ELGGAVNEIRNLPNLNGWQMTAFIASLFD | 78 |
| EBM01899 | EVDTAIWEIRNLPNLNGWQMTAFIASLFD | 79 |
| EBM01900 | ELANAFDEIHRLPNLNGWQMTAFIASLFD | 80 |
| EBM01901 | EFRRASDEIRNLPNLNGWQMTAFIASLAD | 81 |
| EBM01902 | EIEKAIREIHNLPNLNGWQMTAFIASLVD | 82 |
| EBM01903 | EMWEAWDEIHNLPNLNGWQMTAFIASLVD | 83 |
| EBM01904 | ESKWAWEEIRNLPNLNGWQMTAFIASLVD | 84 |
| EBM01905 | EMWRAWEEIHNLPNLNGWQMTAFIASLVD | 85 |
| EBM01906 | EIDPALQEIRNLPNLNGWQMTAFIASLFD | 86 |
| EBM01907 | EMWAAWEEIRNLPNLNGWQMTAFIASLVD | 87 |
| EBM01908 | EKYWAVDEIRNLPNLNGWQMTAFIASLFD | 88 |
| EBM01909 | EHWAAWHEIRSLPNLNGWQMTAFIASLVD | 89 |
| EBM01910 | EYQTAWKEIRNLPNLNGWQMTAFIASLFD | 90 |
| EBM01911 | ETDRAIKEIHNLPNLNGWQMTAFIASLFD | 91 |
| EBM01912 | EMWNAWHEIRNLPNLNGWQMTAFIASLVD | 92 |
| EBM01913 | EPWVAWNEIRNLPNLNGWQMTAFIASLVD | 93 |
| EBM01914 | ELIGAYDEIRSLPNLNGWQMTAFIASLAD | 94 |
| EBM01915 | ERDYALWEIRNLPNLNGWQMTAFIASLFD | 95 |
| EBM01916 | ETQDAWDEIRNLPNLNGWQMTAFIASLVD | 96 |

FIGURE 1C

| Polypeptide | Amino acid sequence | SEQ ID NO: |
|---|---|---|
| EBM01917 | EMWEAWGEIHNLPNLNGWQMTAFIASLVD | 97 |
| EBM01918 | EMWSAWHEIRSLPNLNGWQMTAFIASLVD | 98 |
| EBM01919 | ELWQAWGEIRNLPNLNGWQMTAFIASLVD | 99 |
| EBM01920 | EVERAWNEIRNLPNLNGWQMTAFIASLVD | 100 |
| EBM01921 | EMWEAWGEIRSLPNLNGWQMTAFIASLVD | 101 |
| EBM01922 | ERTQAIREIHNLPNLNGWQMTAFIASLFD | 102 |
| EBM01923 | ETEEAWEEIHNLPNLNGWQMTAFIASLVD | 103 |
| EBM01924 | EAETAWSEIRNLPNLNGWQMTAFIASLVD | 104 |
| EBM01925 | EMWCAWNEIRNLPNLNGWQMTAFIASLVD | 105 |
| EBM01926 | ERDYAIEEIHNLPNLNGWQMTAFIASLFD | 106 |
| EBM01927 | EMWSAWDEIHNLPNLNGWQMTAFIASLVD | 107 |
| EBM01928 | EMWTAWHEIHNLPNLNGWQMTAFIASLVD | 108 |
| EBM01929 | ETDRAVREIRNLPNLNGWQMTAFIASLVD | 109 |
| EBM01930 | ETWRAWHEIRSLPNLNGWQMTAFIASLVD | 110 |
| EBM01931 | EMWLAWQEIRNLPNLNGWQMTAFIASLVD | 111 |
| EBM01932 | EVDYAIQEIHNLPNLNGWQMTAFIASLFD | 112 |
| EBM01933 | EMESAWIEIRNLPNLNGWQMTAFIASLVD | 113 |
| EBM01934 | ETEEAWEEIRNLPNLNGWQMTAFIASLVD | 114 |
| EBM01935 | ESEAALQEIRNLPNLNGWQMTAFIASLFD | 115 |
| EBM01936 | EFRKASNEIRSLPNLNGWQMTAFIASLAD | 116 |
| EBM01937 | EVQLAWDEIRSLPNLNGWQMTAFIASLVD | 117 |
| EBM01938 | EADRAWEEIRNLPNLNGWQMTAFIASLVD | 118 |
| EBM01939 | EIKPAIREIHSLPNLNGWQMTAFIASLFD | 119 |
| EBM01940 | ELDQAILEIHNLPNLNGWQMTAFIASLVD | 120 |
| EBM01941 | EPWIAWHEITHNLPNLNGWQMTAFIASLFD | 121 |
| EBM01942 | ERDVAITETHNLPNLNGWQMTAFIASLFD | 122 |
| EBM01943 | EFDKAVSEIRNLPNLNGWQMTAFIASLFD | 123 |
| EBM01944 | EVDVAMQEIRNLPNLNGWQMTAFIASLFD | 124 |
| EBM01945 | ETNAALEEIRNLPNLNGWQMTAFIASLVD | 125 |
| EBM01946 | EAEKAWEEIHNLPNLNGWQMTAFIASLVD | 126 |
| EBM01947 | EPWLAWSEIRNLPNLNGWQMTAFIASLVD | 127 |
| EBM01948 | EGLNAVNEIRNLPNLNGWQMTAFIASLFD | 128 |

FIGURE 1D

| Polypeptide | Amino acid sequence | SEQ ID NO: |
|---|---|---|
| EBM01949 | EWEVAMEEIRNLPNLNGWQMTAFIASLFD | 129 |
| EBM01950 | EVESAWTEIRNLPNLNGWQMTAFIASLVD | 130 |
| EBM01951 | ETDRAWDEIRNLPNLNGWQMTAFIASLVD | 131 |
| EBM02268 | EREQATEEIRNLPNLNGWQMTAFIASLFD | 132 |
| EBM02269 | EMEHAWEEIRSLPNLNGWQMTAFIASLVD | 133 |
| EBM02270 | EHWNALHEIRSLPNLNGGQMTAFIASLFD | 134 |
| EBM02271 | EYEAAWDEIRNLPNLNGWQMTAFIASLVD | 135 |
| EBM02272 | EGEMALQEIRNLPNLNGWQMTAFIASLFD | 136 |
| EBM02273 | EFRWASDEIRNLPNLNGWQMTAFIASLAD | 137 |
| EBM02274 | EHWNALHEIRSLPNLNGWQMTAFIASLFD | 138 |
| EBM02275 | EIDYAIREIHNLPNLNGWQMTAFIASLFD | 139 |
| EBM02276 | ELLQAMLEINHLPNLNGWQMTAFIASLFD | 140 |
| EBM02277 | EVNPALQEIRSLPNLNGWQMTAFIASLFD | 141 |
| EBM02278 | ELLSAMLEIWHLPNLNGWQMTAFIASLVD | 142 |
| EBM02279 | ERDEAIQEIHSLPNLNGWQMTAFIASLVD | 143 |
| EBM02280 | ETDWAIQEIRSLPNLNGWQMTAFIASLFD | 144 |
| EBM02281 | EMEKAWVEIRNLPNLNGWQMTAFIASIVD | 145 |
| EBM02282 | ELDNAIDEIRNLPNLNGWQMTAFIASLLD | 146 |
| EBM02377 | EMWIAWEEIRDLPNLNGWQMTAFIASLLD | 147 |
| EBM02378 | EMWLAWEEIRNLPNLNGWQLTAFIASLLD | 148 |
| EBM02379 | EMWSAWDEIRALPNLNGWQMTAFISSLLD | 149 |
| EBM02380 | EMWNAWNEIRDLPNLNGWQMTAFIASLLD | 150 |
| EBM02381 | EMWGAWNEIRDLPNLNGWQMTAFISSLLD | 151 |
| EBM02382 | EMWIAWDEIRDLPNLNGWQMTAFIASLLD | 152 |
| EBM02383 | ELWIAWDEIRYLPNLNGWQMTAFIASLLD | 153 |
| EBM02384 | EMWKAWEEIRSLPNLNGWQMTAFIASLLD | 154 |
| EBM02385 | EMWDAWGEIRNLPNLNGWQMTAFIASLLD | 155 |
| EBM02386 | EVWVAWEEIRDLPNLNGWQMTAFIASLVD | 156 |
| EBM02387 | EMWGAWNEIRNLPNLNGWQMTAFIASLVD | 157 |
| EBM02388 | EMWMAWDEIRYLPNLNGWQLTAFISSLLD | 158 |
| EBM02389 | EMWVAWEEIRNLPNLNGWQMTAFIGSLLD | 159 |
| EBM02390 | EMWDAWDEIRYLPNLNGWQFTAFIASLLD | 160 |

FIGURE 1E

| Polypeptide | Amino acid sequence | SEQ ID NO: |
|---|---|---|
| EBM02391 | ELWGAWDEIRYLPNLNGWQMTAFIASLLD | 161 |
| EBM02392 | ESWNAVKEIGELPNLNWGQADAFINSLWD | 162 |
| EBM02393 | ESHEVWQEIRSLPNLNGWQLTAFINSLLD | 163 |
| Z00940 | VDNKFNKEWSAAASEISGLPNLNKLQAFAFIVSLVDDPSQSANLLAEAKKLNDAQAPK | 164 |
| Z00942 | VDNKFNKEMLIAMEEIGSLPNLNWGQEOAFILSLWDDPSQSANLLAEAKKLNDAQAPK | 165 |
| Z00947 | VDNKFNKETGAAMREINDLPNLNLQFFAFIVSLVDDPSQSANLLAEAKKLNDAQAPK | 166 |
| Z00948 | VDNKFNKEFYAAITEINRLPNLNGWMVAFISSLSDDPSQSANLLAEAKKLNDAQAPK | 167 |
| Z00949 | VDNKFNKEHAKAMWEIGNLPNLNLVQLAAFIFSLRDDPSQSANLLAEAKKLNDAQAPK | 168 |
| Z00951 | VDNKFNKESLAASVEISHLPNLNGSQCKAFIRSLMDDPSQSANLLAEAKKLNDAQAPK | 169 |
| Z00955 | VDNKFNKELEKAYNEIRNLPNLNRGQKQAFIVSLHDDPSQSANLLAEAKKLNDAQAPK | 170 |
| Z00956 | VDNKFNKEAAPAWTEIVRLPNLNMHQGVAFIRSLLDDPSQSANLLAEAKKLNDAQAPK | 171 |
| Z00957 | VDNKFNKELWIATSEIVELPNLNHQGVAFIRSLLDDPSQSANLLAEAKKLNDAQAPK | 172 |
| Z01239 | VDNKFNKEVQNAVAEIVKLPNLNGWQSTAFIASLSDDPSQSANLLAEAKKLNDAQAPK | 173 |
| Z01831 | VDNKFNKEYEEAWNEIRNLPNLNGWQMTAFIASLVDDPSQSANLLAEAKKLNDAQAPK | 174 |
| Z01832 | VDNKFNKEIERAMQEIRNLPNLNGWQMTAFIASLVDDPSQSANLLAEAKKLNDAQAPK | 175 |
| Z01833 | VDNKFNKEVETAWMEIRNLPNLNGWQMTAFIASLVDDPSQSANLLAEAKKLNDAQAPK | 176 |
| Z01834 | VDNKFNKETETAIQEIRSLPNLNGWQMTAFIASLFDDPSQSANLLAEAKKLNDAQAPK | 177 |
| Z01835 | VDNKFNKETDRAVEEIRNLPNLNGWQMTAFIASLFDDPSQSANLLAEAKKLNDAQAPK | 178 |
| Z01836 | VDNKFNKEMVRAWEEIRNLPNLNGWQMTAFIASLVDDPSQSANLLAEAKKLNDAQAPK | 179 |
| Z01837 | VDNKFNKESQDAWEEIRSLPNLNGWQMTAFIASLFDDPSQSANLLAEAKKLNDAQAPK | 180 |
| Z01838 | VDNKFNKEREEAIKEIHNLPNLNGWQMTAFIASLFDDPSQSANLLAEAKKLNDAQAPK | 181 |
| Z01839 | VDNKFNKESWEAWHEIRNLPNLNGWQMTAFIASLVDDPSQSANLLAEAKKLNDAQAPK | 182 |
| Z01840 | VDNKFNKELYDAMIEINHLPNLNGWQMTAFIASLFDDPSQSANLLAEAKKLNDAQAPK | 183 |
| Z01841 | VDNKFNKETDKAVQEIHNLPNLNGWQMTAFIASLVDDPSQSANLLAEAKKLNDAQAPK | 184 |
| Z01842 | VDNKFNKEQVRAWEEIRNLPNLNGWQMTAFIASLVDDPSQSANLLAEAKKLNDAQAPK | 185 |
| Z01843 | VDNKFNKELWGAWEEIHNLPNLNGWQMTAFIASLVDDPSQSANLLAEAKKLNDAQAPK | 186 |
| Z01844 | VDNKFNKERDAAWEEIRHLPNLNGWQMTAFIASLVDDPSQSANLLAEAKKLNDAQAPK | 187 |
| Z01845 | VDNKFNKEVFPALQEIRNLPNLNGWQMTAFIASLFDDPSQSANLLAEAKKLNDAQAPK | 188 |
| Z01846 | VDNKFNKEVEMATQEIRNLPNLNGWQMTAFIASLFDDPSQSANLLAEAKKLNDAQAPK | 189 |
| Z01847 | VDNKFNKELYQAMDEIRSLPNLNGWQMTAFIASLVDDPSQSANLLAEAKKLNDAQAPK | 190 |
| Z01848 | VDNKFNKEATEAWDEIRLPNLNGWQMTAFIASLFDDPSQSANLLAEAKKLNDAQAPK | 191 |
| Z01849 | VDNKFNKEVEWALQEIRNLPNLNGWQMTAFIASLFDDPSQSANLLAEAKKLNDAQAPK | 192 |

FIGURE 1F

| Polypeptide | Amino acid sequence | SEQ ID NO: |
|---|---|---|
| Z01850 | VDNKFNKEVSPALEEIRSLPNLNGWQMTAFIASLFDPSQSANLLAEAKKLNDAQAPK | 193 |
| Z01851 | VDNKFNKERERAIEEIHNLPNLNGWQMTAFIASLFDPSQSANLLAEAKKLNDAQAPK | 194 |
| Z01852 | VDNKFNKEAESAWNEIHNLPNLNGWQMTAFIASLVDDPSQSANLLAEAKKLNDAQAPK | 195 |
| Z01853 | VDNKFNKEFWASDEIRNLPNLNGWQMTAFIASLADDPSQSANLLAEAKKLNDAQAPK | 196 |
| Z01854 | VDNKFNKEMWSAWEEIHNLPNLNGWQMTAFIASLVDDPSQSANLLAEAKKLNDAQAPK | 197 |
| Z01855 | VDNKFNKEHWNAMHEIRSLPNLNGWQMTAFIASLFDPSQSANLLAEAKKLNDAQAPK | 198 |
| Z01856 | VDNKFNKEVEKAWSEIRSLPNLNGWQMTAFIASLVDDPSQSANLLAEAKKLNDAQAPK | 199 |
| Z01857 | VDNKFNKEREKAWMEIRNLPNLNGWQMTAFIASLFDPSQSANLLAEAKKLNDAQAPK | 200 |
| Z01858 | VDNKFNKEMWSAWSEIHNLPNLNGWQMTAFIASLVDDPSQSANLLAEAKKLNDAQAPK | 201 |
| Z01859 | VDNKFNKEMWSAWAEIRNLPNLNGWQMTAFIASLFDPSQSANLLAEAKKLNDAQAPK | 202 |
| Z01860 | VDNKFNKERSLAIREIHNLPNLNGWQMTAFIASLFDPSQSANLLAEAKKLNDAQAPK | 203 |
| Z01861 | VDNKFNKERDTAISEIRNLPNLNGWQMTAFIASLVDDPSQSANLLAEAKKLNDAQAPK | 204 |
| Z01862 | VDNKFNKEWAAWGEIHSLPNLNGWQMTAFIASLFDPSQSANLLAEAKKLNDAQAPK | 205 |
| Z01863 | VDNKFNKERDTAIYEIRNLPNLNGWQMTAFIASLFDPSQSANLLAEAKKLNDAQAPK | 206 |
| Z01864 | VDNKFNKEPWLAWAEIRNLPNLNGWQMTAFIASLFDPSQSANLLAEAKKLNDAQAPK | 207 |
| Z01865 | VDNKFNKEMWDAWEEIHNLPNLNGWQMTAFIASLVDDPSQSANLLAEAKKLNDAQAPK | 208 |
| Z01866 | VDNKFNKEDMEAVDEIRNLPNLNGWQMTAFIASLFDPSQSANLLAEAKKLNDAQAPK | 209 |
| Z01867 | VDNKFNKEAEHAWEEIRNLPNLNGWQMTAFIASLVDDPSQSANLLAEAKKLNDAQAPK | 210 |
| Z01868 | VDNKFNKELWIAWDEIRNLPNLNGWQMTAFIASLVDDPSQSANLLAEAKKLNDAQAPK | 211 |
| Z01869 | VDNKFNKEMWNAWSEIRNLPNLNGWQMTAFIASLFDPSQSANLLAEAKKLNDAQAPK | 212 |
| Z01870 | VDNKFNKEINSAIGEIHNLPNLNGWQMTAFIASLFDPSQSANLLAEAKKLNDAQAPK | 213 |
| Z01871 | VDNKFNKEMGRAWEEIHNLPNLNGWQMTAFIASLVDDPSQSANLLAEAKKLNDAQAPK | 214 |
| Z01872 | VDNKFNKESWKAWEEIRNLPNLNGWQMTAFIASLVDDPSQSANLLAEAKKLNDAQAPK | 215 |
| Z01873 | VDNKFNKETEWAIQEIRNLPNLNGWQMTAFIASLVDDPSQSANLLAEAKKLNDAQAPK | 216 |
| Z01874 | VDNKFNKEAEFAWTEIRNLPNLNGWQMTAFIASLFDPSQSANLLAEAKKLNDAQAPK | 217 |
| Z01875 | VDNKFNKELLVAMLEINHLPNLNGWQMTAFIASLVDDPSQSANLLAEAKKLNDAQAPK | 218 |
| Z01876 | VDNKFNKERDFAIDEIHSLPNLNGWQCMTAFIASLFDPSQSANLLAEAKKLNDAQAPK | 219 |
| Z01877 | VDNKFNKEMWIAWEEIRNLPNLNGWQMTAFIASLVDDPSQSANLLAEAKKLNDAQAPK | 220 |
| Z01878 | VDNKFNKESNSAWQEIRNLPNLNGWQMTAFIASLVDDPSQSANLLAEAKKLNDAQAPK | 221 |
| Z01879 | VDNKFNKEVWIAWEEIHNLPNLNGWQMTAFIASLVDDPSQSANLLAEAKKLNDAQAPK | 222 |
| Z01880 | VDNKFNKEPWMAWDEIRSLPNLNGWQMTAFIASLVDDPSQSANLLAEAKKLNDAQAPK | 223 |
| Z01881 | VDNKFNKERDGAIQEIRNLPNLNGWQMTAFIASLFDPSQSANLLAEAKKLNDAQAPK | 224 |

FIGURE 1G

| Polypeptide | Amino acid sequence | SEQ ID NO: |
|---|---|---|
| Z01882 | VDNKFNKEKWTAWEEIRSLPNLNGWQMTAFIASLVDDPSQSANLLAEAKKLNDAQAPK | 225 |
| Z01883 | VDNKFNKEMWHAWDEIRHLPNLNGWQMTAFIASLVDDPSQSANLLAEAKKLNDAQAPK | 226 |
| Z01884 | VDNKFNKEVDQAVAEIRNLPNLNGWQMTAFIASLFDDPSQSANLLAEAKKLNDAQAPK | 227 |
| Z01885 | VDNKFNKERYWAIEEIRNLPNLNGWQMTAFIASLFDDPSQSANLLAEAKKLNDAQAPK | 228 |
| Z01886 | VDNKFNKEREEAISEIHSLPNLNGWQMTAFIASLFDDPSQSANLLAEAKKLNDAQAPK | 229 |
| Z01887 | VDNKFNKEMEWAWQEIRNLPNLNGWQMTAFIASLFDDPSQSANLLAEAKKLNDAQAPK | 230 |
| Z01888 | VDNKFNKEVEPAIREIHNLPNLNGWQMTAFIASLFDDPSQSANLLAEAKKLNDAQAPK | 231 |
| Z01889 | VDNKFNKEQDEAVKEIRNLPNLNGWQMTAFIASLFDDPSQSANLLAEAKKLNDAQAPK | 232 |
| Z01890 | VDNKFNKEADSAWTEIRNLPNLNGWQMTAFIASLVDDPSQSANLLAEAKKLNDAQAPK | 233 |
| Z01891 | VDNKFNKETDYAIGETHSLPNLNGWQMTAFIASLFDDPSQSANLLAEAKKLNDAQAPK | 234 |
| Z01892 | VDNKFNKEADKAVQEIRNLPNLNGWQMTAFIASLFDDPSQSANLLAEAKKLNDAQAPK | 235 |
| Z01893 | VDNKFNKETDKAVQEIRNLPNLNGWQMTAFIASLFDDPSQSANLLAEAKKLNDAQAPK | 236 |
| Z01894 | VDNKFNKELWAAWSEIRNLPNLNGWQMTAFIASLFDDPSQSANLLAEAKKLNDAQAPK | 237 |
| Z01895 | VDNKFNKEAWAAWSEIRNLPNLNGWQMTAFIASLFDDPSQSANLLAEAKKLNDAQAPK | 238 |
| Z01896 | VDNKFNKEVDRAVVEIRSLPNLNGWQMTAFIASLFDDPSQSANLLAEAKKLNDAQAPK | 239 |
| Z01897 | VDNKFNKEAESAIEEIHNLPNLNGWQMTAFIASLFDDPSQSANLLAEAKKLNDAQAPK | 240 |
| Z01898 | VDNKFNKELGGAVNEIRNLPNLNGWQMTAFIASLFDDPSQSANLLAEAKKLNDAQAPK | 241 |
| Z01899 | VDNKFNKEVDTAIWEIRNLPNLNGWQMTAFIASLFDDPSQSANLLAEAKKLNDAQAPK | 242 |
| Z01900 | VDNKFNKELANAFDEIHRLPNLNGWQMTAFIASLFDDPSQSANLLAEAKKLNDAQAPK | 243 |
| Z01901 | VDNKFNKEFRRASDEIRNLPNLNGWQMTAFIASLADDPSQSANLLAEAKKLNDAQAPK | 244 |
| Z01902 | VDNKFNKEIEKAIREIHNLPNLNGWQMTAFIASLFDDPSQSANLLAEAKKLNDAQAPK | 245 |
| Z01903 | VDNKFNKEMWEAWDEIHNLPNLNGWQMTAFIASLFDDPSQSANLLAEAKKLNDAQAPK | 246 |
| Z01904 | VDNKFNKESKWAWEEIRNLPNLNGWQMTAFIASLFDDPSQSANLLAEAKKLNDAQAPK | 247 |
| Z01905 | VDNKFNKEMWRAWEEIHNLPNLNGWQMTAFIASLFDDPSQSANLLAEAKKLNDAQAPK | 248 |
| Z01906 | VDNKFNKEIDPALQEIRNLPNLNGWQMTAFIASLFDDPSQSANLLAEAKKLNDAQAPK | 249 |
| Z01907 | VDNKFNKEMWAAWEEIRNLPNLNGWQMTAFIASLFDDPSQSANLLAEAKKLNDAQAPK | 250 |
| Z01908 | VDNKFNKEKYWAVDEIRNLPNLNGWQMTAFIASLFDDPSQSANLLAEAKKLNDAQAPK | 251 |
| Z01909 | VDNKFNKEHWAAWHEIRSLPNLNGWQMTAFIASLVDDPSQSANLLAEAKKLNDAQAPK | 252 |
| Z01910 | VDNKFNKEYQTAWKEIRNLPNLNGWQMTAFIASLFDDPSQSANLLAEAKKLNDAQAPK | 253 |
| Z01911 | VDNKFNKETDRAIKEIHNLPNLNGWQMTAFIASLFDDPSQSANLLAEAKKLNDAQAPK | 254 |
| Z01912 | VDNKFNKEMWNAWHEIRNLPNLNGWQMTAFIASLFDDPSQSANLLAEAKKLNDAQAPK | 255 |
| Z01913 | VDNKFNKEPWVAWNEIRNLPNLNGWQMTAFIASLFDDPSQSANLLAEAKKLNDAQAPK | 256 |

FIGURE 1H

| Polypeptide | Amino acid sequence | SEQ ID NO: |
|---|---|---|
| Z01914 | VDNKFNKEL-GAYDEIRSLPNLNGWQMTAFIASLADDPSQSANLLAEAKKLNDAQAPK | 257 |
| Z01915 | VDNKFNKERDYALWEIRNLPNLNGWQMTAFIASLFDDPSQSANLLAEAKKLNDAQAPK | 258 |
| Z01916 | VDNKFNKETQDAWDEIRNLPNLNGWQMTAFIASLVDDPSQSANLLAEAKKLNDAQAPK | 259 |
| Z01917 | VDNKFNKEMWEAWGEIHNLPNLNGWQMTAFIASLVDDPSQSANLLAEAKKLNDAQAPK | 260 |
| Z01918 | VDNKFNKEMWSAWHEIRSLPNLNGWQMTAFIASLVDDPSQSANLLAEAKKLNDAQAPK | 261 |
| Z01919 | VDNKFNKELWQAWGEIRNIPNLNGWQMTAFIASLVDDPSQSANLLAEAKKLNDAQAPK | 262 |
| Z01920 | VDNKFNKEVERAWNEIRNLPNLNGWQMTAFIASLVDDPSQSANLLAEAKKLNDAQAPK | 263 |
| Z01921 | VDNKFNKEMWEAWGEIRSLPNLNGWQMTAFIASLFDDPSQSANLLAEAKKLNDAQAPK | 264 |
| Z01922 | VDNKFNKERCQAIREIHNLPNLNGWQMTAFIASLFDDPSQSANLLAEAKKLNDAQAPK | 265 |
| Z01923 | VDNKFNKETEEAWEEIHNLPNLNGWQMTAFIASLVDDPSQSANLLAEAKKLNDAQAPK | 266 |
| Z01924 | VDNKFNKEAETAWSEIRNLPNLNGWQMTAFIASLVDDPSQSANLLAEAKKLNDAQAPK | 267 |
| Z01925 | VDNKFNKEMWCAWNEIRNLPNLNGWQMTAFIASLFDDPSQSANLLAEAKKLNDAQAPK | 268 |
| Z01926 | VDNKFNKERDYAIEEIHNLPNLNGWQMTAFIASLVDDPSQSANLLAEAKKLNDAQAPK | 269 |
| Z01927 | VDNKFNKEMWSAWDEIHNLPNLNGWQMTAFIASLVDDPSQSANLLAEAKKLNDAQAPK | 270 |
| Z01928 | VDNKFNKEMWTAWHEIHNLPNLNGWQMTAFIASLFDDPSQSANLLAEAKKLNDAQAPK | 271 |
| Z01929 | VDNKFNKETDRAVREIRNLPNLNGWQMTAFIASLFDDPSQSANLLAEAKKLNDAQAPK | 272 |
| Z01930 | VDNKFNKETWRAWHEIRNLPNLNGWQMTAFIASLVDDPSQSANLLAEAKKLNDAQAPK | 273 |
| Z01931 | VDNKFNKEMWLAWQEIRNLPNLNGWQMTAFIASLFDDPSQSANLLAEAKKLNDAQAPK | 274 |
| Z01932 | VDNKFNKEVDYAIQEIHNLPNLNGWQMTAFIASLVDDPSQSANLLAEAKKLNDAQAPK | 275 |
| Z01933 | VDNKFNKEMESAWIEIRNLPNLNGWQMTAFIASLFDDPSQSANLLAEAKKLNDAQAPK | 276 |
| Z01934 | VDNKFNKETEEAWEEIRNLPNLNGWQMTAFIASLVDDPSQSANLLAEAKKLNDAQAPK | 277 |
| Z01935 | VDNKFNKESEAALQEIRNLPNLNGWQMTAFIASLVDDPSQSANLLAEAKKLNDAQAPK | 278 |
| Z01936 | VDNKFNKEFRKASNEIRSLPNLNGWQMTAFIASLADDPSQSANLLAEAKKLNDAQAPK | 279 |
| Z01937 | VDNKFNKEVQLAWDEIRSLPNLNGWQMTAFIASLVDDPSQSANLLAEAKKLNDAQAPK | 280 |
| Z01938 | VDNKFNKEADRAWEEIRNLPNLNGWQMTAFIASLVDDPSQSANLLAEAKKLNDAQAPK | 281 |
| Z01939 | VDNKFNKEIKPAIREIHSLPNLNGWQMTAFIASLFDDPSQSANLLAEAKKLNDAQAPK | 282 |
| Z01940 | VDNKFNKELDQAILEIHNLPNLNGWQMTAFIASLFDDPSQSANLLAEAKKLNDAQAPK | 283 |
| Z01941 | VDNKFNKEPIAWHEIRNLPNLNGWQMTAFIASLVDDPSQSANLLAEAKKLNDAQAPK | 284 |
| Z01942 | VDNKFNKERDVAITEIHNLPNLNGWQMTAFIASLVDDPSQSANLLAEAKKLNDAQAPK | 285 |
| Z01943 | VDNKFNKEDKRAVSEIRNLPNLNGWQMTAFIASLFDDPSQSANLLAEAKKLNDAQAPK | 286 |
| Z01944 | VDNKFNKEDVAMQEIRNLPNLNGWQMTAFIASLFDDPSQSANLLAEAKKLNDAQAPK | 287 |
| Z01945 | VDNKFNKETNAALEEIRNLPNLNGWQMTAFIASLFDDPSQSANLLAEAKKLNDAQAPK | 288 |

FIGURE 1I

| Polypeptide | Amino acid sequence | SEQ ID NO: |
|---|---|---|
| Z01946 | VDNKFNKEAEKAWEEIHNLPNLNGWQMTAFIASLVDDPSQSANLLAEAKKLNDAQAPK | 289 |
| Z01947 | VDNKFNKEPWLAWSEIRNLPNLNGWQMTAFIASLVDDPSQSANLLAEAKKLNDAQAPK | 290 |
| Z01948 | VDNKFNKEGLNAVNEIRNLPNLNGWQMTAFIASLFDDPSQSANLLAEAKKLNDAQAPK | 291 |
| Z01949 | VDNKFNKEWEVAWEEIRNLPNLNGWQMTAFIASLFDDPSQSANLLAEAKKLNDAQAPK | 292 |
| Z01950 | VDNKFNKEVESAWTEIRNLPNLNGWQMTAFIASLVDDPSQSANLLAEAKKLNDAQAPK | 293 |
| Z01951 | VDNKFNKETDRAWDEIRNLPNLNGWQMTAFIASLVDDPSQSANLLAEAKKLNDAQAPK | 294 |
| Z02268 | VDNKFNKEREQATEEIRNLPNLNGWQMTAFIASLFDDPSQSANLLAEAKKLNDAQAPK | 295 |
| Z02269 | VDNKFNKEMEHAWEEIRSLPNLNGWQMTAFIASLVDDPSQSANLLAEAKKLNDAQAPK | 296 |
| Z02270 | VDNKFNKEHWNALHEIRSLPNLNGGQMTAFIASLFDDPSQSANLLAEAKKLNDAQAPK | 297 |
| Z02271 | VDNKFNKEYEAAWDEIRNLPNLNGWQMTAFIASLFDDPSQSANLLAEAKKLNDAQAPK | 298 |
| Z02272 | VDNKFNKEGEMALQEIRNLPNLNGWQMTAFIASLFDDPSQSANLLAEAKKLNDAQAPK | 299 |
| Z02273 | VDNKFNKEFRWASDEIRNLPNLNGWQMTAFIASLADDPSQSANLLAEAKKLNDAQAPK | 300 |
| Z02274 | VDNKFNKEHWNALHEIRSLPNLNGWQMTAFIASLFDDPSQSANLLAEAKKLNDAQAPK | 301 |
| Z02275 | VDNKFNKEIDYAIREIHNLPNLNGWQMTAFIASLVDDPSQSANLLAEAKKLNDAQAPK | 302 |
| Z02276 | VDNKFNKELLQAMLEINHLPNLNGWQMTAFIASLFDDPSQSANLLAEAKKLNDAQAPK | 303 |
| Z02277 | VDNKFNKEVNPALQEIRSLPNLNGWQMTAFIASLVDDPSQSANLLAEAKKLNDAQAPK | 304 |
| Z02278 | VDNKFNKELLSAMLETNHLPNLNGWQMTAFIASLVDDPSQSANLLAEAKKLNDAQAPK | 305 |
| Z02279 | VDNKFNKERDEAIQEIHSLPNLNGWQMTAFIASLFDDPSQSANLLAEAKKLNDAQAPK | 306 |
| Z02280 | VDNKFNKETDWAIQEIRSLPNLNGWQMTAFIASLFDDPSQSANLLAEAKKLNDAQAPK | 307 |
| Z02281 | VDNKFNKEMEKAWVEIRNLPNLNGWQMTAFIASLVDDPSQSANLLAEAKKLNDAQAPK | 308 |
| Z02282 | VDNKFNKELDNAIDEIRNLPNLNGWQMTAFIASLFDDPSQSANLLAEAKKLNDAQAPK | 309 |
| Z02377 | VDNKFNKEMVIAWEEIRDLPNLNGWQMTAFIASLLDDPSQSANLLAEAKKLNDAQAPK | 310 |
| Z02378 | VDNKFNKEMVLAWEEIRDLPNLNGWQLTAFIASLLDDPSQSANLLAEAKKLNDAQAPK | 311 |
| Z02379 | VDNKFNKEMVSAWDEIRALPNLNGWQMTAFISSLLDDPSQSANLLAEAKKLNDAQAPK | 312 |
| Z02380 | VDNKFNKEMWNAWNEIRDLPNLNGWQMTAFISSLLDDPSQSANLLAEAKKLNDAQAPK | 313 |
| Z02381 | VDNKFNKEMWGAWNEIRDLPNLNGWQETAFIASLLDDPSQSANLLAEAKKLNDAQAPK | 314 |
| Z02382 | VDNKFNKEMWLAWDEIRYLPNLNGWQMTAFIASLLDDPSQSANLLAEAKKLNDAQAPK | 315 |
| Z02383 | VDNKFNKELWIAWDEIRYLPNLNGWQMTAFIASLLDDPSQSANLLAEAKKLNDAQAPK | 316 |
| Z02384 | VDNKFNKEMWKAWEEIRSLPNLNGWQMTAFIASLLDDPSQSANLLAEAKKLNDAQAPK | 317 |
| Z02385 | VDNKFNKEMWDAWGEIRNLPNLNGWQMTAFIASLLDDPSQSANLLAEAKKLNDAQAPK | 318 |
| Z02386 | VDNKFNKEVYVAWEEIRDLPNLNGWQMTAFIASLLDDPSQSANLLAEAKKLNDAQAPK | 319 |
| Z02387 | VDNKFNKEMWGAWEEIRNLPNLNGWQMTAFIASLVDDPSQSANLLAEAKKLNDAQAPK | 320 |

FIGURE 1J

| Polypeptide | Amino acid sequence | SEQ ID NO: |
|---|---|---|
| Z02388 | VDNKFNKEMMNAWDEIRYLPNLNGWQLTAFISSLLDDPSQSANLLAEAKKLNDAQAPK | 321 |
| Z02389 | VDNKFNKEMRVTAWEEIRNLPNLNGWQMTAFIGSLLDDPSQSANLLAEAKKLNDAQAPK | 322 |
| Z02390 | VDNKFNKEMMDAWDEIRYLPNLNGWQFTAFIASLLDDPSQSANLLAEAKKLNDAQAPK | 323 |
| Z02391 | VDNKFNKELWNGAWDEIRYLPNLNGWQMTAFIASLLDDPSQSANLLAEAKKLNDAQAPK | 324 |
| Z02392 | VDNKFNKESWNAVKEIGELPNLNWGQADAPINSLWDDPSQSANLLAEAKKLNDAQAPK | 325 |
| Z02393 | VDNKFNKESHEVWQEIRSLPNLNGWQLTAFINSLLDDPSQSANLLAEAKKLNDAQAPK | 326 |
| Z00000 | VDNKFNKEQQNAFYEILHLPNLNEEQRNAFIQSLKDDPSQSANLLAEAKKLNDAQAPK | 327 |
| EGFR | MRPSGTAGAALLALLAALCPASRALEEKKVCQGTSNKLTQLGTFEDHFLSLQRMFNNCEVVLGNLEITYVQRNYD LSFLKTIQEVAGYVLIALNTVERIPLENLQIIRGNMYYENSYALAVLSNYDANKTGLKELPMRNLQEILHGAVRF SNNPALCNVESIQWRDIVSSDFLSNMSMDFQNHLGSCQKCDPSCPNGSCWGAGEENCQKLTKIICAQQCSGRCRG KSPSDCCHNQCAAGCTGPRESDCLVCRKFRDEATCKDTCPPLMLYNPTTYQMDVNPEGKYSFGATCVKKCPRNYV VTDHGSCVRACGADSYEMEEDGVRKCKKCEGPCRKVCNGIGIGEFKDSLSINATNIKHFKNCTSISGDLHILPVA FRGDSFTHTPPLDPQELDILKTVKEITGFLLIQAWPENRTDLHAFENLEIIRGRTKQHGQFSLAVVSLNITSLGL RSLKEISDGDVIISGNKNLCYANTINWKKLFGTSGQKTKIISNRGENSCKATGQVCHALCSPEGCWGPEPRDCVS CRNVSRGRECVDKCNLLEGEPREFVENSECIQCHPECLPQAMNITCTGRGPDNCIQCAHYIDGPHCVKTCPAGVM GENNTLVWKYADAGHVCHLCHPNCTYGCTGPGLEGCPTNGPKIPSIATGMVGALLLLLVALGIGLFMRRRHIVR KRTLRRLLQERELVEPLTPSGEAPNQALLRILKETEFKKIKVLGSGAFGTVYKGLWIPEGEKVKIPVAIKELREA TSPKANKEILDEAYVMASVDNPHVCRLLGICLTSTVQLITQLMPFGCLLDYVREHKDNIGSQYLLNWCVQIAKGM NYLEDRRLVHRDLAARNVLVKTPQHVKITDFGLAKLLGAEEKEYHAEGGKVPIKWMALESILHRIYTHQSDVWSY GVTVWELMTFGSKPYDGIPASEISSILEKGERLPQPPICTIDVYMIMVKCWMIDADSRPKFRELIIEFSKMARDP QRYLVIQGDERMHLPSPTDSNEYRALMDEEDMDDVVDADEYLIPQQGFFSSPSTSRTPLLSSLSATSNNSTVACI DRNGLQSCPIKEDSFLQRYSSDPTGALTEDSIDDTFLPVPEYINQSVPKRPAGSVQNPVYHNQPLNPAPSRDPHY QDPHSTAVGNPEYLNTVQPTCVNSTFDSPAHWAQKGSHQISLDNPDYQQDFFPKEAKPNGIFKGSTAENAEYLRV APQSSEFIGA | 328 |
| EGFR ECD | LEEKKVCQGTSNKLTQLGTFEDHFLSLQRMFNNCEVVLGNLEITYVQRNYDLSFLKTIQEVAGYVLIALNTVERI PLENLQIIRGNMYYENSYALAVLSNYDANKTGLKELPMRNLQEILHGAVRFSNNPALCNVESIQWRDIVSSDFLS NMSMDFQNHLGSCQKCDPSCPNGSCWGAGEENCQKLTKIICAQQCSGRCRGKSPSDCCHNQCAAGCTGPRESDCL VCRKFRDEATCKDTCPPLMLYNPTTYQMDVNPEGKYSFGATCVKKCPRNYVVTDHGSCVRACGADSYEMEEDGVR KCKKCEGPCRKVCNGIGIGEFKDSLSINATNIKHFKNCTSISGDLHILPVAFRGDSFTHTPLDPQELDILKTVK EITGFLLIQAWPENRTDLHAFENLEIIRGRTKQHGQFSLAVVSLNITSLGLRSLKEISDGDVIISGNKNLCYANT INWKKLFGTSGQKTKIISNRGENSCKATGQVCHALCSPEGCWGPEPRDCVSCRNVSRGRECVDKCNLLEGEPREF VENSECIQCHPECLPQAMNITCTGRGPDNCIQCAHYIDGPHCVKTCPAGVMGENNTLVWKYADAGHVCHLCHPNC TYGCTGPGLEGCPTNGPKIPS | 329 |

FIGURE 1K

|  | Helix 1 | | | Helix 2 | | Helix 3 | | |
|---|---|---|---|---|---|---|---|---|
| Zwt | VDNKFNK | EQQNAFYEILH | LPNLNE | EQRNAFIQSLKD | DPSQ | SANLLAEAKKLNDA | QAPK | |
| Z_EGFR:940 | ------- | -WSA-AS--SG | -----K | L-AF---V--V- | ---- | -------------- | ---- | 1 |
| Z_EGFR:942 | ------- | -MLI-ME--GS | -----W | G-EQ---L--W- | ---- | -------------- | ---- | 45 |
| Z_EGFR:947 | ------- | -TGA-MR--ND | -----N | L-FF---V--V- | ---- | -------------- | ---- | 1 |
| Z_EGFR:948 | ------- | -FYA-IT--NR | -----G | W-MV---S--S- | ---- | -------------- | ---- | 1 |
| Z_EGFR:949 | ------- | -HAK-MW--GN | -----L | V-LA---F--R- | ---- | -------------- | ---- | 1 |
| Z_EGFR:951 | ------- | -SLA-SV--SH | -----G | S-CK---R--M- | ---- | -------------- | ---- | 1 |
| Z_EGFR:955 | ------- | -LEK-YN--RN | -----G | W-MT---A--V- | ---- | -------------- | ---- | 1 |
| Z_EGFR:956 | ------- | -AAP-WT--VR | -----R | G-KQ---V--H- | ---- | -------------- | ---- | 1 |
| Z_EGFR:957 | ------- | -LWI-TS--VE | -----M | H-GV---R--L- | ---- | -------------- | ---- | 1 |
| Z_EGFR:1239 | ------- | -VQN-VA--VK | -----G | W-ST---A--S- | ---- | -------------- | ---- | 1 |

Basic:
H, R, K

Acidic:
D, E

Non-Polar:
G, I, F, A, L, M, W, P, V

Polar:
C, Q, N, S, Y, T, S

```
                Helix 1                    Helix 2                   Helix 3
         VDNKFNK EQQNAFYEILH LPNLNE EQRNAFIQSLKD DPSQ SANLLAEAKKLNDA QAPK
Zwt                                                                        45
ZEGFR:942        --MLI-ME--GS  ------W G-EQ----L--W  ----                    -1
ZEGFR:948        --FYA-IT--NR  ------G W-MV----S--S  ----                    -1
ZEGFR:955        --LEK-YN--RN  ------G W-MT----A--V  ----                    -1
ZEGFR:1239       --VQN-VA--VK  ------G W-ST----A--S  ----                    -1
```

*Hydrophobic*
Neutral
Hydrophilic

FIGURE 2C

```
                Helix 1                    Helix 2                   Helix 3
         VDNKFNK EQQNAFYEILH LPNLNE EQRNAFIQSLKD DPSQ SANLLAEAKKLNDA QAPK
Zwt                                                                        45
ZEGFR:942        --MLI-Me--GS  ------W G-eQ----L--W  ----                    -1
ZEGFR:948        --FYA-IT--NR  ------G W-MT----A--V  ----                    -1
ZEGFR:955        --LeK-YN--RN  ------G W-MT----A--V  ----                    -1
ZEGFR:1239       --VQN-VA--VK  ------G W-ST----A--S  ----                    -1
```

*Aromatic R groups* (italic)
Nonpolar, aliphatic R groups (bold)
Polar, uncharged, amino acids (underline)
negatively charged r groups (lower case)
Positively charged R groups (double underline)

FIGURE 2D

*Affinity maturation strategy*

| 9 | 10 | 11 | 13 | 14 | 17 | 18 | 24 | 25 | 27 | 28 | 32 | 35 |
|---|----|----|----|----|----|----|----|----|----|----|----|----|
| X | X  | X  | X  | X  | N/R| N/R| G  | W  | M  | T  | A  | S/V|

```
SEQUENCE LISTING

<160> NUMBER OF SEQ ID NOS: 329

<210> SEQ ID NO 1
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 1

Glu Trp Ser Ala Ala Ala Ser Glu Ile Ser Gly Leu Pro Asn Leu Asn
1               5                   10                  15

Lys Leu Gln Ala Phe Ala Phe Ile Val Ser Leu Val Asp
            20                  25

<210> SEQ ID NO 2
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 2

Glu Met Leu Ile Ala Met Glu Glu Ile Gly Ser Leu Pro Asn Leu Asn
1               5                   10                  15

Trp Gly Gln Glu Gln Ala Phe Ile Leu Ser Leu Trp Asp
            20                  25
```

```
<210> SEQ ID NO 3
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 3

Glu Thr Gly Ala Ala Met Arg Glu Ile Asn Asp Leu Pro Asn Leu Asn
1               5                   10                  15

Asn Leu Gln Phe Phe Ala Phe Ile Val Ser Leu Val Asp
            20                  25

<210> SEQ ID NO 4
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 4

Glu Phe Tyr Ala Ala Ile Thr Glu Ile Asn Arg Leu Pro Asn Leu Asn
1               5                   10                  15

Gly Trp Gln Met Val Ala Phe Ile Ser Ser Leu Ser Asp
            20                  25

<210> SEQ ID NO 5
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 5

Glu His Ala Lys Ala Met Trp Glu Ile Gly Asn Leu Pro Asn Leu Asn
1               5                   10                  15

Leu Val Gln Leu Ala Ala Phe Ile Phe

-continued

```
<210> SEQ ID NO 8
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 8

Glu Ala Ala Pro Ala Trp Thr Glu Ile Val Arg Leu Pro Asn Leu Asn
1               5                   10                  15

Arg Gly Gln Lys Gln Ala Phe Ile Val Ser Leu His Asp
            20                  25

<210> SEQ ID NO 9
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 9

Glu Leu Trp Ile Ala Thr Ser Glu Ile Val Glu Leu Pro Asn Leu Asn
1               5                   10                  15

Met His Gln Gly Val Ala Phe Ile Arg Ser Leu Leu Asp
            20                  25

<210> SEQ ID NO 10
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 10

Glu Val Gln Asn Ala Val Ala Glu Ile Val Lys Leu Pro Asn Leu Asn
1               5                   10                  15

Gly Trp Gln Ser Thr Ala Phe Ile Ala Ser Leu Ser Asp
            20                  25

<210> SEQ ID NO 11
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 11

Glu Tyr Glu Glu Ala Trp Asn Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 12
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 12

Glu Ile Glu Arg Ala Met Gln Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 13
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 13

Glu Val Glu Thr Ala Trp Met Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 14
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 14

Glu Thr Glu Thr Ala Ile Gln Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 15
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 15

Glu Thr Asp Arg Ala Val Glu Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 16
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 16

Glu Met Trp Arg Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 17
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 17

Glu Ser Gln Asp Ala Trp Glu Glu Ile Arg Ser Leu Pro Asn Leu Asn
1               5                   10                  15

Gly Trp Gln Met Thr Ala Phe Ile Ala Ser Leu Val Asp
            20                  25
```

```
<210> SEQ ID NO 18
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 18

Glu Arg Glu Glu Ala Ile Lys Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 19
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 19

Glu Ser Trp Glu Ala Trp His Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 20
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 20

Glu Leu Tyr Asp Ala Met Ile Glu Ile Asn His Leu Pro Asn Leu Asn
1               5                   10                  15

Gly Trp Gln Met Thr Ala Phe Ile Ala Ser Leu Val Asp
            20                  25

<210> SEQ ID NO 21
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 21

Glu Thr Asp Lys Ala Val Gln Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 22
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 22

Glu Gln Val Arg Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 23
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 23

Glu Leu Trp Gly Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 24
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 24

Glu Arg Asp Ala Ala Trp Glu Glu Ile Arg His Leu Pro Asn Leu Asn
1               5                   10                  15

Gly Trp Gln Met Thr Ala Phe Ile Ala Ser Leu Val Asp
            20                  25

<210> SEQ ID NO 25
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 25

Glu Val Phe Pro Ala Leu Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 26
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 26

Glu Val Glu Met Ala Thr Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 27
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 27

Glu Leu Tyr Gln Ala Met Asp Glu Ile Arg Ser Leu Pro Asn Leu Asn
1               5                   10                  15

Gly Trp Gln Met Thr Ala Phe Ile Ala Ser Leu Val Asp
            20                  25
```

```
<210> SEQ ID NO 28
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 28

Glu Ala Thr Glu Ala Trp Asp Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 29
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 29

Glu Val Glu Trp Ala Leu Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 30
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 30

Glu Val Ser Pro Ala Leu Gln Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 31
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 31

Glu Arg Glu Arg Ala Ile Glu Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 32
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 32

Glu Ala Glu Ser Ala Trp Asn Glu Ile His Asn Leu Pro Asn Leu Asn
1               5                   10                  15

Gly Trp Gln Met Thr Ala Phe Ile Ala Ser Leu Val Asp
            20                  25
```

```
<210> SEQ ID NO 33
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 33

Glu Phe Trp Trp Ala Ser Asp Glu Ile Arg Asn Leu Pro Asn Leu Asn
1               5                   10                  15

Gly Trp Gln Met Thr Ala Phe Ile Ala Ser Leu Ala Asp
            20                  25

<210> SEQ ID NO 34
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 34

Glu Met Trp Ser Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 35
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 35

Glu His Trp Asn Ala Met His Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 36
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 36

Glu Val Glu Lys Ala Trp Ser Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 37
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 37

Glu Arg Glu Lys Ala Trp Met Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 38
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 38

Glu Met Trp Ser Ala Trp Ser Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 39
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 39

Glu Met Trp Ser Ala Trp Ala Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 40
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 40

Glu Arg Ser Leu Ala Ile Arg Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 41
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 41

Glu Arg Asp Thr Ala Ile Ser Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 42
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 42

Glu Met Trp Ala Ala Trp Gly Glu Ile His Ser Leu Pro Asn Leu Asn
1               5                   10                  15

Gly Trp Gln Met Thr Ala Phe Ile Ala Ser Leu Val Asp
            20                  25
```

```
<210> SEQ ID NO 43
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 43

Glu Arg Asp Thr Ala Ile Tyr Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 44
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 44

Glu Pro Trp Leu Ala Trp Ala Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 45
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 45

Glu Met Trp Asp Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 46
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 46

Glu Asp Met Glu Ala Val Asp Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 47
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 47

Glu Ala Glu His Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25
```

-continued

```
<210> SEQ ID NO 48
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 48

Glu Leu Trp Ile Ala Trp Asp Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 49
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 49

Glu Met Trp Asn Ala Trp Ser Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 50
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 50

Glu Ile Asn Ser Ala Ile Gly Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 51
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 51

Glu Met Trp Arg Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 52
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 52

Glu Ser Trp Lys Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 53
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 53

Glu Thr Glu Trp Ala Ile Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 54
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 54

Glu Ala Glu Phe Ala Trp Thr Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 55
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 55

Glu Leu Leu Val Ala Met Leu Glu Ile Asn His Leu Pro Asn Leu Asn
1               5                   10                  15

Gly Trp Gln Met Thr Ala Phe Ile Ala Ser Leu Val Asp
            20                  25

<210> SEQ ID NO 56
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 56

Glu Arg Asp Phe Ala Ile Asp Glu Ile His Ser Leu Pro Asn Leu Asn
1               5                   10                  15

Gly Trp Gln Met Thr Ala Phe Ile Ala Ser Leu Phe Asp
            20                  25

<210> SEQ ID NO 57
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 57

Glu Met Trp Ile Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 58
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 58

Glu Ser Asn Ser Ala Trp Gln Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 59
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 59

Glu Val Trp Thr Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 60
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 60

Glu Pro Trp Met Ala Trp Asp Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 61
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 61

Glu Arg Asp Gly Ala Ile Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 62
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 62

Glu Lys Trp Thr Ala Trp Glu Glu Ile Arg Ser Leu Pro Asn Leu Asn
1               5                   10                  15

Gly Trp Gln Met Thr Ala Phe Ile Ala Ser Leu Val Asp
            20                  25
```

```
<210> SEQ ID NO 63
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 63

Glu Met Trp His Ala Trp Asp Glu Ile Arg His Leu Pro Asn Leu Asn
1               5                   10                  15

Gly Trp Gln Met Thr Ala Phe Ile Ala Ser Leu Val Asp
            20                  25

<210> SEQ ID NO 64
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 64

Glu Val Asp Gln Ala Val Ala Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 65
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 65

Glu Arg Tyr Trp Ala Ile Glu Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 66
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 66

Glu Arg Glu Glu Ala Ile Ser Glu Ile His Ser Leu Pro Asn Leu Asn
1               5                   10                  15

Gly Trp Gln Met Thr Ala Phe Ile Ala Ser Leu Phe Asp
            20                  25

<210> SEQ ID NO 67
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 67

Glu Met Glu Trp Ala Trp Gln Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 68
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 68

Glu Val Glu Pro Ala Ile Arg Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 69
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 69

Glu Gln Asp Glu Ala Val Lys Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 70
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 70

Glu Ala Asp Ser Ala Trp Thr Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 71
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 71

Glu Thr Asp Tyr Ala Ile Gly Glu Ile His Ser Leu Pro Asn Leu Asn
1               5                   10                  15

Gly Trp Gln Met Thr Ala Phe Ile Ala Ser Leu Phe Asp
            20                  25

<210> SEQ ID NO 72
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 72

Glu Ala Asp Lys Ala Val Gln Glu Ile Arg Asn Leu Pro Asn Leu Asn
1               5                   10                  15

Gly Trp Gln Met Thr Ala Phe Ile Ala Ser Leu Phe Asp
            20                  25
```

```
<210> SEQ ID NO 73
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 73

Glu Thr Asp Lys Ala Val Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 74
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 74

Glu Leu Trp Ala Ala Trp Ser Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 75
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 75

Glu Ala Trp Ala Ala Trp Ser Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 76
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 76

Glu Val Asp Arg Ala Val Val Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 77
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 77

Glu Ala Glu Ser Ala Ile Glu Glu Ile His Asn Leu Pro Asn Leu Asn
1               5                   10                  15

Gly Trp Gln Met Thr Ala Phe Ile Ala Ser Leu Phe Asp
            20                  25
```

```
<210> SEQ ID NO 78
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 78

Glu Leu Gly Gly Ala Val Asn Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 79
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 79

Glu Val Asp Thr Ala Ile Trp Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 80
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 80

Glu Leu Ala Asn Ala Phe Asp Glu Ile His Arg Leu Pro Asn Leu Asn
1               5                   10                  15

Gly Trp Gln Met Thr Ala Phe Ile Ala Ser Leu Val Asp
            20                  25

<210> SEQ ID NO 81
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 81

Glu Phe Arg Arg Ala Ser Asp Glu Ile Arg Asn Leu Pro Asn Leu Asn
1               5                   10                  15

Gly Trp Gln Met Thr Ala Phe Ile Ala Ser Leu Ala Asp
            20                  25

<210> SEQ ID NO 82
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 82

Glu Ile Glu Lys Ala Ile Arg Glu Ile His Asn Leu Pro Asn Leu Asn
1               5                   10                  15

Gly Trp Gln Met Thr Ala Phe Ile Ala Ser Leu Val Asp
            20                  25
```

```
<210> SEQ ID NO 83
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 83

Glu Met Trp Glu Ala Trp Asp Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 84
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 84

Glu Ser Lys Trp Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 85
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 85

Glu Met Trp Arg Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 86
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 86

Glu Ile Asp Pro Ala Leu Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 87
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 87

Glu Met Trp Ala Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 88
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 88

Glu Lys Tyr Trp Ala Val Asp Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 89
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 89

Glu His Trp Ala Ala Trp His Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 90
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 90

Glu Tyr Gln Thr Ala Trp Lys Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 91
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 91

Glu Thr Asp Arg Ala Ile Lys Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 92
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 92

Glu Met Trp Asn Ala Trp His Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 93
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 93

Glu Pro Trp Val Ala Trp Asn Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 94
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 94

Glu Leu Ile Gly Ala Tyr Asp Glu Ile Arg Ser Leu Pro Asn Leu Asn
1               5                   10                  15

Gly Trp Gln Met Thr Ala Phe Ile Ala Ser Leu Ala Asp
            20                  25

<210> SEQ ID NO 95
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 95

Glu Arg Asp Tyr Ala Leu Trp Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 96
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 96

Glu Thr Gln Asp Ala Trp Asp Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 97
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 97

Glu Met Trp Glu Ala Trp Gly Glu Ile His Asn Leu Pro Asn Leu Asn
1               5                   10                  15

Gly Trp Gln Met Thr Ala Phe Ile Ala Ser Leu Val Asp
            20                  25
```

```
<210> SEQ ID NO 98
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 98

Glu Met Trp Ser Ala Trp His Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 99
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 99

Glu Leu Trp Gln Ala Trp Gly Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 100
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 100

Glu Val Glu Arg Ala Trp Asn Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 101
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 101

Glu Met Trp Glu Ala Trp Gly Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 102
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 102

Glu Arg Thr Gln Ala Ile Arg Glu Ile His Asn Leu Pro Asn Leu Asn
1               5                   10                  15

Gly Trp Gln Met Thr Ala Phe Ile Ala Ser Leu Phe Asp
            20                  25
```

```
<210> SEQ ID NO 103
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 103

Glu Thr Glu Glu Ala Trp Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 104
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 104

Glu Ala Glu Thr Ala Trp Ser Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 105
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 105

Glu Met Trp Cys Ala Trp Asn Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 106
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 106

Glu Arg Asp Tyr Ala Ile Glu Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 107
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 107

Glu Met Trp Ser Ala Trp Asp Glu Ile His Asn Leu Pro Asn Leu Asn
1               5                   10                  15

Gly Trp Gln Met Thr Ala Phe Ile Ala Ser Leu Val Asp
            20                  25
```

```
<210> SEQ ID NO 108
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 108

Glu Met Trp Thr Ala Trp His Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 109
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 109

Glu Thr Asp Arg Ala Val Arg Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 110
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 110

Glu Thr Trp Arg Ala Trp His Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 111
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 111

Glu Met Trp Leu Ala Trp Gln Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 112
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 112

Glu Val Asp Tyr Ala Ile Gln Glu Ile His Asn Leu Pro Asn Leu Asn
1               5                   10                  15

Gly Trp Gln Met Thr Ala Phe Ile Ala Ser Leu Phe Asp
            20                  25
```

```
<210> SEQ ID NO 113
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 113

Glu Met Glu Ser Ala Trp Ile Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 114
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 114

Glu Thr Glu Glu Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 115
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 115

Glu Ser Glu Ala Ala Leu Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 116
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 116

Glu Phe Arg Lys Ala Ser Asn Glu Ile Arg Ser Leu Pro Asn Leu Asn
1               5                   10                  15

Gly Trp Gln Met Thr Ala Phe Ile Ala Ser Leu Ala Asp
            20                  25

<210> SEQ ID NO 117
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 117

Glu Val Gln Leu Ala Trp Asp Glu Ile Arg Ser Leu Pro Asn Leu Asn
1               5                   10                  15

Gly Trp Gln Met Thr Ala Phe Ile Ala Ser Leu Val Asp
            20                  25
```

```
<210> SEQ ID NO 118
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 118

Glu Ala Asp Arg Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 119
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 119

Glu Ile Lys Pro Ala Ile Arg Glu Ile His Ser Leu Pro Asn Leu Asn
1               5                   10                  15

Gly Trp Gln Met Thr Ala Phe Ile Ala Ser Leu Phe Asp
            20                  25

<210> SEQ ID NO 120
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 120

Glu Leu Asp Gln Ala Ile Leu Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 121
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 121

Glu Pro Trp Ile Ala Trp His Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 122
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 122

Glu Arg Asp Val Ala Ile Thr Glu Ile His Asn Leu Pro Asn Leu Asn
1               5                   10                  15

Gly Trp Gln Met Thr Ala Phe Ile Ala Ser Leu Phe Asp
            20                  25
```

```
<210> SEQ ID NO 123
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 123

Glu Phe Asp Lys Ala Val Ser Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 124
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 124

Glu Val Asp Val Ala Met Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 125
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 125

Glu Thr Asn Ala Ala Leu Glu Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 126
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 126

Glu Ala Glu Lys Ala Trp Glu Glu Ile His Asn Leu Pro Asn Leu Asn
1               5                   10                  15

Gly Trp Gln Met Thr Ala Phe Ile Ala Ser Leu Val Asp
            20                  25

<210> SEQ ID NO 127
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 127

Glu Pro Trp Leu Ala Trp Ser Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 128
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 128

Glu Gly Leu Asn Ala Val Asn Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 129
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 129

Glu Trp Glu Val Ala Met Glu Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 130
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 130

Glu Val Glu Ser Ala Trp Thr Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 131
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 131

Glu Thr Asp Arg Ala Trp Asp Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 132
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 132

Glu Arg Glu Gln Ala Thr Glu Glu Ile Arg Asn Leu Pro Asn Leu Asn
1               5                   10                  15

Gly Trp Gln Met Thr Ala Phe Ile Ala Ser Leu Phe Asp
            20                  25
```

```
<210> SEQ ID NO 133
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 133

Glu Met Glu His Ala Trp Glu Glu Ile Arg Ser Leu Pro Asn Leu Asn
1               5                   10                  15

Gly Trp Gln Met Thr Ala Phe Ile Ala Ser Leu Val Asp
            20                  25

<210> SEQ ID NO 134
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 134

Glu His Trp Asn Ala Leu His Glu Ile Arg Ser Leu Pro Asn Leu Asn
1               5                   10                  15

Gly Gly Gln Met Thr Ala Phe Ile Ala Ser Leu Phe Asp
            20                  25

<210> SEQ ID NO 135
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 135

Glu Tyr Glu Ala Ala Trp Asp Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 136
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 136

Glu Gly Glu Met Ala Leu Gln Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 137
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 137

Glu Phe Arg Trp Ala Ser Asp Glu Ile Arg Asn Leu Pro Asn Leu Asn
1               5                   10                  15

Gly Trp Gln Met Thr Ala Phe Ile Ala Ser Leu Ala Asp
            20                  25
```

```
<210> SEQ ID NO 138
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 138

Glu His Trp Asn Ala Leu His Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 139
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 139

Glu Ile Asp Tyr Ala Ile Arg Glu Ile His Asn Leu Pro Asn Leu Asn
1               5                   10                  15

Gly Trp Gln Met Thr Ala Phe Ile Ala Ser Leu Phe Asp
            20                  25

<210> SEQ ID NO 140
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 140

Glu Leu Leu Gln Ala Met Leu Glu Ile Asn His Leu Pro Asn Leu Asn
1               5                   10                  15

Gly Trp Gln Met Thr Ala Phe Ile Ala Ser Leu Val Asp
            20                  25

<210> SEQ ID NO 141
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 141

Glu Val Asn Pro Ala Leu Gln Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 142
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 142

Glu Leu Leu Ser Ala Met Leu Glu Ile Asn His Leu Pro Asn Leu Asn
1               5                   10                  15

Gly Trp Gln Met Thr Ala Phe Ile Ala Ser Leu Val Asp
            20                  25
```

```
<210> SEQ ID NO 143
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 143

Glu Arg Asp Glu Ala Ile Gln Glu Ile His Ser Leu Pro Asn Leu Asn
1               5                   10                  15

Gly Trp Gln Met Thr Ala Phe Ile Ala Ser Leu Phe Asp
            20                  25

<210> SEQ ID NO 144
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 144

Glu Thr Asp Trp Ala Ile Gln Glu Ile Arg Ser Leu Pro Asn Leu Asn
1               5                   10                  15

Gly Trp Gln Met Thr Ala Phe Ile Ala Ser Leu Phe Asp
            20                  25

<210> SEQ ID NO 145
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 145

Glu Met Glu Lys Ala Trp Val Glu Ile Arg Asn Leu Pro Asn Leu Asn
1               5                   10                  15

Gly Trp Gln Met Thr Ala Phe Ile Ala Ser Leu Val Asp
            20                  25

<210> SEQ ID NO 146
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 146

Glu Leu Asp Asn Ala Ile Asp Glu Ile Arg Asn Leu Pro Asn Leu Asn
1               5                   10                  15

Gly Trp Gln Met Thr Ala Phe Ile Ala Ser Leu Phe Asp
            20                  25

<210> SEQ ID NO 147
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 147

Glu Met Trp Ile Ala Trp Glu Glu Ile Arg Asp Leu Pro Asn Leu Asn
1               5                   10                  15

Gly Trp Gln Met Thr Ala Phe Ile Ala Ser Leu Leu Asp
            20                  25
```

```
<210> SEQ ID NO 148
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 148

Glu Met Trp Leu Ala Trp Glu Glu Ile Arg Asn Leu Pro Asn Leu Asn
1               5                   10                  15

Gly Trp Gln Leu Thr Ala Phe Ile Ala Ser Leu Leu Asp
            20                  25

<210> SEQ ID NO 149
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 149

Glu Met Trp Ser Ala Trp Asp Glu Ile Arg Ala Leu Pro Asn Leu Asn
1               5                   10                  15

Gly Trp Gln Met Thr Ala Phe Ile Ser Ser Leu Leu Asp
            20                  25

<210> SEQ ID NO 150
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 150

Glu Met Trp Asn Ala Trp Asn Glu Ile Arg Asp Leu Pro Asn Leu Asn
1               5                   10                  15

Gly Trp Gln Met Thr Ala Phe Ile Ala Ser Leu Leu Asp
            20                  25

<210> SEQ ID NO 151
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 151

Glu Met Trp Gly Ala Trp Asn Glu Ile Arg Asp Leu Pro Asn Leu Asn
1               5                   10                  15

Gly Trp Gln Met Thr Ala Phe Ile Ser Ser Leu Leu Asp
            20                  25

<210> SEQ ID NO 152
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 152

Glu Met Trp Ile Ala Trp Asp Glu Ile Arg Asp Leu Pro Asn Leu Asn
1               5                   10                  15

Gly Trp Gln Phe Thr Ala Phe Ile Ala Ser Leu Leu Asp
            20                  25
```

```
<210> SEQ ID NO 153
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 153

Glu Leu Trp Ile Ala Trp Asp Glu Ile Arg Tyr Leu Pro Asn Leu Asn
1               5                   10                  15

Gly Trp Gln Met Thr Ala Phe Ile Ala Ser Leu Leu Asp
            20                  25

<210> SEQ ID NO 154
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 154

Glu Met Trp Lys Ala Trp Glu Glu Ile Arg Ser Leu Pro Asn Leu Asn
1               5                   10                  15

Gly Trp Gln Met Thr Ala Phe Ile Ala Ser Leu Leu Asp
            20                  25

<210> SEQ ID NO 155
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 155

Glu Met Trp Asp Ala Trp Gly Glu Ile Arg Asn Leu Pro Asn Leu Asn
1               5                   10                  15

Gly Trp Gln Met Thr Ala Phe Ile Ala Ser Leu Leu Asp
            20                  25

<210> SEQ ID NO 156
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 156

Glu Val Trp Val Ala Trp Glu Glu Ile Arg Asp Leu Pro Asn Leu Asn
1               5                   10                  15

Gly Trp Gln Met Thr Ala Phe Ile Ala Ser Leu Leu Asp
            20                  25

<210> SEQ ID NO 157
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 157

Glu Met Trp Gly Ala Trp Glu Glu Ile Arg Asn Leu Pro Asn Leu Asn
1               5                   10                  15

Gly Trp Gln Met Thr Ala Phe Ile Ala Ser Leu Val Asp
            20                  25
```

```
<210> SEQ ID NO 158
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 158

Glu Met Trp Met Ala Trp Asp Glu Ile Arg Tyr Leu Pro Asn Leu Asn
1               5                   10                  15

Gly Trp Gln Leu Thr Ala Phe Ile Ser Ser Leu Leu Asp
            20                  25

<210> SEQ ID NO 159
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 159

Glu Met Trp Val Ala Trp Glu Glu Ile Arg Asn Leu Pro Asn Leu Asn
1               5                   10                  15

Gly Trp Gln Met Thr Ala Phe Ile Gly Ser Leu Leu Asp
            20                  25

<210> SEQ ID NO 160
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 160

Glu Met Trp Asp Ala Trp Asp Glu Ile Arg Tyr Leu Pro Asn Leu Asn
1               5                   10                  15

Gly Trp Gln Phe Thr Ala Phe Ile Ala Ser Leu Leu Asp
            20                  25

<210> SEQ ID NO 161
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 161

Glu Leu Trp Gly Ala Trp Asp Glu Ile Arg Tyr Leu Pro Asn Leu Asn
1               5                   10                  15

Gly Trp Gln Met Thr Ala Phe Ile Ala Ser Leu Leu Asp
            20                  25

<210> SEQ ID NO 162
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 162

Glu Ser Trp Asn Ala Val Lys Glu Ile Gly Glu Leu Pro Asn Leu Asn
1               5                   10                  15

Trp Gly Gln Ala Asp Ala Phe Ile Asn Ser Leu Trp Asp
            20                  25
```

-continued

```
<210> SEQ ID NO 163
<211> LENGTH: 29
<212> TYPE: PRT
<213> ORGANISM: Artificial sequence
<220> FEATURE:
<223> OTHER INFORMATION: Engineered EGFR binding polypeptide

<400> SEQUENCE: 163

Glu Ser His Glu Val Trp Gln Glu Ile Arg Ser Leu Pro Asn Leu Asn
1               5                   10                  15

Gly Trp Gln Leu Thr Ala Phe Ile Asn Ser Leu Leu Asp
            20                  25

<210> SEQ ID NO 164
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 164

Val Asp Asn Lys Phe Asn Lys Glu Trp Ser Ala Ala Ala Ser Glu Ile
1               5                   10                  15

Ser Gly Leu Pro Asn Leu Asn Lys Leu Gln Ala Phe Ala Phe Ile Val
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 165
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 165

Val Asp Asn Lys Phe Asn Lys Glu Met Leu Ile Ala Met Glu Glu Ile
1               5                   10                  15

Gly Ser Leu Pro Asn Leu Asn Trp Gly Gln Glu Gln Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 166
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 166

Val Asp Asn Lys Phe Asn Lys Glu Thr Gly Ala Ala Met Arg Glu Ile
1               5                   10                  15

Asn Asp Leu Pro Asn Leu Asn Asn Leu Gln Phe Phe Ala Phe Ile Val
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 167
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 167

Val Asp Asn Lys Phe Asn Lys Glu Phe Tyr Ala Ala Ile Thr Glu Ile
1               5                   10                  15

Asn Arg Leu Pro Asn Leu Asn Gly Trp Gln Met Val Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 168
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 168

Val Asp Asn Lys Phe Asn Lys Glu His Ala Lys Ala Met Trp Glu Ile
1               5                   10                  15

Gly Asn Leu Pro Asn Leu Asn Leu Val Gln Leu Ala Ala Phe Ile Phe
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 169
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 169

Val Asp Asn Lys Phe Asn Lys Glu Ser Leu Ala Ala Ser Val Glu Ile
1               5                   10                  15

Ser His Leu Pro Asn Leu Asn Gly Ser Gln Cys Lys Ala Phe Ile Arg
            20                  25                  30

Ser Leu Met Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 170
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 170

Val Asp Asn Lys Phe Asn Lys Glu Leu Glu Lys Ala Tyr Asn Glu Ile
1               5                   10                  15
```

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 171
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 171

Val Asp Asn Lys Phe Asn Lys Glu Ala Ala Pro Ala Trp Thr Glu Ile
1               5                   10                  15

Val Arg Leu Pro Asn Leu Asn Arg Gly Gln Lys Gln Ala Phe Ile Val
            20                  25                  30

Ser Leu His Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 172
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 172

Val Asp Asn Lys Phe Asn Lys Glu Leu Trp Ile Ala Thr Ser Glu Ile
1               5                   10                  15

Val Glu Leu Pro Asn Leu Asn Met His Gln Gly Val Ala Phe Ile Arg
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 173
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 173

Val Asp Asn Lys Phe Asn Lys Glu Val Gln Asn Ala Val Ala Glu Ile
1               5                   10                  15

Val Lys Leu Pro Asn Leu Asn Gly Trp Gln Ser Thr Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 174
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 174

Val Asp Asn Lys Phe Asn Lys Glu Tyr Glu Glu Ala Trp Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 175
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 175

Val Asp Asn Lys Phe Asn Lys Glu Ile Glu Arg Ala Met Gln Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 176
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 176

Val Asp Asn Lys Phe Asn Lys Glu Val Glu Thr Ala Trp Met Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 177
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 177

Val Asp Asn Lys Phe Asn Lys Glu Thr Glu Thr Ala Ile Gln Glu Ile
1               5                   10                  15

Arg Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

```
Lys Lys Leu Asn Asp Ala Gln Ala Pro Lys
    50                  55

<210> SEQ ID NO 178
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 178

Val Asp Asn Lys Phe Asn Lys Glu Thr Asp Arg Ala Val Glu Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 179
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 179

Val Asp Asn Lys Phe Asn Lys Glu Met Trp Arg Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 180
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 180

Val Asp Asn Lys Phe Asn Lys Glu Ser Gln Asp Ala Trp Glu Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 181
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 181

Val Asp Asn Lys Phe Asn Lys Glu Arg Glu Glu Ala Ile Lys Glu Ile
```

```
                1               5                  10                  15
His Asn Leu Pro Asn Leu Asn Gly Trp Gln Met Thr Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 182
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 182

Val Asp Asn Lys Phe Asn Lys Glu Ser Trp Glu Ala Trp His Glu Ile
1               5                   10                  15

Arg Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 183
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 183

Val Asp Asn Lys Phe Asn Lys Glu Leu Tyr Asp Ala Met Ile Glu Ile
1               5                   10                  15

Asn His Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 184
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 184

Val Asp Asn Lys Phe Asn Lys Glu Thr Asp Lys Ala Val Gln Glu Ile
1               5                   10                  15

His Asn Leu Pro Asn Leu Asn Gly Trp Gln Met Thr Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 185
<211> LENGTH: 58
```

```
<212> TYPE: PRT
<213> ORGANISM: Artificial sequence
<220> FEATURE:
<223> OTHER INFORMATION: Engineered EGFR binding polypeptide

<400> SEQUENCE: 185

Val Asp Asn Lys Phe Asn Lys Glu Gln Val Arg Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 186
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 186

Val Asp Asn Lys Phe Asn Lys Glu Leu Trp Gly Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 187
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 187

Val Asp Asn Lys Phe Asn Lys Glu Arg Asp Ala Ala Trp Glu Glu Ile
1               5                   10                  15

Arg His Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 188
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 188

Val Asp Asn Lys Phe Asn Lys Glu Val Phe Pro Ala Leu Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
```

-continued

```
            35                  40                  45

Lys Lys Leu Asn Asp Ala Gln Ala Pro Lys
    50                  55

<210> SEQ ID NO 189
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 189

Val Asp Asn Lys Phe Asn Lys Glu Val Glu Met Ala Thr Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 190
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 190

Val Asp Asn Lys Phe Asn Lys Glu Leu Tyr Gln Ala Met Asp Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 191
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 191

Val Asp Asn Lys Phe Asn Lys Glu Ala Thr Glu Ala Trp Asp Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 192
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 192
```

Val Asp Asn Lys Phe Asn Lys Glu Val Glu Trp Ala Leu Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 193
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 193

Val Asp Asn Lys Phe Asn Lys Glu Val Ser Pro Ala Leu Glu Glu Ile
1               5                   10                  15

Arg Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 194
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 194

Val Asp Asn Lys Phe Asn Lys Glu Arg Glu Arg Ala Ile Glu Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 195
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 195

Val Asp Asn Lys Phe Asn Lys Glu Ala Glu Ser Ala Trp Asn Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 196
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 196

Val Asp Asn Lys Phe Asn Lys Glu Phe Trp Trp Ala Ser Asp Glu Ile
1               5                   10                  15

Arg Asn Leu Pro Asn Leu Asn Gly Trp Gln Met Thr Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 197
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 197

Val Asp Asn Lys Phe Asn Lys Glu Met Trp Ser Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 198
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 198

Val Asp Asn Lys Phe Asn Lys Glu His Trp Asn Ala Met His Glu Ile
1               5                   10                  15

Arg Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 199
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 199

Val Asp Asn Lys Phe Asn Lys Glu Val Glu Lys Ala Trp Ser Glu Ile
1               5                   10                  15

Arg Ser Leu Pro Asn Leu Asn Gly Trp Gln Met Thr Ala Phe Ile Ala
            20                  25                  30
```

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 200
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 200

Val Asp Asn Lys Phe Asn Lys Glu Arg Glu Lys Ala Trp Met Glu Ile
1               5                   10                  15

Arg Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 201
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 201

Val Asp Asn Lys Phe Asn Lys Glu Met Trp Ser Ala Trp Ser Glu Ile
1               5                   10                  15

His Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 202
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 202

Val Asp Asn Lys Phe Asn Lys Glu Met Trp Ser Ala Trp Ala Glu Ile
1               5                   10                  15

Arg Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 203
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 203

Val Asp Asn Lys Phe Asn Lys Glu Arg Ser Leu Ala Ile Arg Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 204
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 204

Val Asp Asn Lys Phe Asn Lys Glu Arg Asp Thr Ala Ile Ser Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 205
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 205

Val Asp Asn Lys Phe Asn Lys Glu Met Trp Ala Ala Trp Gly Glu Ile
1               5                   10                  15

His Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 206
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 206

Val Asp Asn Lys Phe Asn Lys Glu Arg Asp Thr Ala Ile Tyr Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 207
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 207

Val Asp Asn Lys Phe Asn Lys Glu Pro Trp Leu Ala Trp Ala Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 208
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 208

Val Asp Asn Lys Phe Asn Lys Glu Met Trp Asp Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 209
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 209

Val Asp Asn Lys Phe Asn Lys Glu Asp Met Glu Ala Val Asp Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 210
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 210

Val Asp Asn Lys Phe Asn Lys Glu Ala Glu His Ala Trp Glu Glu Ile
1               5                   10                  15
```

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 211
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 211

Val Asp Asn Lys Phe Asn Lys Glu Leu Trp Ile Ala Trp Asp Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 212
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 212

Val Asp Asn Lys Phe Asn Lys Glu Met Trp Asn Ala Trp Ser Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 213
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 213

Val Asp Asn Lys Phe Asn Lys Glu Ile Asn Ser Ala Ile Gly Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 214
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 214

Val Asp Asn Lys Phe Asn Lys Glu Met Trp Arg Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 215
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 215

Val Asp Asn Lys Phe Asn Lys Glu Ser Trp Lys Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 216
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 216

Val Asp Asn Lys Phe Asn Lys Glu Thr Glu Trp Ala Ile Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 217
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 217

Val Asp Asn Lys Phe Asn Lys Glu Ala Glu Phe Ala Trp Thr Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

<210> SEQ ID NO 218
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 218

Val Asp Asn Lys Phe Asn Lys Glu Leu Leu Val Ala Met Leu Glu Ile
1               5                   10                  15

Asn His Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 219
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 219

Val Asp Asn Lys Phe Asn Lys Glu Arg Asp Phe Ala Ile Asp Glu Ile
1               5                   10                  15

His Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 220
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 220

Val Asp Asn Lys Phe Asn Lys Glu Met Trp Ile Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 221
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 221

Val Asp Asn Lys Phe Asn Lys Glu Ser Asn Ser Ala Trp Gln Glu Ile

```
                1               5                   10                  15
Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55
```

<210> SEQ ID NO 222
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 222

```
Val Asp Asn Lys Phe Asn Lys Glu Val Trp Thr Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55
```

<210> SEQ ID NO 223
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 223

```
Val Asp Asn Lys Phe Asn Lys Glu Pro Trp Met Ala Trp Asp Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55
```

<210> SEQ ID NO 224
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 224

```
Val Asp Asn Lys Phe Asn Lys Glu Arg Asp Gly Ala Ile Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
        50                  55
```

<210> SEQ ID NO 225
<211> LENGTH: 58

```
<212> TYPE: PRT
<213> ORGANISM: Artificial sequence
<220> FEATURE:
<223> OTHER INFORMATION: Engineered EGFR binding polypeptide

<400> SEQUENCE: 225

Val Asp Asn Lys Phe Asn Lys Glu Lys Trp Thr Ala Trp Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 226
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 226

Val Asp Asn Lys Phe Asn Lys Glu Met Trp His Ala Trp Asp Glu Ile
1               5                   10                  15

Arg His Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 227
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 227

Val Asp Asn Lys Phe Asn Lys Glu Val Asp Gln Ala Val Ala Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 228
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 228

Val Asp Asn Lys Phe Asn Lys Glu Arg Tyr Trp Ala Ile Glu Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
```

Lys Lys Leu Asn Asp Ala Gln Ala Pro Lys
    50                  55

<210> SEQ ID NO 229
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 229

Val Asp Asn Lys Phe Asn Lys Glu Arg Glu Glu Ala Ile Ser Glu Ile
1               5                   10                  15

His Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 230
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 230

Val Asp Asn Lys Phe Asn Lys Glu Met Glu Trp Ala Trp Gln Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 231
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 231

Val Asp Asn Lys Phe Asn Lys Glu Val Glu Pro Ala Ile Arg Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 232
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 232

```
Val Asp Asn Lys Phe Asn Lys Glu Gln Asp Glu Ala Val Lys Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55
```

<210> SEQ ID NO 233
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 233

```
Val Asp Asn Lys Phe Asn Lys Glu Ala Asp Ser Ala Trp Thr Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
    50                  55
```

<210> SEQ ID NO 234
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 234

```
Val Asp Asn Lys Phe Asn Lys Glu Thr Asp Tyr Ala Ile Gly Glu Ile
1               5                   10                  15

His Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55
```

<210> SEQ ID NO 235
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 235

```
Val Asp Asn Lys Phe Asn Lys Glu Ala Asp Lys Ala Val Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55
```

-continued

<210> SEQ ID NO 236
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 236

Val Asp Asn Lys Phe Asn Lys Glu Thr Asp Lys Ala Val Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 237
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 237

Val Asp Asn Lys Phe Asn Lys Glu Leu Trp Ala Ala Trp Ser Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 238
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 238

Val Asp Asn Lys Phe Asn Lys Glu Ala Trp Ala Ala Trp Ser Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 239
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 239

Val Asp Asn Lys Phe Asn Lys Glu Val Asp Arg Ala Val Val Glu Ile
1               5                   10                  15

Arg Ser Leu Pro Asn Leu Asn Gly Trp Gln Met Thr Ala Phe Ile Ala
            20                  25                  30

```
Ser Leu Phe Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 240
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 240

Val Asp Asn Lys Phe Asn Lys Glu Ala Glu Ser Ala Ile Glu Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 241
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 241

Val Asp Asn Lys Phe Asn Lys Glu Leu Gly Gly Ala Val Asn Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 242
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 242

Val Asp Asn Lys Phe Asn Lys Glu Val Asp Thr Ala Ile Trp Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 243
<211> LENGTH: 58
<212> TYPE: PRT
<213> ORGANISM: Artificial sequence
<220> FEATURE:
<223> OTHER INFORMATION: Engineered EGFR binding polypeptide
```

-continued

<400> SEQUENCE: 243

Val Asp Asn Lys Phe Asn Lys Glu Leu Ala Asn Ala Phe Asp Glu Ile
1               5                   10                  15

His Arg Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 244
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 244

Val Asp Asn Lys Phe Asn Lys Glu Phe Arg Arg Ala Ser Asp Glu Ile
1               5                   10                  15

Arg Asn Leu Pro Asn Leu Asn Gly Trp Gln Met Thr Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 245
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 245

Val Asp Asn Lys Phe Asn Lys Glu Ile Glu Lys Ala Ile Arg Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 246
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 246

Val Asp Asn Lys Phe Asn Lys Glu Met Trp Glu Ala Trp Asp Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

-continued

<210> SEQ ID NO 247
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 247

Val Asp Asn Lys Phe Asn Lys Glu Ser Lys Trp Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 248
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 248

Val Asp Asn Lys Phe Asn Lys Glu Met Trp Arg Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 249
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 249

Val Asp Asn Lys Phe Asn Lys Glu Ile Asp Pro Ala Leu Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 250
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 250

Val Asp Asn Lys Phe Asn Lys Glu Met Trp Ala Ala Trp Glu Glu Ile
1               5                   10                  15

```
Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 251
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 251

Val Asp Asn Lys Phe Asn Lys Glu Lys Tyr Trp Ala Val Asp Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 252
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 252

Val Asp Asn Lys Phe Asn Lys Glu His Trp Ala Ala Trp His Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 253
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 253

Val Asp Asn Lys Phe Asn Lys Glu Tyr Gln Thr Ala Trp Lys Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 254
<211> LENGTH: 58
<212> TYPE: PRT
<213> ORGANISM: Artificial sequence
```

<220> FEATURE:
<223> OTHER INFORMATION: Engineered EGFR binding polypeptide

<400> SEQUENCE: 254

Val Asp Asn Lys Phe Asn Lys Glu Thr Asp Arg Ala Ile Lys Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 255
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 255

Val Asp Asn Lys Phe Asn Lys Glu Met Trp Asn Ala Trp His Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 256
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 256

Val Asp Asn Lys Phe Asn Lys Glu Pro Trp Val Ala Trp Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 257
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 257

Val Asp Asn Lys Phe Asn Lys Glu Leu Ile Gly Ala Tyr Asp Glu Ile
1               5                   10                  15

Arg Ser Leu Pro Asn Leu Asn Gly Trp Gln Met Thr Ala Phe Ile Ala
            20                  25                  30

Ser Leu Ala Asp Asp Pro Ser Gln Ser Ala Asn Leu Leu Ala Glu Ala
        35                  40                  45

```
Lys Lys Leu Asn Asp Ala Gln Ala Pro Lys
    50                  55

<210> SEQ ID NO 258
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 258

Val Asp Asn Lys Phe Asn Lys Glu Arg Asp Tyr Ala Leu Trp Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 259
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 259

Val Asp Asn Lys Phe Asn Lys Glu Thr Gln Asp Ala Trp Asp Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 260
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 260

Val Asp Asn Lys Phe Asn Lys Glu Met Trp Glu Ala Trp Gly Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 261
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 261

Val Asp Asn Lys Phe Asn Lys Glu Met Trp Ser Ala Trp His Glu Ile
```

```
                1               5                   10                  15
Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 262
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 262

Val Asp Asn Lys Phe Asn Lys Glu Leu Trp Gln Ala Trp Gly Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 263
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 263

Val Asp Asn Lys Phe Asn Lys Glu Val Glu Arg Ala Trp Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 264
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 264

Val Asp Asn Lys Phe Asn Lys Glu Met Trp Glu Ala Trp Gly Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 265
<211> LENGTH: 58
```

```
<212> TYPE: PRT
<213> ORGANISM: Artificial sequence
<220> FEATURE:
<223> OTHER INFORMATION: Engineered EGFR binding polypeptide

<400> SEQUENCE: 265

Val Asp Asn Lys Phe Asn Lys Glu Arg Thr Gln Ala Ile Arg Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 266
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 266

Val Asp Asn Lys Phe Asn Lys Glu Thr Glu Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 267
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 267

Val Asp Asn Lys Phe Asn Lys Glu Ala Glu Thr Ala Trp Ser Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 268
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 268

Val Asp Asn Lys Phe Asn Lys Glu Met Trp Cys Ala Trp Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
```

Lys Lys Leu Asn Asp Ala Gln Ala Pro Lys
        50                  55

<210> SEQ ID NO 269
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 269

Val Asp Asn Lys Phe Asn Lys Glu Arg Asp Tyr Ala Ile Glu Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 270
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 270

Val Asp Asn Lys Phe Asn Lys Glu Met Trp Ser Ala Trp Asp Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 271
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 271

Val Asp Asn Lys Phe Asn Lys Glu Met Trp Thr Ala Trp His Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 272
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 272

```
Val Asp Asn Lys Phe Asn Lys Glu Thr Asp Arg Ala Val Arg Glu Ile
1               5                  10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 273
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 273

Val Asp Asn Lys Phe Asn Lys Glu Thr Trp Arg Ala Trp His Glu Ile
1               5                  10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 274
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 274

Val Asp Asn Lys Phe Asn Lys Glu Met Trp Leu Ala Trp Gln Glu Ile
1               5                  10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 275
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 275

Val Asp Asn Lys Phe Asn Lys Glu Val Asp Tyr Ala Ile Gln Glu Ile
1               5                  10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 276
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 276

Val Asp Asn Lys Phe Asn Lys Glu Met Glu Ser Ala Trp Ile Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 277
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 277

Val Asp Asn Lys Phe Asn Lys Glu Thr Glu Glu Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 278
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 278

Val Asp Asn Lys Phe Asn Lys Glu Ser Glu Ala Ala Leu Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 279
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 279

Val Asp Asn Lys Phe Asn Lys Glu Phe Arg Lys Ala Ser Asn Glu Ile
1               5                   10                  15

Arg Ser Leu Pro Asn Leu Asn Gly Trp Gln Met Thr Ala Phe Ile Ala
            20                  25                  30
```

```
Ser Leu Ala Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 280
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 280

Val Asp Asn Lys Phe Asn Lys Glu Val Gln Leu Ala Trp Asp Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 281
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 281

Val Asp Asn Lys Phe Asn Lys Glu Ala Asp Arg Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 282
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 282

Val Asp Asn Lys Phe Asn Lys Glu Ile Lys Pro Ala Ile Arg Glu Ile
1               5                   10                  15

His Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 283
<211> LENGTH: 58
<212> TYPE: PRT
<213> ORGANISM: Artificial sequence
<220> FEATURE:
<223> OTHER INFORMATION: Engineered EGFR binding polypeptide
```

<400> SEQUENCE: 283

Val Asp Asn Lys Phe Asn Lys Glu Leu Asp Gln Ala Ile Leu Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 284
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 284

Val Asp Asn Lys Phe Asn Lys Glu Pro Trp Ile Ala Trp His Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 285
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 285

Val Asp Asn Lys Phe Asn Lys Glu Arg Asp Val Ala Ile Thr Glu Ile
1               5                   10                  15

His Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 286
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 286

Val Asp Asn Lys Phe Asn Lys Glu Phe Asp Lys Ala Val Ser Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 287
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 287

Val Asp Asn Lys Phe Asn Lys Glu Val Asp Val Ala Met Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 288
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 288

Val Asp Asn Lys Phe Asn Lys Glu Thr Asn Ala Ala Leu Glu Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 289
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 289

Val Asp Asn Lys Phe Asn Lys Glu Ala Glu Lys Ala Trp Glu Glu Ile
1               5                   10                  15

His Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 290
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 290

Val Asp Asn Lys Phe Asn Lys Glu Pro Trp Leu Ala Trp Ser Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 291
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 291

Val Asp Asn Lys Phe Asn Lys Glu Gly Leu Asn Ala Val Asn Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 292
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 292

Val Asp Asn Lys Phe Asn Lys Glu Trp Glu Val Ala Met Glu Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 293
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 293

Val Asp Asn Lys Phe Asn Lys Glu Val Glu Ser Ala Trp Thr Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 294
<211> LENGTH: 58
<212> TYPE: PRT
<213> ORGANISM: Artificial sequence -continued

```
<220> FEATURE:
<223> OTHER INFORMATION: Engineered EGFR binding polypeptide

<400> SEQUENCE: 294

Val Asp Asn Lys Phe Asn Lys Glu Thr Asp Arg Ala Trp Asp Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 295
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 295

Val Asp Asn Lys Phe Asn Lys Glu Arg Glu Gln Ala Thr Glu Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 296
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 296

Val Asp Asn Lys Phe Asn Lys Glu Met Glu His Ala Trp Glu Glu Ile
1               5                   10                  15

Arg Ser Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 297
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 297

Val Asp Asn Lys Phe Asn Lys Glu His Trp Asn Ala Leu His Glu Ile
1               5                   10                  15

Arg Ser Leu Pro Asn Leu Asn Gly Gly Gln Met Thr Ala Phe Ile Ala
            20                  25                  30

Ser Leu Phe Asp Asp Pro Ser Gln Ser Ala Asn Leu Leu Ala Glu Ala
        35                  40                  45
```

Lys Lys Leu Asn Asp Ala Gln Ala Pro Lys
        50                  55

<210> SEQ ID NO 298
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 298

Val Asp Asn Lys Phe Asn Lys Glu Tyr Glu Ala Ala Trp Asp Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 299
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 299

Val Asp Asn Lys Phe Asn Lys Glu Gly Glu Met Ala Leu Gln Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 300
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 300

Val Asp Asn Lys Phe Asn Lys Glu Phe Arg Trp Ala Ser Asp Glu Ile
1               5                   10                  15

Arg Asn Leu Pro Asn Leu Asn Gly Trp Gln Met Thr Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 301
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 301

Val Asp Asn Lys Phe Asn Lys Glu His Trp Asn Ala Leu His Glu Ile

```
                1               5                   10                  15
Arg Ser Leu Pro Asn Leu Asn Gly Trp Gln Met Thr Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 302
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 302

Val Asp Asn Lys Phe Asn Lys Glu Ile Asp Tyr Ala Ile Arg Glu Ile
1               5                   10                  15

His Asn Leu Pro Asn Leu Asn Gly Trp Gln Met Thr Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 303
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 303

Val Asp Asn Lys Phe Asn Lys Glu Leu Leu Gln Ala Met Leu Glu Ile
1               5                   10                  15

Asn His Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 304
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 304

Val Asp Asn Lys Phe Asn Lys Glu Val Asn Pro Ala Leu Gln Glu Ile
1               5                   10                  15

Arg Ser Leu Pro Asn Leu Asn Gly Trp Gln Met Thr Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 305
<211> LENGTH: 58
```

```
<212> TYPE: PRT
<213> ORGANISM: Artificial sequence
<220> FEATURE:
<223> OTHER INFORMATION: Engineered EGFR binding polypeptide

<400> SEQUENCE: 305

Val Asp Asn Lys Phe Asn Lys Glu Leu Leu Ser Ala Met Leu Glu Ile
1               5                   10                  15

Asn His Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 306
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 306

Val Asp Asn Lys Phe Asn Lys Glu Arg Asp Glu Ala Ile Gln Glu Ile
1               5                   10                  15

His Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 307
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 307

Val Asp Asn Lys Phe Asn Lys Glu Thr Asp Trp Ala Ile Gln Glu Ile
1               5                   10                  15

Arg Ser Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 308
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 308

Val Asp Asn Lys Phe Asn Lys Glu Met Glu Lys Ala Trp Val Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
```

Lys Lys Leu Asn Asp Ala Gln Ala Pro Lys
    50                  55

<210> SEQ ID NO 309
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 309

Val Asp Asn Lys Phe Asn Lys Glu Leu Asp Asn Ala Ile Asp Glu Ile
1               5                   10                  15

Arg Asn Leu Pro Asn Leu Asn Gly Trp Gln Met Thr Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 310
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 310

Val Asp Asn Lys Phe Asn Lys Glu Met Trp Ile Ala Trp Glu Glu Ile
1               5                   10                  15

Arg Asp Leu Pro Asn Leu Asn Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 311
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 311

Val Asp Asn Lys Phe Asn Lys Glu Met Trp Leu Ala Trp Glu Glu Ile
1               5                   10                  15

Arg Asn Leu Pro Asn Leu Asn Gly Trp Gln Leu Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 312
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 312

Val Asp Asn Lys Phe Asn Lys Glu Met Trp Ser Ala Trp Asp Glu Ile
1               5                   10                  15

Arg Ala Leu Pro Asn Leu Asn Gly Trp Gln Met Thr Ala Phe Ile Ser
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 313
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 313

Val Asp Asn Lys Phe Asn Lys Glu Met Trp Asn Ala Trp Asn Glu Ile
1               5                   10                  15

Arg Asp Leu Pro Asn Leu Asn Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 314
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 314

Val Asp Asn Lys Phe Asn Lys Glu Met Trp Gly Ala Trp Asn Glu Ile
1               5                   10                  15

Arg Asp Leu Pro Asn Leu Asn Gly Trp Gln Met Thr Ala Phe Ile Ser
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 315
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 315

Val Asp Asn Lys Phe Asn Lys Glu Met Trp Ile Ala Trp Asp Glu Ile
1               5                   10                  15

Arg Asp Leu Pro Asn Leu Asn Gly Trp Gln Phe Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 316
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 316

Val Asp Asn Lys Phe Asn Lys Glu Leu Trp Ile Ala Trp Asp Glu Ile
1               5                   10                  15

Arg Tyr Leu Pro Asn Leu Asn Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 317
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 317

Val Asp Asn Lys Phe Asn Lys Glu Met Trp Lys Ala Trp Glu Glu Ile
1               5                   10                  15

Arg Ser Leu Pro Asn Leu Asn Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 318
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 318

Val Asp Asn Lys Phe Asn Lys Glu Met Trp Asp Ala Trp Gly Glu Ile
1               5                   10                  15

Arg Asn Leu Pro Asn Leu Asn Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 319
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 319

Val Asp Asn Lys Phe Asn Lys Glu Val Trp Val Ala Trp Glu Glu Ile
1               5                   10                  15

Arg Asp Leu Pro Asn Leu Asn Gly Trp Gln Met Thr Ala Phe Ile Ala
            20                  25                  30
```

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 320
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 320

Val Asp Asn Lys Phe Asn Lys Glu Met Trp Gly Ala Trp Glu Glu Ile
1               5                   10                  15

Arg Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 321
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 321

Val Asp Asn Lys Phe Asn Lys Glu Met Trp Met Ala Trp Asp Glu Ile
1               5                   10                  15

Arg Tyr Leu Pro Asn Leu Asn Gly Trp Gln Leu Thr Ala Phe Ile Ser
                20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 322
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 322

Val Asp Asn Lys Phe Asn Lys Glu Met Trp Val Ala Trp Glu Glu Ile
1               5                   10                  15

Arg Asn Leu Pro Asn Leu Asn Gly Trp Gln Met Thr Ala Phe Ile Gly
                20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 323
<211> LENGTH: 58
<212> TYPE: PRT
<213> ORGANISM: Artificial sequence
<220> FEATURE:
<223> OTHER INFORMATION: Engineered EGFR binding polypeptide

```
<400> SEQUENCE: 323

Val Asp Asn Lys Phe Asn Lys Glu Met Trp Asp Ala Trp Asp Glu Ile
1               5                   10                  15

Arg Tyr Leu Pro Asn Leu Asn Gly Trp Gln Phe Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 324
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 324

Val Asp Asn Lys Phe Asn Lys Glu Leu Trp Gly Ala Trp Asp Glu Ile
1               5                   10                  15

Arg Tyr Leu Pro Asn Leu Asn Gly Trp Gln Met Thr Ala Phe Ile Ala
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 325
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 325

Val Asp Asn Lys Phe Asn Lys Glu Ser Trp Asn Ala Val Lys Glu Ile
1               5                   10                  15

Gly Glu Leu Pro Asn Leu Asn Trp Gly Gln Ala Asp Ala Phe Ile Asn
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 326
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 326

Val Asp Asn Lys Phe Asn Lys Glu Ser His Glu Val Trp Gln Glu Ile
1               5                   10                  15

Arg Ser Leu Pro Asn Leu Asn Gly Trp Gln Leu Thr Ala Phe Ile Asn
            20                  25                  30

Ser Leu Leu Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 327
<211> LENGTH: 58
<212> TYPE: PRT
<213> ORGANISM: Artificial sequence
<220> FEATURE:
<223> OTHER INFORMATION: Engineered EGFR binding polypeptide

<400> SEQUENCE: 327

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 328
<211> LENGTH: 1210
<212> TYPE: PRT
<213> ORGANISM: Homo sapiens

<400> SEQUENCE: 328

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro

-continued

```
                260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Thr Asp His
        290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
```

-continued

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

```
Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 329
<211> LENGTH: 621
<212> TYPE: PRT
<213> ORGANISM: Homo sapiens

<400> SEQUENCE: 329

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270
```

```
Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
            290                 295                 300

Cys Glu Gly Pro Cys Arg Lys Val Cys Asn Gly Ile Gly Ile Gly Glu
305             310                 315                     320

Phe Lys Asp Ser Leu Ser Ile Asn Ala Thr Asn Ile Lys His Phe Lys
            325                 330                 335

Asn Cys Thr Ser Ile Ser Gly Asp Leu His Ile Leu Pro Val Ala Phe
            340             345                 350

Arg Gly Asp Ser Phe Thr His Thr Pro Pro Leu Asp Pro Gln Glu Leu
            355             360             365

Asp Ile Leu Lys Thr Val Lys Glu Ile Thr Gly Phe Leu Leu Ile Gln
            370             375             380

Ala Trp Pro Glu Asn Arg Thr Asp Leu His Ala Phe Glu Asn Leu Glu
385             390             395                 400

Ile Ile Arg Gly Arg Thr Lys Gln His Gly Gln Phe Ser Leu Ala Val
                405             410                 415

Val Ser Leu Asn Ile Thr Ser Leu Gly Leu Arg Ser Leu Lys Glu Ile
            420             425             430

Ser Asp Gly Asp Val Ile Ile Ser Gly Asn Lys Asn Leu Cys Tyr Ala
            435             440             445

Asn Thr Ile Asn Trp Lys Lys Leu Phe Gly Thr Ser Gly Gln Lys Thr
            450             455             460

Lys Ile Ile Ser Asn Arg Gly Glu Asn Ser Cys Lys Ala Thr Gly Gln
465             470             475                 480

Val Cys His Ala Leu Cys Ser Pro Glu Gly Cys Trp Gly Pro Glu Pro
            485             490             495

Arg Asp Cys Val Ser Cys Arg Asn Val Ser Arg Gly Arg Glu Cys Val
            500             505             510

Asp Lys Cys Asn Leu Leu Glu Gly Glu Pro Arg Glu Phe Val Glu Asn
            515             520             525

Ser Glu Cys Ile Gln Cys His Pro Glu Cys Leu Pro Gln Ala Met Asn
            530             535             540

Ile Thr Cys Thr Gly Arg Gly Pro Asp Asn Cys Ile Gln Cys Ala His
545             550             555             560

Tyr Ile Asp Gly Pro His Cys Val Lys Thr Cys Pro Ala Gly Val Met
                565             570             575

Gly Glu Asn Asn Thr Leu Val Trp Lys Tyr Ala Asp Ala Gly His Val
            580             585             590

Cys His Leu Cys His Pro Asn Cys Thr Tyr Gly Cys Thr Gly Pro Gly
            595             600             605

Leu Glu Gly Cys Pro Thr Asn Gly Pro Lys Ile Pro Ser
            610             615             620
```

POLYPEPTIDES

CROSS-REFERENCE TO RELATED APPLICATIONS

This application is a Divisional of U.S. patent application Ser. No. 12/085,576 filed Aug. 20, 2008, now U.S. Pat. No. 8,247,375 issued Aug. 21, 2012, which is a US National Stage application of International Patent Application Serial No. PCT/EP2006/011669 filed Dec. 5, 2006.

FIELD OF THE INVENTION

This invention relates to polypeptides which bind to Epidermal Growth Factor Receptor (EGFR). The polypeptides have industrial applications in medicine, veterinary medicine, imaging, separation techniques and diagnostics.

BACKGROUND

Abnormal expression of receptors in the Epidermal Growth Factor Receptor family, (the EGFR-family; also called the ErbB receptor family), is frequently associated with various malignancies in lung, breast, prostate, colon, ovary, head and neck. It is of interest to study this receptor family to gain a better understanding of the relation of the receptors to patient prognosis and treatment. The family consists of four transmembrane receptors, the epidermal growth factor receptor, EGFR, (ErbB1/HER1), HER2 (ErbB2/neu), HER3 (ErbB3) and HER4 (ErbB4) (Gullick W J. Endocr Rel Canc 2001; 8:75-82; Witton C J. et al J Pathol 2003; 200:290-297). Each receptor comprises an extra-cellular ligand binding domain, a transmembrane domain and an intracellular tyrosine kinase domain (except HER3 which lacks a functional tyrosine kinase domain) (Citri A, et al. Exp Cell Res 2003; 284(1):54-65; Harari D and Yarden Y. Oncogene 2002; 19:6102-6114). There is one EGFR variant which has almost no ECD-EGFRvIII, Wikstrand C J et al Cancer Res. 55: 3140-3148, 1995; Huang H S et al J. Biol. Chem. 272: 2927-2935, 1997; Kuan C T, et al Endocr. Relat. Cancer 8:83-96, 2001.

When a ligand binds to a receptor in the EGFR family, the receptor is stimulated to dimerise, either with another identical receptor (homodimerization) or with another receptor in the family (heterodimerization) (Olayioye M A, et al. Embo J. 2000; 19:3159-67; Yarden Y, Sliwkowski M X. Cell Biol 2001; 2:127-37). Receptor dimerization activates the intracellular tyrosine kinase domain, leading to proliferation, migration, apoptosis, differentiation or other cellular processes (Yarden Y, Sliwkowski M X. Cell Biol 2001; 2:127-37; Wells A. Int J Biochem Cell Biol 1999; 31:637-643; Vermeer P D et al. Nature 2003; 422:322-6). EGFR and HER2 are the most studied receptors of the four in the family and are over-expressed in many malignancies (Nordberg E et al. Eur J Nucl Med Mol. Imaging. 2005 July; 32(7):771-7). A high expression of these particular receptors is often associated with a poor prognosis (Hendriks B S et al. J Biol Chem 2003; 278: 23343-23351; Arteaga C L. Oncologist 2002; 7 Suppl 4:31-9; Earp H S et al. Breast Cancer Res Treat 1995; 35:115-32; Wester K, et al. Acta Oncol 2002; 41:282-8. Lorenzo G D et al. Clin Prostate Cancer 2003; 2(1):50-7).

Several ligands bind to members of the EGFR receptor family. The only receptor that does not have any known natural ligand is HER2. (Citri A, et al. Exp Cell Res 2003; 284(1):54-65; Yarden Y, Sliwkowski M X. Cell Biol 2001; 2:127-37; Lenferink A E G, et al. EMBO J. 1998; 17:3385-3397). The antibody trastuzumab (Herceptin), which binds to the extra-cellular domain, may be used to target the HER2 receptor, especially in HER2 expressed tumors in breast cancer. Binding of trastuzumab can block growth stimulating intracellular signalling, decrease the capacity of cellular repair after chemo- and radiotherapy and possibly also improve the capacity of apoptosis. Bookman M A et al. J Clin Oncol 2003; 21:283-290; Pegram M D et al. Cancer Treat Res 2000; 103:747-75; McKeage K, Perry C M. Drugs 2002; 62:209-43). Affibody molecules disclosed in WO2005/003156 may also be used to target HER2.

EGFR function can be inhibited by blocking ligand binding to the extra-cellular part of the receptor, using antibodies such as cetuximab (Erbitux, ImClone/Bristol Myers Squibb) (Baselga J. Eur J Cancer 37: Suppl 4, S16-22, 2001, ABX-EGF Ranson M, Curr Opin Mol Ther 5: 541-546, 2003 or mab425/EMD55900 (Merck) or antibody fragments (Boskovitz A et al: Expert Opin Biol Ther 4: 1453-1471, 2004). The receptor function may in some, but not all patients, also be blocked with low molecular weight tyrosine kinase inhibitors such as Iressa (Gefitinib, AstraZeneca) (Sundberg A L et al: Eur J Nucl Med Mol Imaging 30: 1348-1356, 2003; Herbst R S et al: Nat Rev Cancer 4: 956-965, 2004) or Tarceva (Erlotinib, OSI-774) (Krozely P. Clin J Oncol Nurs 8: 163-168, 2004) that bind the intracellular part of the receptor. In both cases, the aim is to block growth-stimulating signalling, and thereby inhibit tumor cell proliferation (Rich J N, Bigner D D: Nat Rev Drug Discov 3: 430-446, 2004). There is, however, room for improvement. For example Iressa has proven to be a disappointment, acting in only a fraction of patients over-expressing the EGFR. For cetuximab, it still remains to be seen what will be the best chemotherapy combination treatment modality to increase the therapeutic impact of the treatment. These therapies can be combined with a radionuclide-based approach to kill tumor cells (Carlsson J, et al: Radiotherapy and Oncology, 66(2), 107-117, 2003), and one interesting example is the recent application of Gefitinib to modify the uptake and therapy effects of radio-labeled (astatinated) EGF (Sundberg A L et al: Eur J Nucl Med Mol Imaging 30: 1348-1356, 2003). Development of polypeptide anti-EGFR targeting agents provides an interesting alternative to the naturally agonistic (tumor-stimulating) biological EGF ligand, for the delivery of radionuclides for both diagnostic (imaging) and therapy purposes, as previously exemplified for HER-2 (Wikman M et al. Protein Engineering, Design & Selection (PEDS), 17(5), 455-462, 2004; Steffen A C et al. Cancer Biotherapy and Radiopharmaceuticals, 20, 239-248, 2005; Steffen A C et al. Eur J Nuclear Medicine, In press, 2005). Such polypeptides can also have biological effects, even without radioactivity, that are of interest for therapy. Z variants, also called "Affibody® molecules", as disclosed for example in WO2005/0003156, are polypeptides which are intermediate in molecular weight (6-15 kDa), and can therefore have better penetration in tumor tissue than antibodies (150 kDa), and at the same time have better systemic circulation properties than low molecular weight substances like Iressa and Tarceva (≈1 kDa) which are rapidly eliminated via kidney excretion. In fact, Z variants typically have half-lives in a range suitable for in vivo imaging applications, and if needed for therapeutic or other applications, half-lives can be extended dramatically by gene fusion technology (see for example WO 2005/097202A).

Over-expression of EGFR is common in Head and Neck Squamous Cell Carcinomas, (HNSCC) (Rikimaru, K et al. Head Neck, 1992. 14(1): p. 8-13; Santini, J et al, Head Neck, 1991. 13(2): p. 132-9. Ekberg T et al. Int J Oncology, 26(5), 1177-1185, 2005). Increased levels of HER2 have been suggested in several studies of HNSCC (Craven, J. M et al.

Anticancer Res, 1992. 12(6B): p. 2273-6), with possible prognostic value in oral Squamous Cell Carcinomas, (SCC) (Werkmeister, et al. Oral Oncol, 2000. 36(1): p. 100-5; Werkmeister, R. Am J Surg, 1996. 172(6): p. 681-3; Xia, W et al. Clin Cancer Res, 1997. 3(1): p. 3-9; Xia, W et al. Clin Cancer Res, 1999. 5(12): p. 4164-74). HER3 has been shown to be over expressed in HNSCC cell lines and associated with clinical malignant progression (Xia, W et al. Clin Cancer Res, 1999. 5(12): p. 4164-74; Shintani, S et al. Cancer Lett, 1995. 95(1-2): p. 79-83) and to be over expressed also in other types of malignancies (Gullick, W. J. Cancer Surv, 1996. 27: p. 339-49). Some human mammary carcinoma cell lines have HER4 transcripts (Plowman, G. D et al. Proc Natl Acad Sci USA, 1993. 90(5): p. 1746-50) but the role of HER4 in cancer is less clear (Srinivasan, R. et al. Cancer Res, 2000. 60(6): p. 1483-7). It is interesting to study co-expression of the four receptors, since it has been suggested that co-expression patterns may be associated with malignant phenotypes (Xia, W et al. Clin Cancer Res, 1999. 5(12): p. 4164-74; Bei, R. et al. J Pathol, 2001. 195(3): p. 343-8; Krahn, G. et al. Eur J Cancer, 2001. 37(2): p. 251-9). Immunohistochemical stainings of EGFR and HER2 have shown pronounced membranous staining. In contrast, HER3 and HER4 staining has been mainly cytoplasmic (Plowman, G. D et al. Proc Natl Acad Sci USA, 1993. 90(5): p. 1746-50; Srinivasan, R. et al. Cancer Res, 2000. 60(6): p. 1483-7). Furthermore, EGFR and HER2 have been reported to express at high levels in both tumors and metastases. Thus, it seems that EGFR and HER2 are potential targets for macromolecular and peptide-based in vivo imaging and therapy applications while this might not be the case with HER3 and HER4.

Increased levels of EGFR-protein have also been found in urinary bladder carcinoma and the over-expression has been related to tumor stage and malignancy grade (Harney, J. V. et al, J Urol, 146, 227-31. (1991); Messing, E. M. Cancer Res, 50, 2530-7. (1990); Neal, D. E. et al, Cancer, 65, 1619-25. (1990); Sauter, G. et al. Int J Cancer, 57, 508-14. (1994); Gardmark T, et al. British Journal of Urology (BJU), 95, 982-986, 2005).

In Glioblastoma Multiforme (GBM) the most malignant form of the gliomas, which are common primary central nervous system tumors, over-expression of EGFR is detected in at least half of all analyzed tumors. (Boskovitz A, et al. Expert Opin Biol Ther 4: 1453-1471, 2004; Shinojima N, et al. Cancer Res 63: 6962-6970, 2003; Ekstrand A J, et al al. Cancer Res 51: 2164-2172, 1991; Rainov N G et al. Journal of Neuro-Oncology 35 13-28 (1997); Carlsson J et al. J. Neurooncol. 2005 Sep. 8; [Epub ahead of print]). The over-expression is due to gene amplification and/or increased transcription rates, and the number of $10^6$ receptors per tumor cell has been reported (Rich J N, Signer D D: Nat Rev Drug Discov 3: 430-446, 2004; Bigner S H et al. J Neuropathol Exp Neurol 47, 191-205 (1998); Carpenter G. Ann Rev Biochem 56, 881-914 (1987); Collins V P. Cancer. Biology 4, 27-32 (1993); Libermann T A et al. Nature 313, 144-147, (1985); Kleihues P, Ohgaki H. Neuro-oncol 1, 44-51, (1999); Kleihues P, Ohgaki H. Toxicol Pathol 28, 164-170, (2000); Boskovitz A et al. Expert Opin Biol Ther 4, 1453-1471, (2004)). EGFR over-expression correlates with increased glioma growth rate and decreased survival (Rich J N, Bigner D D: Nat Rev Drug Discov 3, 430-446, (2004); Carlsson J et al. J. Neurooncol. 2005 Sep. 8; [Epub ahead of print]; Schlegel J et al. Int J Cancer 56, 72-77, (1994); Wikstrand C J, Bigner D D. J Natl Cancer Inst 90, 799-801, (1998); Shinojima N et al. Cancer Res 63, 6962-6970, (2003)) and it has been indicated that EGFR over-expression is most pronounced at the tumor cell invading edges (Okada Y, et al. Cancer Res 63, 413-416,)(2003)). EFGR-specific binding polypeptides could potentially be employed for therapy applications for glioma therapy, for example, by locoregional administration into the postoperal cavity.

Several other malignancies of epithelial origin, such as those found in lung and breast, are also associated with a high expression of EGFR (Salomon, D. S. et al. Crit. Rev. Oncol. Hematol., 19(3):183-232, (1995)). EGFR receptors are also distributed among various normal tissues and expressed to rather high levels especially in liver hepatocytes and skin epithelium (Gusterson, B. et al. Cell Biol Int Rep, 8, 649-58. (1984); Damjanov, I. et al. Lab Invest, 55, 588-92. (1986)). This can potentially cause problems in therapy applications, especially radiotherapy, but is probably of less importance in diagnostic and imaging applications where low amounts of diagnostic or imaging markers which bind to EGFR receptors are given. Nevertheless, EGFR-binding polypeptides might find applications in certain cancers where local administration is to be considered.

It is an object of the invention to provide new EGFR-binding agents, that could be used for diagnostic, in vitro or in vivo imaging, as well as therapeutic applications. In addition, such EGFR binding polypeptides might find use in staging and as a direct assessment of SME based therapy aimed to down-regulate the target receptor.

In addition to the development of marketed molecular imaging agents, applications include use in the drug development and screening procedure where specific imaging agents are desired to measure outcome of treatment in in vivo models and subsequently during clinical development. Molecular Imaging provides a direct read-out of efficacy of a pharmaceutical aimed to down-regulate a growth factor receptor, as well as for assessing the anti-tumor effect.

SUMMARY OF THE INVENTION

According to one aspect thereof, the invention provides an epidermal growth factor receptor (EGFR) binding polypeptide, comprising an epidermal growth factor receptor binding motif, EBM, which motif consists of an amino acid sequence selected from:

i) $EX_2X_3X_4AX_6X_7EIX_{10}\ X_{11}LPNLNX_{17}X_{18}QX_{20}$ $X_{21}AFIX_{25}SLX_{28}D$, wherein, independently of each other,
$X_2$ is selected from M, F, V, L, I and S;
$X_3$ is selected from W, D, E and L;
$X_4$ is selected from I, V, G, S, M, L, A, T, N, D and W;
$X_6$ is selected from W, V, L, I, M and S;
$X_7$ is selected from D, E, N and K;
$X_{10}$ is selected from R, G, H and K;
$X_{11}$ is selected from D, N, E, Y and S;
$X_{17}$ is selected from G, W and A;
$X_{18}$ is selected from W, G and A;
$X_{20}$ is selected from M, L, F, A and E;
$X_{21}$ is selected from T, D, N, A and Q;
$X_{25}$ is selected from A, S, N, G and L; and
$X_{28}$ is selected from L, W, V, F and A;
and
ii) an amino acid sequence which has at least 85% identity to the sequence defined in i);
the EGFR-binding polypeptide binding to EGFR such that the $K_D$ value of the interaction is at most 10 µM.

The above definition of a class of sequence related, EGFR-binding polypeptides according to the invention is based on a statistical analysis of a large number of random polypeptide variants of a parent scaffold, that were selected for their interaction with EGFR in several different selection experiments. The identified EGFR-binding motif, or "EBM", corresponds to the target binding region of the parent scaffold, which region constitutes two alpha helices within a three-helical bundle protein domain. In the parent scaffold, the varied amino acid residues of the two EBM helices constitute a binding surface for interaction with the constant Fc part of antibodies. In the present invention, the random variation of binding surface residues and the subsequent selection of variants have replaced the Fc interaction capacity with a capacity for interaction with EGFR.

As the skilled person will realize, the function of any polypeptide, such as the EGFR-binding capacity of the polypeptides according to the invention, is dependent on the tertiary structure of the polypeptide. It is therefore possible to make minor changes to the sequence of amino acids in a polypeptide without affecting the function thereof. Thus, the invention encompasses modified variants of the EBM of i), which are such that the resulting sequence is at least 85% identical to a sequence belonging to, the class defined by i). For example, it is possible that an amino acid residue belonging to a certain functional grouping of amino acid residues (e.g. hydrophobic, hydrophilic, polar etc) could be exchanged for another amino acid residue from the same functional group.

In one embodiment of the polypeptide according to the invention, $X_2$ is M.

In one embodiment of the polypeptide according to the invention, $X_3$ is W.

In one embodiment of the polypeptide according to the invention, $X_4$ is selected from I, V, G and S.

In one embodiment of the polypeptide according to the invention, $X_6$ is selected from V and W.

In one embodiment of the polypeptide according to the invention, $X_{10}$ is selected from R and G.

In one embodiment of the polypeptide according to the invention, $X_{11}$ is selected from D, N and E.

In one embodiment of the polypeptide according to the invention, $X_{17}$ is selected from W and G.

In one embodiment of the polypeptide according to the invention, $X_{18}$ is selected from W and G, and may in particular be W.

In one embodiment of the polypeptide according to the invention, $X_{20}$ is M.

In one embodiment of the polypeptide according to the invention, $X_{21}$ is selected from T and D, and may in particular be T.

In one embodiment of the polypeptide according to the invention, $X_{25}$ is selected from A, S and N.

In one embodiment of the polypeptide according to the invention, $X_{28}$ is selected from L and W.

In one embodiment of the polypeptide according to the invention, $X_{18}$ is W and $X_{21}$ is T.

In one embodiment of the polypeptide according to the invention, $X_{18}$ is W and $X_{20}$ is M.

In a more specific definition of a sub-class of the polypeptides according to the invention, the amino acid sequence of i) fulfils at least six, at least seven, at least eight or all nine of the following nine conditions: $X_2$ is M; $X_3$ is W; $X_6$ is W; $X_{10}$ is R; $X_{17}$ is G; $X_{18}$ is W; $X_{20}$ is M; $X_{21}$ is T; $X_{28}$ is L.

In the case where all nine of these conditions are fulfilled, the sequence of i) is $EMWX_4AWX_7EIR\ X_{11}LPNLNGWQM$
$TAFIX_{25}SLLD.$ In an alternative specific definition of a sub-class of the polypeptides according to the invention, the amino acid sequence of i) fulfils at least three, at least four or all five of the following five conditions: $X_{17}$ is G; $X_{18}$ is W; $X_{20}$ is M; $X_{21}$ is T; $X_{25}$ is A.

In the case where all five of these conditions are fulfilled, the sequence of i) is $EX_2X_3X_4AX_6X_7EIX_{10}\ X_{11}LPNLNGWQM\ TAFIASLX_{28}D.$ In yet an alternative subclass, the sequence of i) is $EX_2X_3X_4AX_6X_7EIG$ $X_{11}LPNLNWGQX_{20}$ $X_{21}AFIX_{25}SLWD$, for example $EX_2X_{31}AVX_7EIG$ ELP-NLNWGQX$_{20}$ DAFINSLWD.

As described in detail in the experimental section to follow, the selection of EGFR-binding variants has led to the identification of a large amount of individual EGFR-binding motif (EBM) sequences. These sequences constitute individual embodiments of the EBM sequence i) in the definition of EGFR-binding polypeptides according to this aspect of the present invention. The sequences of individual EGFR-binding motifs are presented in FIG. 1 and as SEQ ID NO:1-163. In embodiments of this aspect of the invention, the EBM sequence i) may in particular be selected from SEQ ID NO:33, SEQ ID NO:48, SEQ ID NO:57, SEQ ID NO:87, SEQ ID NO:88 and SEQ ID NO:147.

In embodiments of the present invention, the EBM may form part of a three-helix bundle protein domain. For example, the EBM may essentially constitute or form part of two alpha helices with an interconnecting loop, within said three-helix bundle protein domain.

In particular embodiments of the invention, such a three-helix bundle protein domain is selected from domains of bacterial receptor proteins. Non-limiting examples of such domains are the five different three-helical domains of protein A from *Staphylococcus aureus*, and derivatives thereof. Thus, an EGFR-binding polypeptide according to the invention may comprise an amino acid sequence selected from:

ADNNFNK-[EBM]-DPSQSANLLSEAKKLNESQAPK (EBM within domain A of staphylococcal protein A);

ADNKFNK-[EBM]-DPSQSANLLAEAKKLNDAQAPK (EBM within domain B of staphylococcal protein A);

ADNKFNK-[EBM]-DPSVSKEILAEAKKLNDAQAPK (EBM within domain C of staphylococcal protein A);

ADAQQNNFNK-[EBM]-DPSQSTNVLGEAKKLNESQAPK (EBM within domain D of staphylococcal protein A);

AQHDE-[EBM]-DPSQSANVLGEAQKLNDSQAPK (EBM within domain E of staphylococcal protein A);
and VDNKFNK-[EBM]-DPSQSANLLAEAKKLNDAQAPK (EBM within the protein Z derivative of domain B of staphylococcal protein A);

wherein [EBM] is an EGFR-binding motif as defined above.

According to another aspect of the invention, there is provided an EGFR-binding polypeptide comprising an amino acid sequence derived from the amino acid sequence SEQ ID NO:327:

VDNKFNK EQQNAFYEILH LPNLNE EQRNAFIQSLKD DPSQ
SANLLAEAKKLNDA QAPK by comprising amino acid substitutions at any or all of positions 9 to 11, 13 to 14, 17 to 18, 24 to 25, 27 to 28, 32 and 35 of the above sequence, or positions corresponding to those positions, which substitutions improve binding of the polypeptide to EGFR compared to a polypeptide comprising the unmodified amino acid sequence, and in which the EGFR-binding polypeptide binds to EGFR such that the $K_D$ value of the interaction is at most 10 µM.

According to another alternative aspect thereof, the invention provides an EGFR-binding polypeptide, whose amino acid sequence comprises a sequence which fulfils one definition selected from the following: iii) it is selected from SEQ ID NO:164-326, and iv) it is an amino acid sequence having 85% or greater identity to a sequence selected from SEQ ID NO:164-326. In embodiments of this aspect of the invention, the EGFR-binding polypeptide may in particular comprise a sequence selected from SEQ ID NO:196, SEQ ID NO:211, SEQ ID NO:220, SEQ ID NO:250, SEQ ID NO:251, SEQ ID NO:310, and sequences having 85% or greater identity thereto.

An EGFR-binding polypeptide according to any aspect of the invention may bind to EGFR such that the $K_D$ value of the interaction is at most $1\times10^{-6}$ M, for example at most $1\times10^{-7}$ M.

When reference is made herein to the degree of identity between the amino acid sequences of different polypeptides, the lower limit of 85% identity to a sequence disclosed herein is given. In some embodiments, the inventive polypeptide may have a sequence which is at least 86%, at least 87%, at least 88%, at least 89%, at least 90%, at least 91%, at least 92%, at least 93%, at least 94%, at least 95%, at least 96%, at least 97%, at least 98% or at least 99% identical to the sequence described herein. The comparison may be performed over a window corresponding to the shortest of the sequences being compared, or over a window corresponding to an EGFR-binding motif in at least one of the sequences being compared.

The polypeptides are advantageous in that they bind well to an EGFR. Typically, the polypeptides can be relatively short and by virtue of their small size they should have better penetration in tumor tissue than antibodies while at the same time have better systemic circulation properties than conventional low molecular weight EGFR-binding substances (often too short half-lives) and monoclonal antibodies (often too long circulation times).

A polypeptide in accordance with the invention may be about 53-58 amino acids in length. However, the length can be greater or smaller. The length of the polypeptide can for example be reduced at the N terminus by up to four amino acids.

The use of the term "position" is relative. In a polypeptide in accordance with the invention which is also 53 amino acids long like the unmodified polypeptide mentioned above, the positions of amino acids in the polypeptide correspond exactly with those in the unmodified polypeptide when a situation where there is, for example, an N terminal extension compared to the unmodified polypeptide those amino acid residues in the modified peptide corresponding to the unmodified peptide have the same position number. For example if there is a six and amino acid residue extension on the modified polypeptide then amino acid number seven of that modified polypeptide, accounting from the N terminus corresponds to the amino acid in position number one of the unmodified polypeptide.

Accordingly, the polypeptides of the invention may be used as an alternative to conventional antibodies or low molecular weight substances in various medical, veterinary, diagnostic and imaging applications. For example, the EGFR-binding polypeptides of the invention may be used in the treatment of EGFR-related cancers such as those caused by over-expression of EGFR described above, especially when local distribution is applied, e.g. glioma. The EGFR-binding polypeptides of the invention may also be used to inhibit cell signalling by binding to an EGFR on a cell surface, in the diagnosis of cancer, both in vivo and in vitro in targeting agents to cells which express EGFR, particularly cells which over-express EGFR, in histochemical methods for the detection of EGFR, in methods of separation and other applications. In addition to the development of molecular imaging agents for the clinic, an application exists for specific preclinical imaging agents to measure outcome of treatment in in vivo models and subsequently during clinical development. Molecular Imaging should provide a direct read-out of the efficacy of a pharmaceutical aimed to down-regulate a growth factor receptor e.g. HER2 or EGFR, as well as for assessing the anti-tumor effect. The polypeptides of the invention may be useful in any method which relies on affinity for EGFR of a reagent. Thus, the polypeptides may be used as a detection reagent, a capture reagent or a separation reagent in such methods, but also as a therapeutic agent in their own right or as a means for targeting other therapeutic agents, with direct (e.g. toxic molecules, toxins) or indirect therapeutic effects (e.g. cancer vaccines, immunostimulatory molecules) to the EGFR protein.

Methods that employ the polypeptides in accordance with the invention in vitro may be performed in different formats, such as microtitre plates, in protein arrays, on biosensor surfaces, on beads, in flow cytometry, on tissue sections, and so on.

The skilled addressee will appreciate that various modifications and/or additions can be made to a polypeptide according to the invention in order to tailor the polypeptide to a specific application without departing from the scope of the present invention. These modifications and additions are described in more detail below and may include additional amino acids in the same polypeptide chain, or labels and/or therapeutic agents that are chemically conjugated or otherwise bound to the polypeptide of the invention.

Furthermore, the invention also encompasses fragments of EGFR-binding polypeptides derived from protein A that retain EGFR-binding. The possibility of creating fragments of a wild-type SPA domain with retained binding specificity was shown by Braisted A C et al in Proc Natl Acad Sci USA 93:5688-5692 (1996). In the experiments described in that paper, using a structure-based design and phage display methods, the binding domain of a three-helix bundle of 59 residues was reduced to a resulting two-helix derivative of 33 residues. This was achieved by stepwise selection of random mutations from different regions, which caused the stability and binding affinity to be iteratively improved. Following the same reasoning, with the polypeptides of the present invention, the skilled addressee will be able to obtain a "minimized" EGFR-binding polypeptide with the same binding properties as that of the "parent" EGFR-binding polypeptide. Thus, a polypeptide constituting a fragment of a polypeptide according to the invention, is within the scope of the invention.

The terms "EGFR-binding" and "binding affinity for EGFR" as used in this specification refers to a property of a polypeptide which may be tested for example by the use of surface plasmon resonance technology, such as in a Biacore instrument. For example as described in the examples below, EGFR-binding affinity may be tested in an experiment in which EGFR, or a fragment of EGFR such as the extracellular domain thereof, is immobilized on a sensor chip of the instrument, and the sample containing the polypeptide to be tested is passed over the chip. Alternatively, the polypeptide to be tested is immobilized on a sensor chip of the instrument, and a sample containing EGFR, or a fragment of EGFR such as the extracellular domain thereof, is passed over the chip. EGFR may, in this regard, be a polypeptide comprising the amino acid sequence SEQ ID NO:328, and its extracellular domain may be a polypeptide comprising the amino acid sequence SEQ ID NO:329. The skilled person may then interpret the results obtained by such experiments to establish at least a qualitative measure of the binding affinity of the polypeptide for EGFR. If a qualitative measure is desired, for example to determine a $K_D$ value for the interaction, surface plasmon resonance methods may also be used. Binding values may for example be defined in a Biacore 2000 instrument (Biacore AB). EGFR is immobilized on a sensor chip of the measurement, and samples of the polypeptide whose affinity is to be determined are prepared by serial dilution and injected in random order. $K_D$ values may then be calculated from the results using for example the 1:1 Langmuir binding model of the BIAevaluation 4.1 software provided by the instrument manufacturer (Biacore AB).

Where amino acid substitutions are introduced, these should not affect the basic structure of the polypeptide. For example, the overall folding of the Ca backbone of the polypeptide can be essentially the same as that of a Z "wild-type" domain to which it is related, i.e. having the same elements of secondary structure in the same order. Thus polypeptides having this basic structure will have similar CD spectra to the Z "wild-type" domain. The skilled addressee is aware of other parameters that may be relevant. The requirement of conserving the basic structure, places restrictions on which positions of the amino acid sequence may be subject to substitution. For example, it is preferred that amino acid residues located on the surface of the polypeptide are substituted, whereas amino acid residues buried within the core of the polypeptide "three-helix bundle" should be kept constant in order to preserve the structural properties of the molecule. The same reasoning applies to fragments of polypeptides of the invention.

The invention also covers polypeptides in which the EGFR-binding polypeptide described above is present as an EGFR-binding domain to which additional amino acid residues have been added at either terminal. These additional amino acid residues may play a role in the binding of EGFR by the polypeptide, but may equally well serve other purposes, related for example to one or more of the production, purification, stabilization, coupling or detection of the polypeptide. Such additional amino acid residues may comprise one or more amino acid residues added for the purpose of chemical coupling. One example of this, is the addition of a cysteine residue at the very first or very last position in the polypeptide chain, i.e. at the N. or C terminus. Such additional amino acid residues may also provide a "tag" for purification or detection of the polypeptide such as a $His_6$ tag or a "myc" tag or a "flag" tag for interaction with antibodies specific to the tag.

The invention also covers EGFR-binding polypeptides in which a EGFR-binding polypeptide as described above is present as an EGFR-binding domain to which additional peptides or proteins or other functional groups are coupled N- or C-terminally or to any other residues (specifically or non-specifically) by means of chemical conjugation (using known organic chemistry methods).

The "additional amino acid residues" discussed above may also provide one or more polypeptide domains with any desired function, such as the same binding function as the first, EGFR-binding domain, or another binding function, or an enzymatic function, toxic function (e.g. an immunotoxin), or a fluorescent signalling function, or combinations thereof.

The polypeptide of the invention may be in monomeric or multimeric forms. Multimeric forms of the polypeptide may be advantageous in that they may have enhanced binding properties. Preferred multimeric forms include dimeric, and trimeric forms. Multimeric forms of the polypeptides may comprise a suitable number of polypeptides of the invention. These polypeptides essentially form domains within the multimer. These domains may all have the same amino acid sequence, but alternatively, they may have different amino acid sequences. The polypeptides may be joined by covalent coupling using known organic chemistry methods, or expressed as one or more fusion polypeptides in a system for recombinant expression of polypeptides, or joined in any other fashion, either directly or via a linker, for example an amino acid linker.

Additionally, fusion polypeptides, in which the EGFR-binding polypeptide of the invention provides a first domain or moiety, and second or further moieties have other functions than binding EGFR are also contemplated and within the scope of the present invention. The second or further moieties of such a fusion polypeptide may comprise a binding domain with an affinity for another target molecule than EGFR. Such a binding domain may be another, similar polypeptide binder. For example, the polypeptide binder may be a Z variant. This makes it possible to create multi-specific reagents that may be used in several types of applications such as medicine, veterinary medicine, diagnosis, separation, and imaging. The preparation of such multi-specific fusion polypeptides may be performed as generally described above.

In other embodiments of the invention, the second or further moieties may comprise an unrelated, naturally occurring or recombinant protein (or a fragment thereof which retains the binding or other ability of the naturally-occurring or recombinant protein) having a binding affinity for a target. For example, an EGFR-binding polypeptide in accordance with the invention may be joined to an albumin-binding domain of streptococcal protein G, or any other protein/peptide with affinity for a serum protein to improve the half-life of the EGFR-binding polypeptide for use in therapeutic applications.

The EGFR-binding polypeptides of the present invention may be provided in the form of other fusion polypeptides. For example the EGFR-binding polypeptide, or fragment thereof, may be covalently coupled to a second or further moiety or moieties, which in addition to, or instead of target binding, exhibit other functions. One example would be a fusion between one or more EGFR-binding polypeptides and an enzymatically active polypeptide serving as a reporter or effector moiety. Examples of reporter enzymes, which may be coupled to the EGFR-binding polypeptide to form a fusion protein, are well-known to the skilled person and include enzymes such as β-galactosidase, alkaline phosphatase, horseradish peroxidase, carboxypeptidase. Other options for the second and further moiety or moieties of a fusion polypeptide according to the invention include fluorescent polypeptides, such as green fluorescent protein, red fluorescent protein, luciferase and variants thereof.

Other options for the second and further moiety or moieties of a fusion polypeptide according to the invention include a moiety or moieties for therapeutic applications. In therapeutic applications, other molecules can also be coupled, covalently or non-covalently, to the EGFR-binding polypeptide of the invention by other means. For example, other molecules such as enzymes for "ADEPT" (Antibody-Directed Enzyme Prodrug Therapy) applications using the polypeptide of the invention to direct the effector enzyme (e.g. carboxypeptidase) or RNase or DNase fusions; proteins for recruitment of effector cells and other components of the immune system; cytokines, such as IL-2, IL-12, TNFα, IP-10; pro coagulant factors, such as tissue factor, von Willebrand factor; toxins, such as ricin A, *Pseudomonas* exotoxins, calcheamicin, maytansinoid, toxic small molecules, such as auristatin analogues, doxorubicin.

The above-described additional amino acids (particularly hexahistidine, cysteine) can be used to couple chelators for radio-isotopes to the EGFR-binding polypeptides in order to readily incorporate radionuclides for diagnosis (such as $^{68}$Ga, $^{76}$Br, $^{111}$In, $^{99}$Tc, $^{125}$I) or therapy (e.g. $^{90}$Y, $^{131}$I, $^{211}$At, $^{177}$Lu).

The invention also embraces polypeptides in which the EGFR-binding polypeptide described above has been provided with a label group, such as at least one fluorophore, biotin or radioactive isotope, for example for the purposes of detection of the polypeptide.

With regard to the description above of fusion polypeptides and proteins incorporating an EGFR-binding polypeptide of the invention, it should be noted that the designation of first, second and further moieties is made for the purposes of clarity to distinguish between the EGFR-binding moiety or moieties on the one hand, and moieties exhibiting other functions on the other hand. These designations are not intended to refer to the actual order of the different domains in the polypeptide chain of the fusion protein or polypeptide. Thus, for example, a first moiety may be appear at the N-terminal end, in the middle, or at the C-terminal end of the fusion protein or polypeptide.

Further preferred aspects and embodiments of the invention will be apparent from the following listing of embodiments and the appended claims.

All scientific articles and patent documents referred to in the present description are incorporated herein by reference.

EMBODIMENTS OF THE PRESENT INVENTION

1. An EGFR-binding polypeptide comprising an amino acid sequence derived from the amino acid sequence: VDNKFNK EQQNAFYEILH LPNLNE EQRNAFIQSLKD DPSQ SANLLAEAKKLNDA QAPK by comprising amino acid substitutions at any or all of positions 9 to 11, 13 to 14, 17 to 18, 24 to 25, 27 to 28, 32 and 35 of the above sequence, or positions corresponding to those positions, which substitutions improve binding of the polypeptide to EGFR compared to a polypeptide comprising the unmodified amino acid sequence, in which the EGFR-binding polypeptide binds to EGFR such that the $K_D$ value of the interaction is at most 10 µM.
2. An EGFR-binding polypeptide according to embodiment 1 in which the amino acid substitution at position 9 is a hydrophobic amino acid.
3. An EFGR-binding polypeptide according to embodiment 1 or 2 in which the amino acid substitution at position 9 is a non-polar amino acid.
4. An EGFR-binding polypeptide according to any one of embodiments 1 to 3 in which the amino acid substitution at position 9 has an aliphatic R group.
5. An EGFR-binding polypeptide according to any one of embodiments 1 to 4 in which the amino acid substitution at position 9 has an aromatic R group.
6. An EGFR-binding polypeptide according to any one of embodiments 1 to 2 or 4 or 5 in which the amino acid substitution at position 9 is a polar amino acid.
7. An EGFR-binding polypeptide according to any one of embodiments 1 to 5 in which the amino acid substitution at position 9 is uncharged.
8. An EGFR-binding polypeptide according to any one of embodiments 1 to 7 in which the amino acid substitution at position 9 is a basic amino acid.
9. An EGFR-binding polypeptide according to any one of embodiments 1 to 8 in which the amino acid substitution at position 9 is selected from W, M, T, F, H, S, L, A and V.
10. An EGFR-binding polypeptide according to embodiment 3 in which the amino acid substitution at position 9 is M, F, L, or V.
11. An EGFR-binding polypeptide according to any preceding embodiment in which the amino acid substitution at position 10 is a hydrophobic amino acid.
12. An EGFR-binding polypeptide according to any preceding embodiment in which the amino acid substitution at position 10 is a hydrophilic amino acid.
13. An EGFR-binding polypeptide according to any one of embodiments 1 to 11 in which the amino acid substitution at position 10 is neutral.
14. An EGFR-binding polypeptide according to any preceding embodiment in which the amino acid substitution at position 10 is a polar amino acid
15. An EGFR-binding polypeptide according to any one of embodiments 1 to 13 in which the amino acid substitution at position 10 is a non-polar amino acid.
16. An EGFR-binding polypeptide according to any preceding embodiment in which the amino acid substitution at position 10 is an acidic amino acid.
17. An EGFR-binding polypeptide according to any preceding embodiments in which the amino acid substitution at position 10 is selected from S, L, G, Y, A, E, W, and Q.
18. An EGFR-binding polypeptide according to embodiment 17, in which the amino acid substitution at position 10 is L, Y, E, or Q.
19. An EGFR-binding polypeptide according to any preceding embodiment, in which the amino acid substitution at position 11 is hydrophobic.
20. An EGFR-binding polypeptide according to any one of embodiments 1 to 18, in which the amino acid substitution at position 11 is neutral.
21. And EGFR-binding polypeptide according to any one of embodiments 1 to 19 in which the amino acid substitution at position 11 is hydrophilic.
22. An EGFR-binding polypeptide according to any preceding embodiment, in which the amino acid substitution at position 11 is a non-polar amino acid.
23. An EGFR-binding polypeptide according to embodiment 22 in which the amino acid substitution at position 11 has an aliphatic R group.
24. An EGFR-binding polypeptide according to any preceding embodiment in which the amino acid substitution at position 11 has a positively charged R group.
25. An EGFR-binding polypeptide according to any preceding embodiment in which the amino acid substitution at position 11 is a basic amino acid.

26. An EGFR-binding polypeptide according to any one of embodiments 1 to 21 in which the amino acid at position 11 is a polar amino acid.
27. An EGFR-binding polypeptide according to any one of embodiments 1 to 23 in which the amino acid at position 11 is uncharged.
28. An EGFR-binding polypeptide according to any one preceding embodiments in which the amino acid substitution at position 11 is selected from A, I, K, P, and N.
29. An EGFR-binding polypeptide according to embodiment 28 in which the amino acid substitution at position 11 is A, I, or K.
30. An EGFR-binding polypeptide according to any preceding embodiment in which the amino acid substitution at position 13 is hydrophobic.
31. An EGFR-binding polypeptide according to any preceding embodiment in which the amino acid substitution at position 13 is non-polar.
32. An EGFR-binding polypeptide according to any preceding embodiment in which the amino acid substitution at position 13 has an aliphatic R group.
33. An EGFR-binding polypeptide according to any one of embodiments 1 to 30 in which the amino acid substitution at position 13 is polar.
34. An EGFR-binding polypeptide according to any preceding embodiment in which the amino acid substitution at position 13 is uncharged.
35. An EGFR-binding polypeptide according to any preceding embodiment in which the amino acid substitution at position 13 has an aromatic R group.
36. An EGFR-binding polypeptide according to any preceding embodiment in which the amino acid substitution at position 13 is selected from A, S, V, M, I, Y, W and T.
37. An EGFR-binding polypeptide according to embodiment 8 in which the amino acid substitution at position 13 is M, I, Y, or V.
38. An EGFR-binding polypeptide according to any preceding embodiment in which the amino acid at position 14 is hydrophilic.
39. An EGFR-binding polypeptide according to any one of embodiments 1 to 37 in which the amino acid substitution at position 14 is neutral.
40. An EGFR-binding polypeptide according to any preceding embodiment in which the amino acid substitution at position 14 is polar.
41. An EGFR-binding polypeptide according to embodiment 40 in which the amino acid substitution at position 14 is uncharged.
42. An EGFR-binding polypeptide according to any preceding embodiment in which the amino acid substitution at position 14 is acidic.
43. An EGFR-binding polypeptide according to any one of embodiments 1 to 41 in which the amino acid substitution at position 14 is basic.
44. An EGFR-binding polypeptide according to any one of embodiments 1 to 39 in which the amino acid substitution at position 14 is non-polar.
45. An EGFR-binding polypeptide according to embodiment 44 in which the amino acid substitution at position 14 has an aliphatic R group.
46. An EGFR-binding polypeptide according to any preceding embodiment in which the amino acid substitution at position 14 has a negatively charged R group.
47. An EGFR-binding polypeptide according to any preceding embodiment in which the amino acid substitution at position 14 is selected from S, E, R, T, W, V, N, T and A.
48. An EGFR-binding polypeptide according to embodiment 47 in which the amino acid substitution at position 14 is S or T.
49. An EGFR-binding polypeptide according to any preceding embodiment in which the amino acid substitution at position 17 is neutral.
50. An EGFR-binding polypeptide according to any one of embodiments 1 to 48 in which the amino acid substitution at position 17 is hydrophilic.
51. An EGFR-binding polypeptide according to any one of embodiments 1 to 48 in which the amino acid substitution at position 17 is hydrophobic.
52. An EGFR-binding polypeptide according to any preceding embodiment in which the amino acid substitution at position 17 is polar.
53. An EGFR-binding polypeptide according to embodiment 52 in which the amino acid substitution at position 17 is uncharged.
54. An EGFR-binding polypeptide according to any one of embodiments 1 to 52 in which the amino acid at position 17 is positively charged.
55. An EGFR-binding polypeptide according to any one of embodiments 1 to 51 in which the amino acid substitution at position 17 is non-polar.
56. An EGFR-binding polypeptide according to embodiment 55 in which the amino acid at position 17 has an aliphatic R group.
57. An EGFR-binding polypeptide according to any preceding embodiment in which the amino acid at position 17 is basic.
58. An EGFR-binding polypeptide according to any preceding embodiment in which the amino acid substitution at position 17 is selected from: S, G, N, and V.
59. An EGFR-binding polypeptide according to embodiment 12 in which the amino acid substitution at position 17 is selected from G, N, and V.
60. An EGFR-binding polypeptide according to embodiment in which the amino acid at position 18 is neutral.
61. An EGFR-binding polypeptide according to any one of embodiments 1 to 59 in which the amino acid substitution at position 18 is hydrophilic.
62. An EGFR-binding polypeptide according to any preceding embodiment in which the amino acid substitution at position 18 is non-polar.
63. An EGFR-binding polypeptide according to any one of embodiments 1 to 61 in which the amino acid substitution at position 18 is polar.
64. An EGFR-binding polypeptide according to any preceding embodiment in which the amino acid substitution at position 18 is uncharged.
65. An EGFR-binding polypeptide according to any one of embodiments 1 to 63 in which the amino acid substitution at position 18 is positively charged.
66. An EGFR-binding polypeptide according to any preceding embodiment in which the amino acid substitution at position 18 is acidic.
67. An EGFR-binding polypeptide according to any one of embodiments 1 to 65 in which the amino acid substitution at position 18 is basic
68. An EGFR-binding polypeptide according to any preceding embodiment in which the amino acid substitution at position 18 is selected from G, S, D, R, N, H, E and K.
69. An EGFR-binding polypeptide according to embodiment 68 in which the amino acid substitution at position 18 is R or N.

70. An EGFR-binding polypeptide according to any preceding embodiment in which the amino acid substitution at position 24 is hydrophobic.
71. An EGFR-binding polypeptide according to any one of embodiments 1 to 69 in which the amino acid substitution at position 24 is neutral.
72. An EGFR-binding polypeptide according to any preceding embodiment in which the amino acid substitution at position 24 is basic.
73. An EGFR-binding polypeptide according to any preceding embodiment in which the amino acid substitution at position 24 is non-polar.
74. An EGFR-binding polypeptide according to embodiment 73 in which the amino acid substitution at position 24 has an aliphatic R group.
75. An EGFR-binding polypeptide according to any one of embodiments 1 to 72 in which the amino acid substitution at position 24 is polar.
76. An EGFR-binding polypeptide according to any preceding embodiment in which the amino acid at position 24 has an aromatic R group.
77. An EGFR-binding polypeptide according to any preceding embodiment in which the amino acid substitution at position 24 is selected from K, W, N, G, L, R and M.
78. An EGFR-binding polypeptide according to embodiment 77 in which the amino acid substitution at position 24 is V or G.
79. An EGFR-binding polypeptide according to any preceding embodiment in which the amino acid substitution at position 25 is neutral.
80. An EGFR-binding polypeptide according to embodiment in which the amino acid substitution at position 25 is hydrophobic.
81. An EGFR-binding polypeptide according to any preceding embodiment in which the amino acid substitution at position 25 is non-polar.
82. An EGFR-binding polypeptide according to embodiment 81 in which the amino acid substitution at position 25 has an aliphatic R group.
83. An EGFR-binding polypeptide according to any preceding embodiment in which the amino acid substitution at position 35 has an aromatic R group.
84. An EGFR-binding polypeptide according to any one of embodiments 1 to 80 in which the amino acid at position 25 is polar.
85. An EGFR-binding polypeptide according to any preceding embodiment in which the amino acid substitution at position 25 is basic.
86. An EGFR-binding polypeptide according to any preceding embodiment in which the amino acid substitution at position 25 is selected from L, G, W, V, S, H, and W.
87. An EGFR-binding polypeptide according to embodiment 86 in which the amino acid substitution at position 25 is G or W.
88. An EGFR-binding polypeptide according to any preceding embodiment in which the amino acid substitution at position 27 is hydrophilic.
89. An EGFR-binding polypeptide according to any one of embodiments 1 to 88 in which the amino acid substitution at position 27 is hydrophobic.
90. An EGFR-binding polypeptide according to any one of embodiments 1 to 88 in which the amino acid substitution at position 27 is neutral.
91. An EGFR-binding polypeptide according to any preceding embodiment in which the amino acid substitution at position 27 is non-polar.
92. An EGFR-binding polypeptide according to any preceding embodiment in which the amino acid substitution at position 27 is acidic.
93. An EGFR-binding polypeptide according to any one of embodiments 1 to 90 in which the amino acid substitution at position 27 is polar.
94. An EGFR-binding polypeptide according to embodiment 93 in which the amino acid substitution at position 27 is uncharged.
95. An EGFR-binding polypeptide according to any one of embodiments 1 to 91 in which the amino acid substitution at position 27 is basic.
96. An EGFR-binding polypeptide according to any one of embodiments 1 to 93 in which the amino acid substitution at position 27 has a negatively charged R group.
97. An EGFR-binding polypeptide according to any preceding embodiment in which the amino acid substitution at position 27 is selected from A, E, F, M, L, C, K, G, and S.
98. An EGFR-binding polypeptide according to embodiment 97 in which the amino acid substitution at position 27 is E, M, or S.
99. An EGFR-binding polypeptide according to any preceding embodiment in which the amino acid substitution at position 28 is neutral.
100. An EGFR-binding polypeptide according to any one of embodiments 1 to 98 in which the amino acid substitution at position 28 is hydrophobic.
101. An EGFR-binding polypeptide according to any preceding embodiment in which the amino acid substitution at position 28 is non-polar.
102. An EGFR-binding polypeptide according to embodiment 101 in which the amino acid substitution at position 28 has an aliphatic R group.
103. An EGFR-binding polypeptide according to embodiment in which the amino acid substitution at position 28 is polar.
104. An EGFR-binding polypeptide according to embodiment 103 in which the amino acid substitution at position 28 is uncharged.
105. An EGFR-binding polypeptide according to any preceding embodiment in which the amino acid substitution at position 28 is basic.
106. An EGFR-binding polypeptide according to any preceding embodiment in which is the amino acid substitution at position 28 is selected from F, Q, V, A, K, V and T.
107. An EGFR-binding polypeptide according to embodiment 106 in which the amino acid substitution at position 28 is T, Q or V.
108. An EGFR-binding polypeptide according to any preceding embodiment in which the amino acid substitution at position 32 is hydrophobic.
109. An EGFR-binding polypeptide according to any preceding embodiment in which the amino acid substitution at position 32 is neutral.
110. An EGFR-binding polypeptide according to any preceding embodiment in which the amino acid substitution at position 32 is non-polar.
111. An EGFR-binding polypeptide according to embodiment 110 in which the amino acid at position 32 has an aliphatic R group.
112. An EGFR-binding polypeptide according to any one of embodiments 1 to 109 in which the amino acid substitution at position 32 is polar.
113. An EGFR-binding polypeptide according to embodiment 112 in which the amino acid substitution at position 32 is uncharged.

114. An EGFR-binding polypeptide according to any preceding embodiment in which the amino acid substitution at position 32 is basic.
115. An EGFR-binding polypeptide substitution according to any preceding embodiment in which the amino acid substitution at position 32 is selected from V, L, S, F, A and R.
116. An EGFR-binding polypeptide according to embodiment 115 in which the amino acid substitution at position 32 is L, S, or A.
117. An EGFR-binding polypeptide according to any preceding embodiment in which the amino acid substitution at position 35 is hydrophobic.
118. An EGFR-binding polypeptide according to any one of embodiments 1 to 116 in which the amino acid substitution at position 35 is neutral.
119. An EGFR-binding polypeptide according to any preceding embodiment in which the amino acid substitution at position 35 is non-polar.
120. An EGFR-binding polypeptide according to embodiment 119 in which the amino acid substitution at position 35 has an aliphatic R group.
121. An EGFR-binding polypeptide according to any one of embodiments 1 to 118 in which the amino acid substitution at position 35 is polar.
122. An EGFR-binding polypeptide according to embodiment 121 in which the amino acid substitution at position 35 is uncharged.
123. An EGFR-binding polypeptide according to any preceding embodiment in which the amino acid substitution at position 35 is basic.
124. An EGFR-binding polypeptide according to any preceding embodiment in which the amino acid substitution at position 35 has an aromatic R group.
125. An EGFR-binding polypeptide according to any preceding embodiment in which the amino acid substitution at position 35 is selected from V, W, S, R, M, H, and L.
126. An EGFR-binding polypeptide according to embodiment 125 in which the amino acid substitution at position 35 is W, S or V.
127. An EGFR-binding polypeptide according to any preceding embodiment in which amino acid residues located on the surface of the polypeptide are substituted.
128. An EGFR-binding polypeptide according to any preceding embodiment in which amino acid residues within the core of the polypeptides three-dimensional structure are not substituted.
129. An EGFR-binding polypeptide according to any preceding embodiment which has been extended by C terminal and/or N terminal amino acid extensions.
130. An EGFR-binding polypeptide according to embodiment 129 in which the or each amino acid extension enhances binding of EGFR by the polypeptide.
131. An EGFR-binding polypeptide according to embodiment 129 or 130 in which the or each amino acid extension improves production, purification, stabilization in vivo or in vitro, coupling, or detection of the polypeptide.
132. An EGFR-binding polypeptide according to embodiment 131 in which the or each amino acid extension includes a cysteine residue at the first or last position in the amino sequence of the polypeptide.
133. An EGFR-binding polypeptide according to embodiment 131 in which the amino acid residue extension comprises a $His_6$ tag, or a "myc" or a "flag" tag.
134. An EGFR-binding polypeptide according to embodiment 131 in which the extension comprises an albumin-binding domain of streptococcal protein G, or a derivative thereof, which improves the half life of the EGFR-binding polypeptide in therapeutic applications.
135. An EGFR-binding polypeptide according to any preceding embodiment comprising about 53 amino acids.
136. An EGFR-binding polypeptide according to any preceding embodiment which binds to EGFR such that the $K_D$ value of the interaction is at most $1 \times 10^{-6}$ M.
137. An EGFR-binding polypeptide according to embodiment 136 which binds to EGFR such that the $K_D$ value of the interaction is at most $1 \times 10^{-7}$ M.
138. An EGFR-binding polypeptide according to any preceding embodiment which binds to the extra-cellular domain of EGFR.
139. An EGFR-binding polypeptide according to embodiment 138 which binds to a portion of the extra-cellular domain of EGFR (SEQ ID NO:329) corresponding to nucleotides 259-2127 of the mature EGFR (SEQ ID NO:328).
140. An EGFR-binding polypeptide comprising a fragment of an EGFR-binding polypeptide according to any preceding embodiment.
141. An EGFR-binding polypeptide according to embodiment 140 in which the fragment comprises an N terminal reduction of a polypeptide according to any one of embodiments 1 to 139.
142. An EGFR-binding polypeptide according to embodiment 141 in which the N terminal reduction is by up to four amino acids.
143. An EGFR-binding polypeptide according to any preceding embodiment in multimeric form comprising EGFR-binding polypeptide units.
144. An EGFR-binding polypeptide according to embodiment 143 in which the EGFR-binding polypeptide monomer units are covalently coupled together.
145. An EGFR-binding polypeptide according to embodiment 143 in which the EGFR-binding polypeptide monomer units are expressed as a fusion protein.
146. An EGFR-binding polypeptide according to any one of embodiments 143 to 145 in a dimeric form.
147. A nucleotide encoding a polypeptide according to any preceding embodiment.
148. A method of producing a polypeptide according to any one of embodiments 1 to 146 the method comprising expressing a nucleotide according to embodiment 147.
149. A combination of an EGFR-binding polypeptide according to any one of embodiments 1 to 146, and a detectable agent.
150. A combination according to embodiment 149, in which the detectable agent is a radioactive substance for use in radio-imaging.
151. A combination according to embodiment 150 in which the radioactive substance is a radionuclide.
152. A combination according to embodiment 149 in which the detectable agent is an enzyme.
153. A combination according to embodiment 152 in which the enzyme is selected from β-galactosidase, alkaline phosphatase, horseradish peroxidase, and a carboxypeptidase.
154. A combination according to embodiment 149 in which the detectable agent is a fluorescent polypeptide.
155. A combination of an EGFR-binding polypeptide according to any one of embodiments 1 to 146, and a therapeutic agent.
156. A combination according to any one of embodiments 149 to 155 in which the EGFR-binding polypeptide and detectable agent or therapeutic agent are covalently coupled together.

157. A combination according to any one of embodiments 149 to 155 in which the EGFR polypeptide and detectable agent or therapeutic agent are expressed as a fusion protein.
158. A method of radio-imaging in which a combination according to any one of embodiments 150 to 151 is used as a radio-imaging agent.
159. A method of detection of EGFR, comprising providing a sample suspected to contain an EGFR, contacting the sample with an EGFR-binding polypeptide according to any one of embodiments 1 to 146, or a combination according to any one of embodiments 149 to 154 and detecting binding of the polypeptide or combination to indicate the presence of an EGFR in the sample.
160. A method of detection according to embodiment 159 in which more than one EGFR is detected.
161. A method of separating or capturing EGFR from a sample, the method comprising contacting the sample with an EGFR-binding polypeptide according to any one of embodiments 1 to 146 or a combination according to any one of embodiments 149 to 154 whereby EGFR binds to the polypeptide and can be removed from the sample.
162. A diagnostic method, for determining the presence of an EGFR in a subject, the method including contacting the subject, or a sample derived from the subject, with an EGFR-binding polypeptide according to any one of embodiments 1 to 146, or a combination according to any one of 149 to 154 and detecting binding of the polypeptide or combination.
163. A method according to embodiment 162 in which the subject is human or animal.
164. A method according to embodiment 162 in which the method is performed in vivo.
165. A method according to embodiment 162 or 163 in which the method is performed on a sample in vitro.
166. A method of treatment of an EGFR-related condition in a subject or in material derived from a subject, in which the subject or material is treated with an EGFR-binding polypeptide according to any one of embodiments 1 to 146 or a combination according to any one of embodiments 155 to 157.
167. A method of treatment according to embodiment 166 in which binding of an EGFR-binding polypeptide according to any one of embodiments 1 to 146 or a combination according to any one of embodiments 155 to 157 to an EGFR of the subject, or in the material, inhibits or stimulates activation of the receptor.
168. A method of treatment according to embodiment 166 or 167 in which binding of the EGFR-binding polypeptide to an EGFR of the subject, or in the material, inhibits cell signalling.
169. A method of treatment according to any one of embodiments 166 to 168, in which the EGFR-related condition is a cancer.
170. A method of treatment according to embodiment 169 in which the cancer is selected from lung, breast, prostate, colon, ovary, head and neck cancers.
171. A method according to any one of embodiments 166 to 170 in which subject is human or animal.

BRIEF DESCRIPTION OF THE DRAWINGS

Polypeptides in accordance with the invention and methods for their use will now be described, by way of example only, with reference to the accompanying drawings, FIGS. 1-12, in which:

FIG. 1 is a listing of the amino acid sequences of examples of EGFR binding motifs comprised in EGFR-binding polypeptides of the invention (SEQ ID NO:1-163), examples of EGFR-binding polypeptides according to the invention (SEQ ID NO:164-326), the protein Z derivative of domain B of Staphylococcus aureus protein A (SEQ ID NO:327), entire human EGFR (SEQ ID NO:328) and the extracellular domain of human EGFR (SEQ ID NO:329);

FIG. 2A shows the amino acid sequences of different EGFR-binding polypeptides according to the invention selected in Example 1 compared to the protein Z sequence. The figure indicates basic, acidic, non-polar and polar amino acid residues; FIG. 2B shows the amino acid sequence of four polypeptides from FIG. 2A and indicates hydrophobic, neutral and hydrophilic amino acid residues, FIG. 2C shows the amino acid sequences of the polypeptides of FIG. 2B with other characteristics highlighted, and FIG. 2D illustrates an affinity maturation strategy for producing polypeptides according to the invention;

Figure 3:
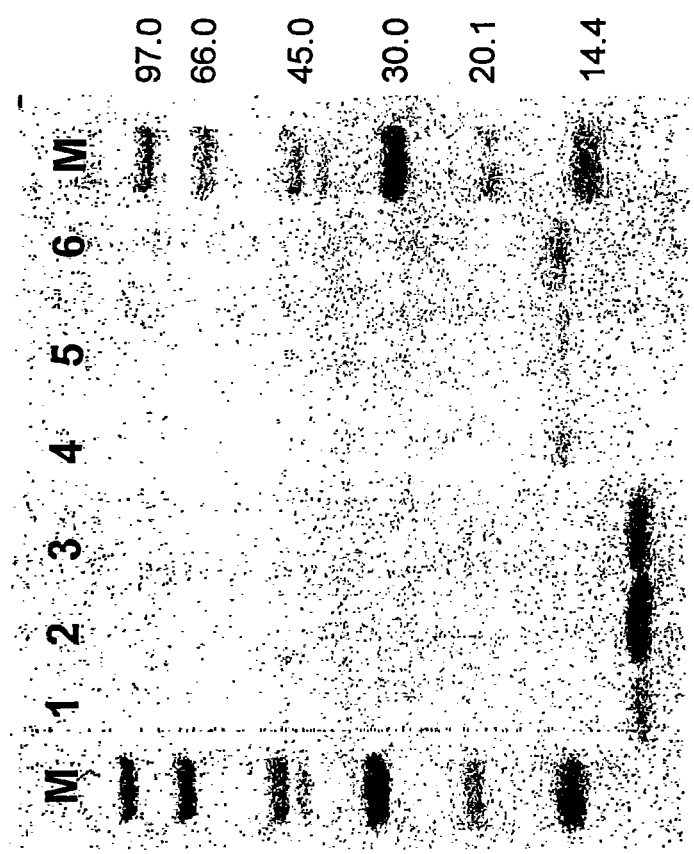
FIG. 3 shows the result of SDS-PAGE analysis of EGFR-binding polypeptides $His_6$-$Z_{EGFR:942}$ (lane 1), $His_6$-$Z_{EGFR:948}$ (lane 2), $His_6$-$Z_{EGFR:955}$ (lane 3), $His_6$-$(Z_{EGFR:942})_2$ (lane 4), $His_6$-$(Z_{EGFR:948})_2$ (lane 5), and $His_6$-$(Z_{EGFR:955})_2$ (lane 6). Lane M contains marker proteins. To the right, molecular mass is given in kilodaltons.

In the following experiments, phage display was used to select EGFR-binding variants of protein Z derived from the B domain of Staphylococcus aureus protein A. The EGFR-binding Z variants are sometimes collectively denoted $Z_{EGFR}$. Each individual Z variant has been given a unique identification number #####, and individual variants are interchangeably referred to as Z##### and $Z_{EGFR:#####}$.

Example 1

First Selection of EGFR Binding Polypeptides According to the Invention

Materials and Methods
Production of Polypeptide Binders, Strains, Vectors, and Phagemid Library The amber suppressor *Escherichia coli* strain RRIΔM15 (Rüther, U. (1982) Nucleic Acids Res., 10, 5765-5772.) was used as bacterial host for phage production and cloning procedure. The phagemid vector pAffi1, and the construction of the phagemid library, Zlib2002 ($3 \times 10^9$ members), used in this study are disclosed in Gronwall C, Jonsson A, Lindström S, Gunneriusson E, Stahl S, Herne N: "Selection and characterization of Affibody ligands binding to Alzheimer amyloid beta peptides", J. Biotechnol. (2006) in press, Epub 27 Sep. 2006. Phagemid inserts of selected clones were sub-cloned into the expression vector pAY442 and pAY430, containing a T7 promoter (Studier et al., (1990) Methods Enzymol., 185, 60-89), a DNA fragment encoding a hexahistidyl ($His_6$) tag and a multiple cloning site, together with a gene conferring resistance to kanamycin, as well as an additional cysteine at the C-terminus for direct labeling for pAY430. The *E. coli* strain BL21(DE3) (Novagen, Madison, Wis.) was used for protein production from the expression vectors.

Preparation of Phage Stock

Preparation of phage stocks from the library (a portion of Zlib2002) and between selections was performed according to previously described procedures (Nord, K et al., (1997) Nat. Biotechnol., 15, 772-777; Hansson et al., (1999) Immunotechnology, 4, 237-252) using the helper phage M13K07 (New England Biolabs, Beverly, Mass.). PEG/NaCl precipitation yielded phage titres of about $10^{13}$ pfu/ml.

Phage Selections

A ~100 kDa recombinant extra-cellular domain (ECD) of EGFR comprising 623 amino acids, corresponding to nucleotides 259-2127, was used as the target protein during selections (SEQ ID NO:329). The protein was biotinylated in vitro using EZ-Link™-Sulfo-NHS-LC-Biotin (Pierce, Rockford, Ill.). A 20-fold molar excess of biotin was added to the EGFR-ECD in phosphate-buffered saline (PBS; 10 mM phosphate, 137 mM NaCl, pH 7.2), and the mixture was incubated at room temperature for 1 h. followed by extensive dialysis against PBS at 4° C. to remove the surplus biotin.

The biotinylated target protein was then immobilized on streptavidin-coated paramagnetic beads (Dynabeads M-280 Streptavidin; Dynal A. S., Oslo, Norway). For each round of selection, beads were washed twice with PBS supplemented with 0.1% Tween-20 (PBST). To avoid unspecific binders, all tubes used in this procedure were pre-treated with PBST supplemented with 0.1% gelatin. To further avoid binders against the streptavidin present on the paramagnetic beads, the phage stock in PBST supplemented with 0.1% gelatin was pre-incubated with 0.2 mg of the beads (previously washed twice with PBST) for round 1 and 2. The unbound phage stock was then subjected to biopanning against the EGFR-ECD target protein for 1 h 45 min at room temperature under continuous end-over-end rotation, followed by incubation with the streptavidin-coated paramagnetic beads for 15 min (room temperature, continuous end-over-end rotation). Two separate selections, with each two different decreasing target concentrations in each panning round were performed as follows. For round 1; 12 and 1.2 μg of target protein were incubated with 6 and 0.6 mg of beads, respectively, for round 2; 5, 2.5, 0.5, and 0.35 μg of target protein were incubated with 2.5, 1.25, 0.25, 0.125 mg of beads, respectively, and for rounds 3 and 4; 5, 1, 0.5, and 0.1 μg of target protein were incubated with 1, 0.5, 0.1, 0.05 mg of beads, respectively. This procedure resulted in an immobilization of ~2 μg of the target protein per mg of beads, as determined by SDS-PAGE analysis. The four rounds of biopanning were performed as follows. The beads were washed twice with PBST in round 1, five times in round 2, seven times in round 3 and 10 times in round 4. The bound phages were subsequently eluted with 500 μl of 50 mM glycine-HCl, pH 2.1, for 10 min at room temperature, followed by immediate neutralization with 50 μl of 1 M Tris-HCl, pH 8.0 and 450 μl PBS.

The eluted phages were used to infect log phase RRIΔM15 cells for 30 min at 37° C. The infected cell suspensions were spread on TYE agar plates (15 g/l agar, 8 g/l NaCl, 10 g/l tryptone and 6 g/l yeast extract), supplemented with 2% glucose and 100 mg/l ampicillin, and followed by overnight incubation at 37° C. The grown colonies were collected by re-suspension in tryptic soy broth (TSB, 30 g/l; Merck, Darmstadt, Germany), supplemented with 5 g/l yeast extract, 2% glucose and 100 μg/ml ampicillin, and a fraction (~500 times excess of cells compared to the phage titre after elution) was used for inoculation, leading to the next generation of phage stock. The selection process was monitored by titrating the phage stocks before selection and after elution. A serial dilution of phages was allowed to infect log phase RRIΔM15 cells for 5 min at room temperature, followed by plating on TYE agar plates, supplemented with 2% glucose and 100 μg/ml ampicillin, and overnight incubation at 37° C.

Streptavidin ELISA

After four rounds of biopanning, an ELISA was performed on 372 randomly picked colonies from all four selections, to exclude phagemid (pAffi1) inserts with streptavidin binding capacity. Cell lysates from the randomly picked colonies were incubated in pre-blocked (PBST supplemented with 2% dry milk) 96 well streptavidin coated plate (Nunc transparent, c96, 236001) for 1.5 hours at room temperature. As a primary antibody a rabbit IgG pan-anti-polypeptide-specific binder (1.5 hours, room temperature, continuous shake) and as secondary antibody a rabbit immunoglobulin-HRP were used (P0448 Daco Cytomatation; 1 hour, room temperature, continuous shake). The $A_{405nm}$ absorbency was measured with a Tecan Sunrise spectrophotometer after the addition of the substrate solution (Immunopure TMB; Pierce).

DNA Sequencing

DNA sequencing of phagemid (pAffi1) inserts was performed on non-streptavidin binding clones from the fourth round of panning, where 64 clones were from selection 1 and 2, and 32 from selection 3 and 4. Specific primers and Big Dye terminators (Amersham Biosciences, Uppsala, Sweden) were used and the Sanger fragments analyzed on a DNA sequencer ABI prism 3700 Analyzer (Applied Biosystems, Foster City, Calif.). Sub-cloned DNA fragments were verified by the same procedure.

After excluding sequences with amber stop codons (three), more than one cysteine (one), and sequences that have been found in selections to other targets (three), ten sequences were chosen to be further investigated. The respective amino acid sequences of these polypeptide binders is shown in FIG. 1 and disclosed in the sequence listing as SEQ ID NO:164-173. The deduced EGFR binding motif of these variants are presented as SEQ ID NO:1-10. The sequences of the selected variants are also presented in FIG. 2A. Specifically, in FIG. 2A, the amino acid sequence corresponding to the "wild-type" Z domain is aligned to the deduced amino acid sequences of the 10 different polypeptide binders selected against EGFR-ECD, the dashes used in that Figure, and elsewhere in this specification, represent an amino acid which is the same as the corresponding amino acid in the "wild-type" sequence. The 13 randomized amino acid residues (Q9, Q10, N11, F13, Y14, L17, H18, E24, E25, R27, N28, Q32, K35) are presented. Amino acid residues that occur at the same position in more than one of the variants are presented in bold. Horizontal bars indicate amino acid identities. Figures to the right represent the number of times each polypeptide binder was detected upon DNA sequencing of 372 colonies. The three α-helices in the wild-type Z domain are boxed.

FIG. 2B and FIG. 2C give further characteristics of the amino acid substitutions in the polypeptide binders of the invention. In the context of hydrophobicity/hydrophilicity, "neutral" means an amino acid which is relatively neither hydrophobic nor hydrophilic.

FIG. 2D illustrates a maturation strategy for improving the initially-determined polypeptide binders. In this connection, the residues at positions 9, 10, 11, 13, and 14 may be less important and subjected to substitutions, whereas for positions 17 and 18, asparagine and arginine are especially preferred although serine and histidine, which may be preferred for technical reasons, may also be produced and used for binding as a result of codon similarity. At position 35, valine and serine are preferred although for technical reasons, leucine and alanine may be particularly selected as well. For positions 24, 25, 27, 28 and 32, amino acids G, W, M, T, and A are contemplated respectively, although single substitutions at any of these sites may occur with retained binding EGFR-capacity of the molecules.

DNA Constructs

DNA fragments encoding different EGFR polypeptide binders were sub-cloned into the expression vectors pAY442 and pAY430. The fragments were amplified from the pAffi1 vector with specific primers introducing an AccI site both 3' and 5', and ligated into the pAY442 and pAY430 vectors, previously restricted with the same enzyme, and dephosphorylated using Calf Intestine Alkaline Phosphatase (CIAP; Fermentas). The amplified DNA fragments were purified with QIAuick PCR Purification Kit (Qiagen GmbH, Hilden, Germany) and hybridized prior to ligation with T4 DNA Ligase (New England Biolabs). The ligations resulted in expression vectors denoted pAY442-$Z_{EGFR:no}$ and pAY430-$Z_{EGFR:no}$, encoding the different polypeptide binders fused to an N-terminus His$_6$ tag, allowing purification by immobilized metal ion affinity chromatography (IMAC). All plasmid preparations were, after cultivation of transformed *E. coli* cells overnight, performed using QIAprep Spin Miniprep Kit (Qiagen GmbH) according to the manufacturer's instructions.

Protein Production and Purification

Selected polypeptide binders were expressed as His$_6$-tagged fusion proteins from the pAY442 and pAY430 plasmids in *E. coli* strain BL21(DE3).

Cells were inoculated in 5 ml of TSB medium (30 g/l Tryptic Soy Broth), containing 50 mg/l kanamycin, and grown in deep well plate overnight at 37° C. at ~150 rpm. Fresh TSB (5 ml), supplemented with 5 g/l yeast extract and 50 mg/l kanamycin, was inoculated with 20 µl of the overnight cultures and the cells were grown at 37° C. for 4 hours, when gene expression was induced by addition of isopropyl β-D-thiogalactoside (IPTG) to a final concentration of 1 mM. After overnight cultivation at 2.5° C., the cells were harvested by centrifugation (10000 g, 10 min) and lysated by freeze thawing (−80° C., 40 min). The cell pellets were subsequently re-suspended in urea buffer (8 M, pH 8.0). The HiS$_6$-$Z_{EGFR}$ fusion proteins were recovered by IMAC purification on Ni-NTA Superflow columns under denaturing conditions (Qiagen) using BR3000 robot. The bound proteins were eluted with low pH urea buffer (8 M, pH 4.5) and renaturation of the purified fusion protein was performed by changing the buffer to HBS (10 mM HEPES, 150 mM NaCl, 3.4 mM EDTA, 0.005% surfactant P20, pH 7.4) on NAP™-5 size exclusion chromatography columns (Amersham Biosciences). Protein concentration for the polypeptides was calculated from absorbance measurements at 280 nm, using the appropriate extinction coefficient for each protein. The purified polypeptides were further analyzed by SDS-PAGE on Phastgel™ Homogenous 20% gels using a Phast system (Amersham Biosciences, Uppsala, Sweden). Protein concentrations for selected $Z_{EGFR}$ variants were also determined by amino acid analysis (Aminosyraanalyscentralen, Uppsala, Sweden).

FIG. 3 shows SDS-PAGE analysis of the expressed and IMAC-purified EGFR-binding polypeptides His$_6$-$Z_{EGFR:942}$ (lane 1) His$_6$$Z_{EGFR:948}$ (lane 2), HiS$_6$-$Z_{EGFR:955}$ (lane 3), His$_6$-($Z_{EGFR:942}$)$_2$ (lane 4), His$_6$-($Z_{EGFR:948}$)$_2$ (lane 5), and His$_6$-($Z_{EGFR:955}$)$_2$ (lane 6). Lane M, marker proteins with molecular masses in kilodaltons.

Biosensor Analyses

A BIAcore® 2000 instrument (Biacore AB, Uppsala, Sweden) was used for real-time biospecific interaction (BIA) between selected polypeptide binders and the target protein. EGFR-ECD (diluted in 10 mM NaAc, pH 4.5) was immobilized (~2600 RU) on the carboxylated dextran layer of one flow-cell surface of a CM5 sensor chip (Biacore) by amine coupling, according to the manufacturer's instructions. Another flow-cell surface was activated and deactivated to be used as a reference surface, and HER2-ECD and human IgG (Amersham Biosciences, Uppsala, Sweden) were immobilized on separate flow-cell surfaces on the CM5 sensor chip, to serve as negative controls. Samples of all polypeptide binders under test were diluted in the running buffer HBS (10 mM HEPES, 150 mM NaCl, 3.4 mM EDTA, 0.005% surfactant P20, pH 7.4) and filtrated (0.45 µm; Millipore, Billerica, Mass.) before binding analysis were performed at 25° C. In a first experiment, ~1 µM of each polypeptide binder under test (diluted in HBS) was injected over all surfaces with a flow rate of 20 µl/min. An unrelated 53 amino acid polypeptide binder, having no affinity for EGFR, was used as negative control, and the natural ligand hEGF (Chemicon International, Temecula, Calif., USA) and commercial monoclonal antibody cetuximab (MERCK Darmstadt, Germany) as positive controls, were also injected. In a second experiment, the monomeric HiS$_6$-$Z_{EGFR}$ and dimeric His$_6$-($Z_{EGFR}$)$_2$ polypeptide binders were subjected to kinetic analysis, in which the proteins were injected over an EGFR-ECD surface at concentrations ranging from 0.00625 µM to 12.8 µM with a flow rate of 30 µl/min. The dissociation equilibrium constant ($K_D$), the association rate constant ($k_a$), and the dissociation rate constant ($k_D$) were calculated using BIAevaluation 3.2 software (Biacore), assuming a one-to-one binding. For the second experiment the samples were run in duplicates in random order, and after each injection the flow cells were regenerated by the injection of 10 mM HCl. The results of the biosensor ranking analyses are depicted in Table 1 and FIG. 4. Table 1 gives a comparison of kinetic parameters of the monovalent and bivalent EGFR-ECD binding polypeptide binders from biosensor analysis on BIAcore. The dimeric EFGR-binding polypeptide constructs were generated through a gene duplication strategy, produced and affinity purified as previously described in Steffen et al Cancer Biother. & Radiopharmaceuticals, 20, 239-248. An additional polypeptide, $Z_{EGFR:1239}$ (identified as a sequence-relative to $Z_{EGFR:955}$) was included after sequencing of additional clones, and data on its performance as monomer are disclosed. The dissociation equilibrium constant gives the following affinity ranking of the four $His_6$-$Z_{EGFR}$ polypeptide binders: $His_6$-$Z_{EGFR:1239}$<$His_6$-$Z_{EGFR:955}$<$His_6$-$Z_{EGFR:945}$<$His_6$-$Z_{EGFR:942}$.

TABLE 1

| EFGR-binding polypeptide | $K_D{}^a$ (nM) | $k_a{}^b$ (M$^{-1}$s$^{-1}$) | $k_d{}^c$ (s$^{-1}$) |
| --- | --- | --- | --- |
| $His_6$-$Z_{EGFR:942}$ | ~130 | ~3.0 × 10$^5$ | ~4.0 × 10$^{-2}$ |
| $His_6$-$(Z_{EGFR:942})_2$ | ~30 | ~6.0 × 10$^5$ | ~1.6 × 10$^{-2}$ |
| $His_6$-$Z_{EGFR:948}$ | ~180 | ~4.2 × 10$^5$ | ~7.7 × 10$^{-2}$ |
| $His_6$-$(Z_{EGFR:948})_2$ | ~40 | ~1.9 × 10$^5$ | ~8.1 × 10$^{-3}$ |
| $His_6$-$Z_{EGFR:955}$ | ~190 | ~6.2 × 10$^4$ | ~1.2 × 10$^{-2}$ |
| $His_6$-$(Z_{EGFR:955})_2$ | ~50 | ~4.8 × 10$^4$ | ~2.4 × 10$^{-3}$ |
| $His_6$-$Z_{EGFR:1239}$ | ~490 | ~1.9 × 10$^5$ | ~9.2 × 10$^{-2}$ |

$^a$Dissociation equilibrium constant
$^b$Association rate constant
$^c$Dissociation rate constant It can be seen that from this in vitro binding analysis, all four EGFR-binding polypeptides bound EGFR with rather high affinity and that they differed somewhat in their binding kinetics characteristics.

Figure 4A:
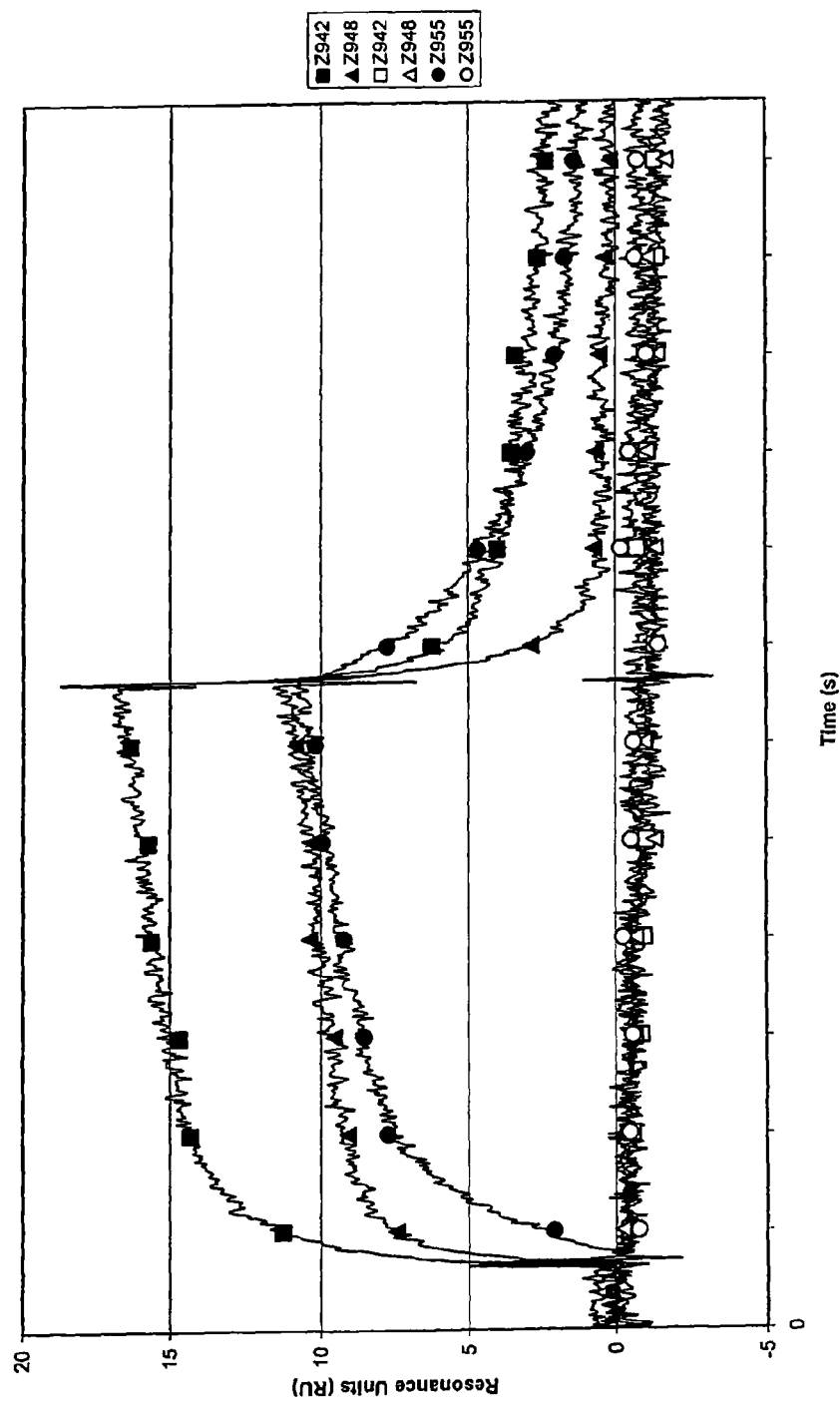
FIG. 4 shows the result of biosensor binding studies conducted using various EGFR-binding polypeptides according to the invention.

FIG. 4A shows the results of sensorgrams obtained after injection of the purified $His_6$-$(Z_{EGFR:942})_2$ (squares), $His_6$-$(Z_{EGFR:948})_2$ (triangles), and $His_6$ $(Z_{EGFR:955})_2$ (circles) variants over sensor chip flow-cell surfaces containing amine-coupled EGFR-ECD (filled square/triangles/circles) or HER2-ECD (open squares/triangles/circles). This demonstrates a specific binding of the three $His_6$-$Z_{EGFR}$ variants ($His_6$-$Z_{EGFR:942}$ $His_6$-$Z_{EGFR:945}$, and $His_6$-$Z_{EGFR:955}$) to the EGFR-ECD immobilized flow-cell surfaces, whereas no binding to the HER2-ECD immobilized flow-cell surface is seen.

Figure 4B:
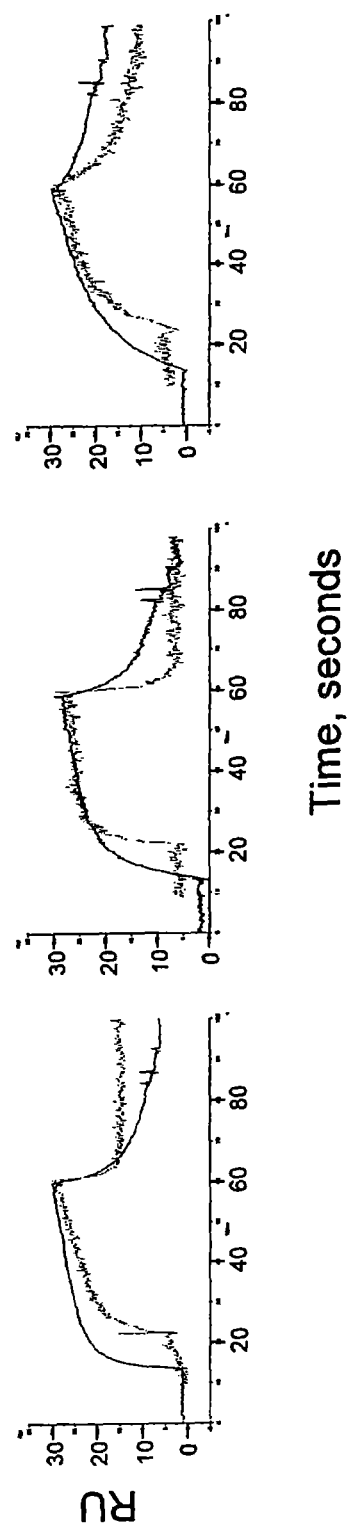

FIG. 4B shows the results of sensorgrams obtained after the injection of monovalent (lighter line) and bivalent (darker line) EGFR-binding polypeptides over an EGFR-ECD flow-cell surface. The diagram shows the three candidate binders, where the difference in off-rate between monovalent and bivalent EGFR-binding polypeptides is demonstrated, proving that the improvement of apparent affinity by avidity effect was achieved by primarily obtaining a slower off-rate in the second generation clones.

Cell Culture

For the Fluorophore Labeling FACS, and Confocal Microscope studies below, Human epithelial cancer cells A431 (European Collection of Cell Cultures, Wiltshire, UK), known to express ~2×10$^6$ EGFR per cell, were cultured in complemented medium, containing EMEM medium supplemented with 10% foetal calf serum, 2 mM L-glutamine, 1% non-essential amino acids, and 1% antibiotic-antimycotic, all from Gibco (Invitrogen AB). The cells were cultured at 37° C. in humidified air containing 5% $CO_2$.

Fluorophore Labeling $His_6$-$Z_{EGFR:942})_2$, $His_6$-$(Z_{EGFR:948})_2$, and $His_6$-$Z_{EGFR:955})_2$ polypeptide binders were labeled directly to the introduced cysteine (at C-terminus) with Oregon Green® 488 maleimide (Molecular Probes). Approximately 1 mg of $His_6$-$(Z_{EGFR})_2$ polypeptide binder was re-suspended in PBS and reduced with 20 mM DTT for 45 min at 37° C. Surplus DTT was removed on a NAP™-5 size exclusion column (Amersham Biosciences) equilibrated with PBS. A 10 mM solution of Oregon Green 488 maleimide was added at 20-fold molar excess and kept dark for 2 hours at room temperature with continuous shaking. Extensive dialysis against PBS was performed to remove excess fluorophore. The concentration and labeling performance of the fluorophore-labeled polypeptide binders under test were done by calculations according to manufacturer's protocol using absorbance measurements at 280 and 496 nm. The labeled polypeptide binders were also analyzed on an SDS-PAGE Phastgel™ Homogenous 20% gel using a Phast system (Amersham Biosciences).

FACS

The flow cytometric analyses were performed on a FACS Vantage SE stream-in-air flow cytometry instrument (BD Biosciences, San Jose, Calif., USA). The laser was aligned using flow cytometry alignment beads for 488 nm (Molecular Probes, Leiden, The Netherlands). Samples were illuminated with an air-cooled argon laser (488 nm). The fluorescence, the forward scattered and side scattered light from 10000 cells were detected at a rate of approximately 300 events s$^{-1}$. Flow cytometric data were analyzed with CellQuest software (BD Biosciences). Prior to flow cytometric analyses, cells seeded in Petri dishes ~3 days before experiment were trypsinated (0.25% Trypsin, 37° C., 10 min). The cells were centrifuged (582 g, 3 min) and the pellet re-suspended in PBS+1% BSA, and aliquoted at ~300000 cells per well in a 96 well plate. The cells were incubated with 10 µg/ml fluorophore-labeled $His_6$-$(Z_{EGFR})_2$ polypeptide binder for ~30 min on ice. After centrifugation and washing with PBS+1% BSA the cell pellet was re-suspended in 300 µl PBS+1% BSA and subjected to flow cytometric analysis. A similar ($His_6$-tagged dimeric construct) polypeptide having no binding capacity for EGFR was used as negative control.

Figure 5:
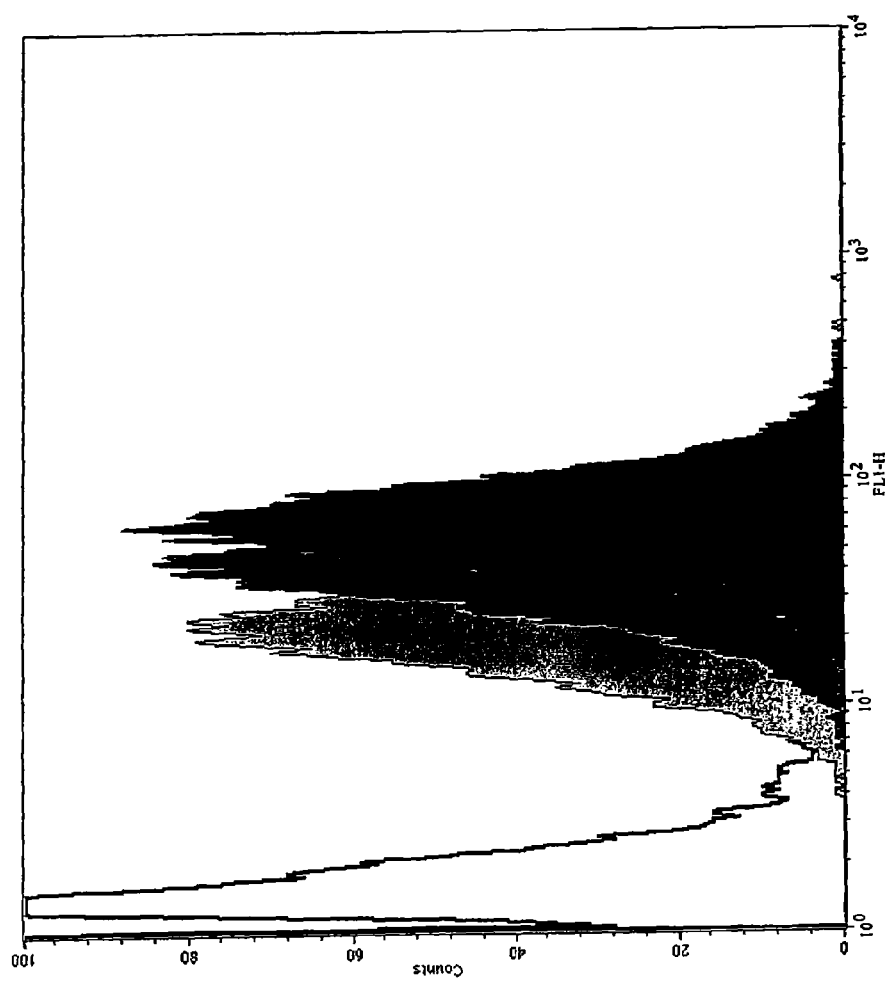
FIG. 5 shows the result of flow cytometric analysis of the affinity for native EGFR of three EGFR-binding polypeptides according to the invention.

The results of these studies are shown in FIG. 5. Specifically, FIG. 5 shows a flow cytometric analysis demonstrating a ranking of affinity for the three candidate binders ($His_6$-$(Z_{EGFR:942})_2$/$His_6$-$Z_{EGFR:948})_2$, $His_6$-$(Z_{EGFR:955})_2$) towards native EGFR on A431 cells. An unrelated Z variant molecule, used as a negative control (white), is positioned to the far left in the histogram. The three $Z_{EGFR}$ binders are then positioned in the order $His_6$-$Z_{EGFR:942})_2$ (light grey)<$His_6$-$(Z_{EGFR:948})_2$ (grey)<$His_6$-$(Z_{EGFR:955})_2$ (black). These data suggest that $Z_{EGFR:955}$ may be the best candidate of the three, in spite of its somewhat poorer affinity in BIAcore, since the assay is based on binding of native EGFR on cells.

Confocal Microscopy

Approximately 300000 A431 cells were seeded per 30 mm Petri dish the day before the experiment. The $His_6$-$(Z_{EGFR:942})_2$, $HiS_6$-$(Z_{EGFR:948})_2$, and $His_6$-$(Z_{EGFR:955})_2$ polypeptide binders under test were diluted to approximately 10 µg/ml in complete EMEM medium, added to separate Petri dishes and incubated in the dark for 2 hours at 37° C. The three polypeptide binders under test were also diluted as above in serum-free EMEM medium, added to separate Petri dishes and incubated in the dark 1 hour on ice. Following the incubation the cells were washed once with normal medium and some medium was added for image analysis in a confocal microscope (LSM 5 Pascal; Zeiss). Consecutive scans were performed to cover the thickness of the cell and a scan representing the middle of the cell was chosen. As a negative control, a similar polypeptide having no affinity for EGFR was analyzed in the same way.

Figure 6:
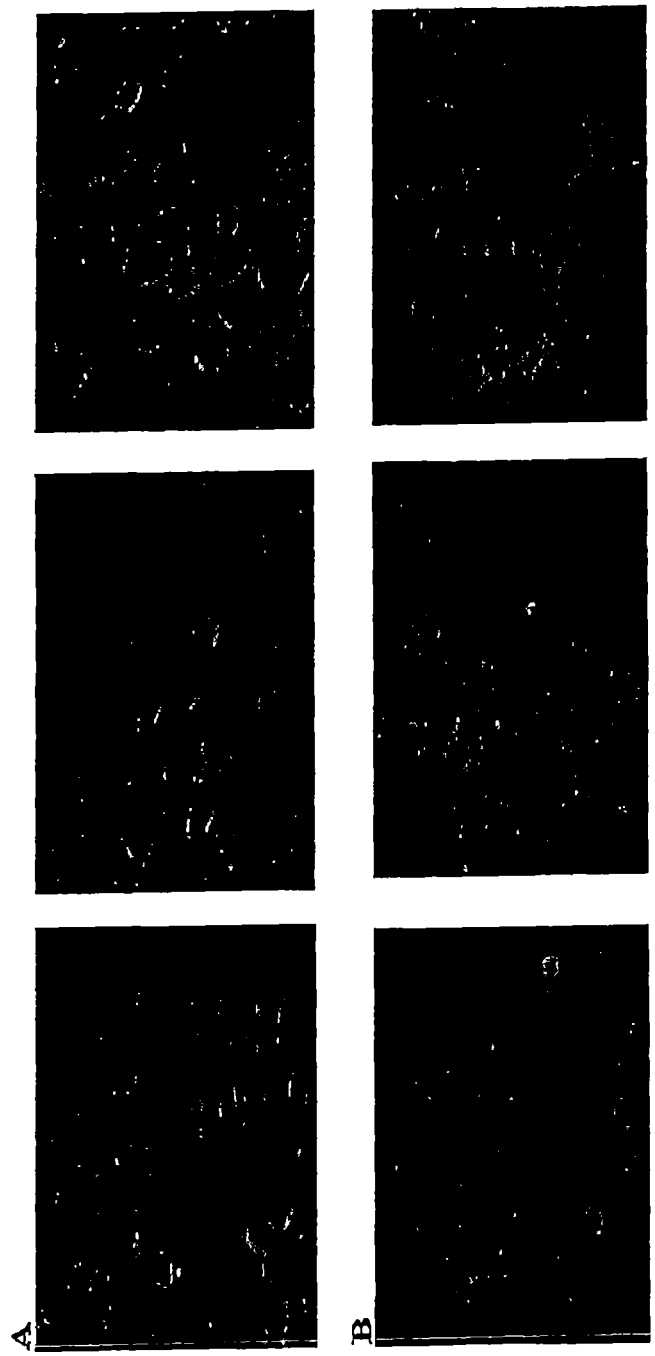
FIG. 6 is a series of confocal microscopy images of cells exposed to fluorophore-labeled EGFR-binding polypeptides according to the invention.

The results of the confocal microscopy are shown in FIG. 6. Specifically, FIG. 6 shows confocal microscopy images of A431 cells exposed to Oregon Green labeled $His_6$-$Z_{EGFR}$ polypeptide for A) 1 hour on ice and B) 2 hours in 37° C. From left to right, $His_6$-$(Z_{EGFR:942})_2$, $His_6$-$(Z_{EGFR:948})_2$, and $His_6$-$Z_{EFGR:955})_2$ are seen cell membrane bound in (A) and internalized in (B). The results demonstrate that the three EFGR-binding polypeptides seem, as expected, to bind to the cellular membrane, and that internalization seems to occur at incubation at 37° C.

Cell Culture

For the radio labeling, specificity and saturation studies below, cells were cultured in 75 cm$^2$ culture bottles and in 24-well plates (Nunclon surface, Denmark). For the labeling method, $^{125}$I (Amersham Biosciences, Uppsala, Sweden), acetic acid (Merck Darmstadt, Germany), chloramine-T 4Sigma, USA), sodium metabisulphite (Aldrich, USA) and N-succinimidyl-4-[tri-methylstannyl]benzoate (synthesized at our laboratory) were used. NAP-5 column (Sephadex G-25, Amersham Biosciences, Uppsala, Sweden) was applied for gel filtration. The cells were detached with Trypsin-EDTA (0.25/0.02%) (Biochrom Kg) and counted in a cell counter (Beckman Coulter Z2, Fullerton, Calif., USA). Radioactivity was measured with a gamma counter (1480 Wizard, Wallac Oy, Turku, Finland). The EGFR-rich squamous carcinoma cell line A431 (ATCC, CLR 1555, Rocksville, Md., USA) was used. The cells were cultured in Ham's F-10 medium supplemented with L-glutamine (2 mM Biochrom Kg, Berlin, Germany), PEST (penicillin 100 IU/ml and streptomycin 100 µg/ml) and 10% foetal calf serum (Biochrom Kg) ("complete medium"). The cells were grown at 37° C. in an incubator with humidified air equilibrated with 5% $CO_2$.

Radio-Labeling

Dimers of the polypeptide binders $Z_{EGFR:942}$, $Z_{EGFR:948}$ and $Z_{EFGR:955}$ were indirectly labeled with $^{125}$I via N-succinimidyl groups. Acetic acid (2 µl, 0.1% acetic acid in milli-Q) and N-succinimidyl-4-[tri-methylstannyl]benzoate (5 µl, 5% acetic acid in methanol) was added to the $^{125}$I (15 MBq). The iodine was coupled to the N-succinimidyl-4-[tri-methylstannyl]benzoate by adding 10 µl cloramine-T. The solution was then re-suspended for 30 seconds and further incubated at room temperature for 5 minutes. To stop the reaction, 15 µl sodium metabisulphite was added. The polypeptide binders were diluted in borate-buffer and added to the iodine solution and additional borate-buffer was added to a total volume of 150 µl, whereupon the solution was incubated for 30 minutes. To separate labeled polypeptide binders from low molecular weight compounds, a NAP-5 column equilibrated with PBS was used.

Specificity Test

A431 cells were cultured in 24-well plates and washed once with serum free Ham's F-10 medium. The three dimeric polypeptide binders being tested were labeled with $^{125}$I and added to the cells with a molar excess of approximately 10:1 in relation to the number of available receptors and incubated in 37° C. for 4 hours. In some wells unlabeled polypeptide binders (molar excess of approx. 500:1) were added together with [$^{125}$I]polypeptide binders to determine the unspecific binding. EGF (molar excess of approx. 200:1) and cetuximab (molar excess of 500:1) were used in the same way, but to investigate if the polypeptide binders have the same binding site as EGF and cetuximab. The cells were then washed 6 times with serum free Ham's F-10 medium and detached by adding 0.5 ml Trypsin-EDTA and incubated at 37° C. for 30 min or until the cells were detached. 1 ml of Ham's F-10 complete medium was added and the cells were re-suspended. In some wells a 0.5 ml suspension was used to count the cells. The radioactivity (1.5 ml and 1 ml, respectively, for the cells that were counted) was measured with a gamma counter.

Figure 7:
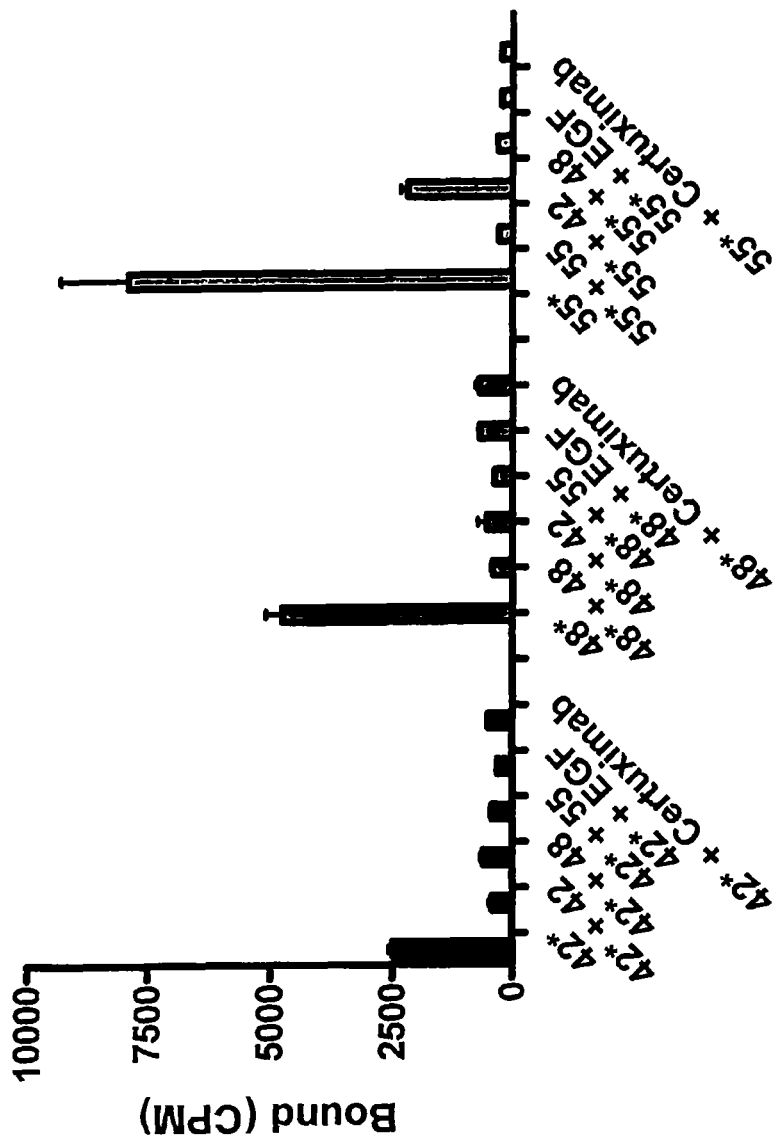
FIG. 7 is a diagram showing the result of cellular binding studies with radio-labeled EGFR-binding polypeptides according to the invention.

The results are presented in FIG. 7. Specifically, in FIG. 7, cellular binding of [$^{125}$I] $(Z00942)_2$ (42*), [$^{125}$I]$(Z00948)_2$ (48*) and [$^{125}$I]$(Z00955)_2$ (55*) is shown. The data support the unexpected results from the previous FACS-ranking of the binders which indicate that $Z_{EFGR:955}$ seem to be the best binder of native EFGR on cells, followed by $Z_{EGFR:948}$ and $Z_{EGFR:942}$ in spite of the fact that $(Z_{EGFR:942})_2$ displayed the highest affinity in the BIAcore analysis. In addition, the three EFGR-binding polypeptide constructs seem to bind overlapping epitopes. Furthermore, they seem to all compete for the same binding site as the natural ligand EFG and the monoclonal antibody cetuximab.

Saturation Assay

To determine the affinity constant, the saturation of polypeptide binder binding was determined. The EGFR-rich cell line A431 was cultured in 24-well plates. Cells were kept on ice and washed once in cold serum free Ham's F-10 medium. A dilution series of the $^{125}$I labeled-polypeptide dimeric binders was prepared and added to the cells with a molar excess of approximately 10:1. The cells were incubated for 4 hours, during slow movement, on ice in an environment where air from an incubator was trapped within a plastic bag together with the cell plate. For every concentration there was also a blocked control containing unlabeled polypeptide binders with a molar excess of approximately 300:1 for estimation of unspecific binding. The cells were then washed 6 times in cold Ham's F10 serum free medium and the cells were detached by adding 0.5 ml Trypsin-EDTA and incubated in 37° C. for 30 min or until the cells were detached. 1 ml of Ham's F-10 complete medium was added and the cells were re-suspended. In some wells 0.5 ml suspension was used to count the cells. The radioactivity was measured with a gamma counter. The data was analyzed by GraphPad Prism 4.

Figure 8A:
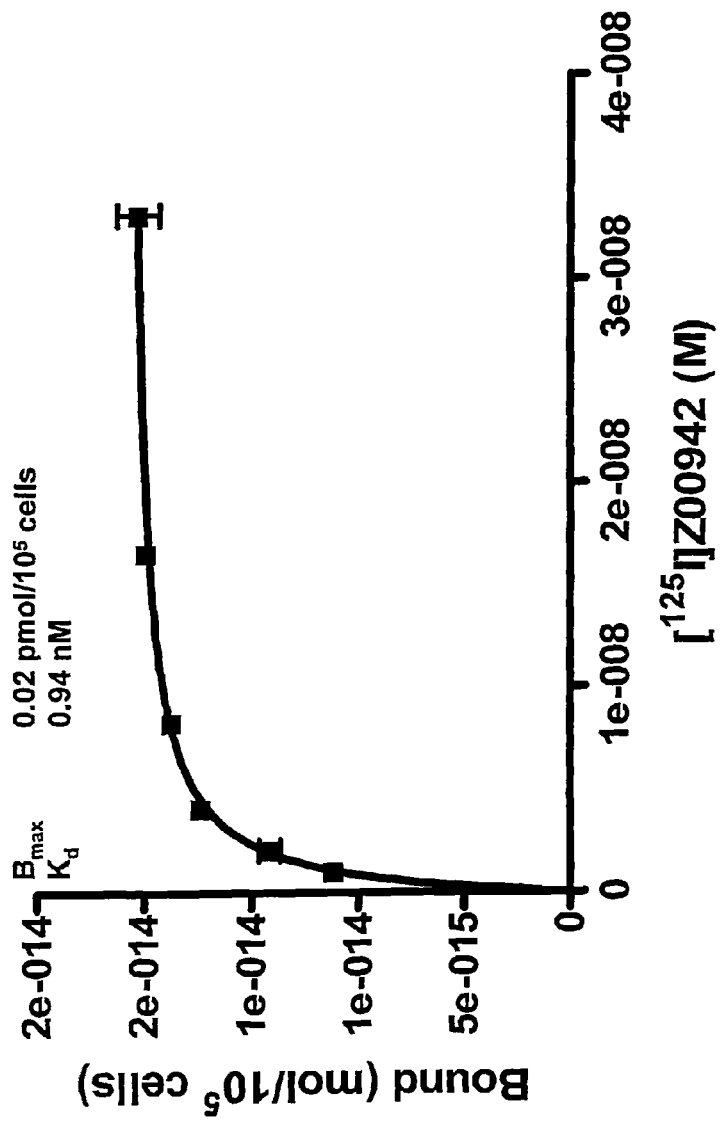
FIG. 8 is a series of graphs showing the results of saturation and studies with radio-labeled EGFR-binding polypeptides according to the invention.
Figure 8B:
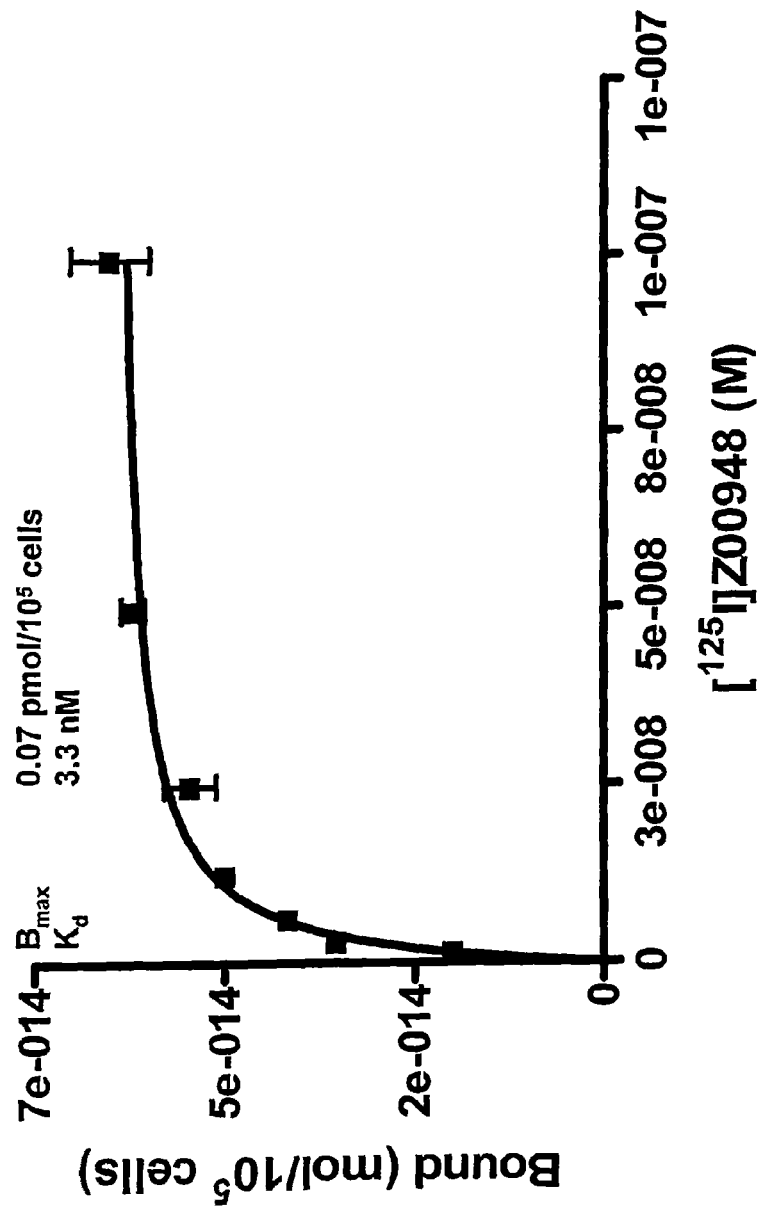
Figure 8C:
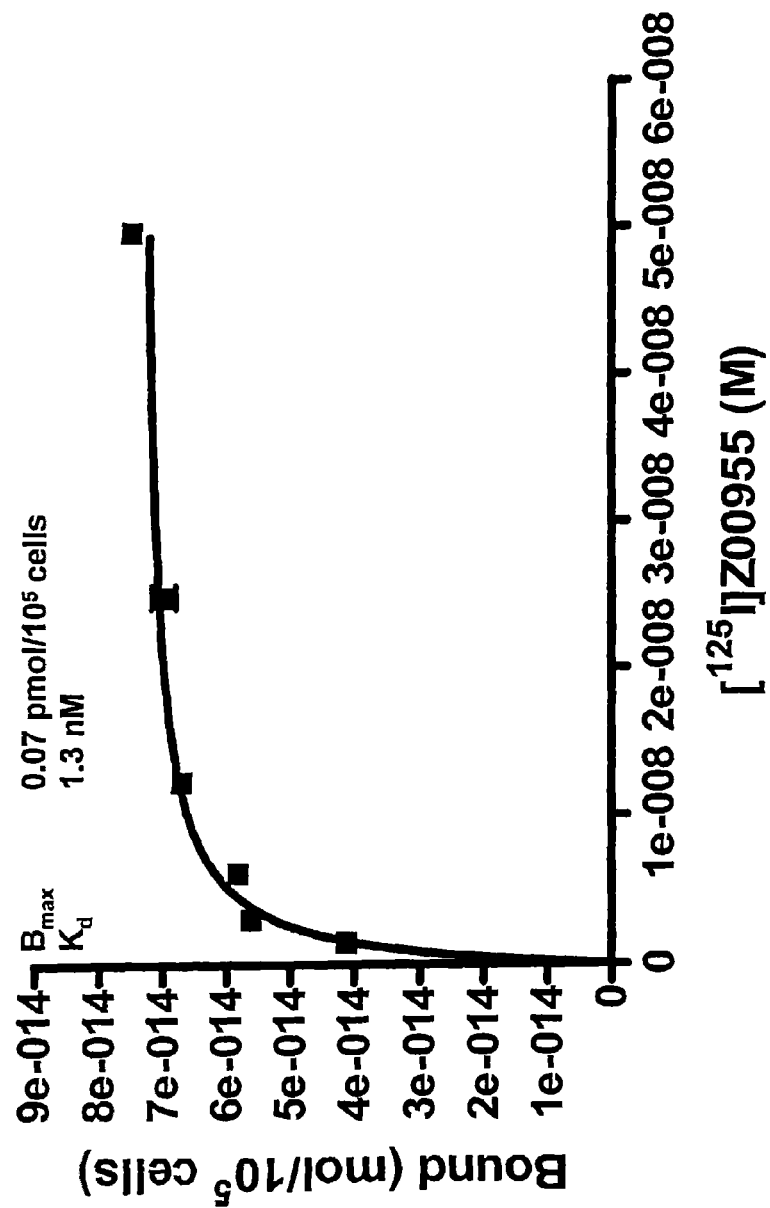

The results are shown in FIG. 8. Specifically, in FIG. 8, the results of saturation studies of [$^{125}$I]Z00942 (A), [$^{125}$I]Z00948(B) and [$^{125}$I]Z00955 (C) are shown. Mean values and standard deviations from three values are shown.

Example 2

Second Selection of EGFR-Binding Polypeptides According to the Invention

Materials and Methods

Strains and Vectors

The amber suppressor *Escherichia coli* strain RRIΔM15 (Rüther, U. (1982) *Nucleic Acids Res.* 10, 5765-72) was used for library construction, as bacterial host for phage production and for the cloning procedure. The phagemid vector pAffi1 was used for library construction and is described elsewhere (Grönwall C, Jonsson A, Lindström S, Gunneriusson E, Ståhl S, Herne N: "Selection and characterization of Affibody ligands binding to Alzheimer amyloid beta peptides", J. Biotechnol. (2006) in press, Epub 27 Sep. 2006). Phagemid inserts of selected clones were subcloned into the expression vectors pAY442, containing a T7 promoter (Studier et al., (1990) *Methods Enzymol.* 185, 60-89), a DNA fragment encoding a hexahistidyl ($His_6$) tag and a multiple cloning site, together with a gene conferring resistance to kanamycin. The *E. coli* strain BL21(DE3) (Novagen, Madison, Wis.) was used for protein production from the expression vectors.

Construction of a Secondary Phagemid Library

A strategy for affinity maturation was decided based upon the alignment of four sequences from the first selection of EGFR-binding molecules (Example 1, FIG. 2). The secondary library was created by PCR amplification from a single 129-nucleotide template oligonucleotide with certain degenerated codons (5' ctc gag gta gac aac aaa ttc aac aaa gaa nnk nnk nnk gcg nnk nnk gag atc mry mry tta cct aac tta aac ggt tgg caa atg acc gcc ttc atc gcg agt tta kyt gat gaa cca agc caa agc) 3°, encoding helices 1 and 2 of protein Z. The gene fragment was amplified using the forward primer 5'-cccccccccc ctcgaggtagacaacaaattcaa-3' (XhoI site underlined) and the reverse primer 5'-cccccct gctagcaagttagcgctttggcttgggtcatc-3° (NheI site underlined), with 1 pmol template oligonucleotide for each of 95 parallel reactions. The amplification was done using AmpliTaq Gold polymerase (Applied Biosystems, Foster City, Calif.) for 15 cycles (15 seconds at 96° C., 15 seconds at 60° C., and 1 minute at 72° C.), pooled, purified using QIAquick PCR purification kit (Qiagen, Hilden, Germany), XhoI/NheI digested and ligated to XhoI/NheI digested phagemid vector pAffi1 encoding the third nonvariegated α helix of protein Z. The ligated library vector was fenol:chloroform:isoamyl alcohol (25:24:21 v/v) (Invitrogen) extracted. Electrocompetent Escherichia coli RRIΔM15 cells were transformed with 30 aliquots of ligated material using 0.2-cm gap size cuvettes in an ECM 630 set (BTX, Genetronics) at 2500 V, 125Ω and 50 μF. Cells were grown in SOC medium (tryptone soy broth (TSB)+yeast extract (YE) supplemented with 1% glucose, 10 mmol/l $MgCl_2$, 10 mmol/l $MgSO_4$, 10 mmol/l NaCl and 2.5 mmol/l KCl) for ~1 h at 37° C. and transferred to six Erlenmeyer flasks, each containing 1 l of TSB supplemented with 2% glucose and 25 μg/ml carbenicillin and grown overnight at 37° C. The cells were centrifugated at 6000 g (15 min, 4° C.), following resuspension in PBS/glycerol solution to a final approximate concentration of 20% glycerol, aliquoted and stored at −80° C.

Phage Selection Procedures

A ~100 kDa recombinant extracellular domain of EGFR (denoted EGFR-ECD) was used as target protein during selections (1095-ER; R&D Systems). The EGFR-ECD was biotinylated in vitro using EZ-Link™-Sulfo-NHS-LC-LC-Biotin (Pierce, Rockford, Ill., USA). A 20-fold molar excess of biotin was added to EGFR-ECD in phosphate-buffered saline (PBS; 10 mM phosphate, 137 mM NaCl, pH 7.2), and the mixture was incubated at room temperature (RT) for 1 h followed by extensive dialysis against PBS over night (ON) at 4° C. to remove the surplus of biotin.

Preparation of phage stocks from the library and between selections was performed according to previously described procedures (Nord, K et al., (1997) Nat. Biotechnol., 15, 772-777; Hansson et al., (1999) Immunotechnology, 4, 237-252) using the helper phage M13K07 (New England Biolabs, Beverly, Mass., USA). PEG/NaCl precipitation yielded phage titers of about $10^{13}$ plaque forming units (pfu) per ml. The selection was performed in solution and the bound phages were captured on streptavidin-coated paramagnetic beads (Dynabeads M-280 Streptavidin; Dynal, Oslo, Norway). To avoid unspecific binders all tubes were pretreated with PBST (0.1% Tween-20 in PBS) supplemented with 5% bovine serum albumin (PBST-5% BSA). To further avoid binders against the streptavidin present on the streptavidin-coated paramagnetic beads ~1 ml of the phage stock in PBST-3% BSA was pre-incubated (30 min, end-over-end rotation) with 0.2 mg of the beads for the first two rounds of selection.

Four rounds of biopanning starting at target concentrations of 100 nM were performed as follows. In round 1, an aliquot of the library containing approximately $10^{12}$ pfu was incubated in 1 ml of 100 nM of biotinylated EGFR-ECD in PBST-3% BSA for 1 h at RT with continuous rotation, followed by −72 h at 4° C. For round 2, 50 nM and for round 3, 1 nM of biotinylated EGFR-ECD in 1 ml PBST-3% BSA, respectively, was incubated (1 h, RT, continuous end-over-end rotation) with a portion of the phage stock from previous round. The bound phages were captured by incubation with streptavidin-coated M-280 Dynabeads for 15 min (RT, continuous end-over-end rotation). The amount of beads was added allowing an immobilization of ~2 μg of the target protein per mg of beads, as previously determined by SDS-PAGE analysis (data not shown). For round 4, six slightly different selection protocols were performed, as detailed below in Table 2. In protocol 4-A and 4-B, 0.01 nM and 0.1 nM of biotinylated EGFR-ECD, respectively, was incubated for 2 h at RT with a portion of the phage stock from previous round, followed by incubation with a 100-fold excess of EGFR-ECD for 1 h at RT, capturing of bound phages by incubation with streptavidin-coated beads for 15 min, washing 18 times, incubation with a 100-fold excess of the first generation EGFR-binders 200942, 200948 and Z00955 (Example 1) for 1 h at RT, and finally washed twice. In protocol 4-C, 0.5 nM of biotinylated EGFR-ECD was incubated for 2 h at RT with a portion of the phage stock from previous round, followed by capturing of bound phages by incubation with streptavidin-coated beads for 15 min, washing 18 times, incubation with a 100-fold excess of first generation EGFR-binders for 1 h at RT, and finally washed twice. In protocol 4-D and 4-E, 0.1 and 0.5 nM of biotinylated EGFR-ECD, respectively, was incubated for 2 h at 37° C. with a portion of the phage stock from previous round, followed by incubation with a 100-fold excess of EGFR-ECD for 1 h at 37° C., capturing of bound phages by incubation with streptavidin-coated beads for 15 min, washing 18 times, incubation with a 100-fold excess of first generation EGFR-binders for 1 h at 37° C., and finally washed twice. In protocol 4-F, 0.1 nM of biotinylated EGFR-ECD was incubated for 2 h at RT with a portion of the phage stock from previous round, followed by capturing of bound phages by incubation with streptavidin-coated beads for 15 min and 20 washes. The number of washing steps was kept constant at 20 washes during the selection procedure and was performed in PBST-3% BSA in all washing steps except for the last wash where PBST was used. The phages were eluted with 500 μl of 50 mM glycine-HCl (pH 2.1) for 10 min, followed by immediate neutralization by adding 50 μl of 1 M Tris-HCl, pH 8.0 and 450 μl PBS. The eluted phages were used to infect log phase RRIΔM15 cells for 30 min at 37° C. The infected cell suspensions were spread on TYE agar plates (15 g/l agar, 3 g/l NaCl, 10 g/l tryptone and 5 g/l yeast extract), supplemented with 2% glucose and 100 mg/l ampicillin, and incubated over night at 37° C. The grown colonies were collected by resuspension in tryptic soy broth (TSB, 30 g/l; Merck, Darmstadt, Germany), supplemented with 5 g/l yeast extract, 2% glucose and 100 mg/l ampicillin, and a fraction (~500 times excess of cells compared to the phage titer after elution) was used for inoculation, leading to the next generation of phage stock. Phagemid particles were rescued from infected cells using helper phage M13K07, purified and concentrated with PEG precipitation. The selection process was monitored by titrating the phage stocks before each selection and after elution. A serial dilution of phages was allowed to infect log phase RRIΔM15 cells for 5 min at RT, followed by plating on TYE agar plates, supplemented with 2% glucose and 100 mg/l ampicillin, and ON incubation at 37° C.

TABLE 2

Protocols for Round 4 of selection

| | 4-A | 4-B | 4-C | 4-D | 4-E | 4-F |
|---|---|---|---|---|---|---|
| Incubation with bio-EGFR | 2 h, RT | 2 h, RT | 2 h, RT | 2 h, 37° C. | 2 h, 37° C. | 2 h, RT |
| Incubation with EGFR (100-fold excess) | 1 h, RT | 1 h, RT | — | 1 h, 37° C. | 1 h, 37° C. | — |
| Capturing of bound phages on streptavidin-coated beads | 15 min | 15 min | 15 min | 15 min | 15 min | 15 min |
| Wash | 1-18 | 1-18 | 1-18 | 1-18 | 1-18 | 1-20 |

TABLE 2-continued

Protocols for Round 4 of selection

|  | 4-A | 4-B | 4-C | 4-D | 4-E | 4-F |
|---|---|---|---|---|---|---|
| Incubation with first generation binders (100-fold excess) | 1 h, RT | 1 h, RT | 1 h, RT | 1 h, 37° C. | 1 h, 37° C. | — |
| Wash | 19-20 | 19-20 | 19-20 | 19-20 | 19-20 | — |

ELISA-Based Ranking of Second Generation Binders

Single colonies were inoculated in 1 ml TSB-YE medium supplemented with 100 μmol/l isopropyl-L-thio-β-D-galactopyranoside (IPTG) and 100 μg/ml ampicillin in deep well plates (Nunc, Roskilde, Denmark), and grown over night at 37° C. Cells were pelleted by centrifugation at 3000 g for 10 minutes. The pellets were resuspended in 300 μl PBST and frozen over night at −80° C. The samples were thawed and centrifuged at 3500 g for 20 minutes. The supernatants (100 μl), containing ABD-tagged Z variant molecules were loaded in microtiter wells, which had been previously coated with 6 μg/ml HSA (A-3782; Sigma) in 15 mmol/l $Na_2CO_3$ and 35 mmol/l $NaHCO_3$ (pH 9.6) ON at 4° C. and blocked with 2% skimmed milk powder in PBST for 1 h at RT (continuous shaking). The plates were washed four times with PBST prior to the addition of 50 μl of 8.4 μg/ml biotinylated EGFR-ECD per well and incubated for 1.5 h. After washing the wells four times with PBST, 50 μl of streptavidin-horseradish peroxidase (1:5000, DAKO Cytomation, Denmark) per well was added and incubated for 1 h. The wells were washed four times and 50 μl developing solution ImmunoPure TMB substrate kit (Pierce) was added to each well. After 30 min, 100 μl stop solution (2 M $H_2SO_4$) was added to each well. The absorbance at 450 nm was measured with a Tecan Sunrise spectrophotometer.

DNA Sequencing and Sequence Clustering

DNA sequencing of phagemid (pAffi1) inserts was performed on 187 EGFR-binding clones from the fourth round of panning. Specific primers and Big Dye terminator (Amersham Biosciences, Uppsala, Sweden) was used and the Sanger fragments analyzed on a DNA sequencer ABI PRISM® 3100 Genetic Analyzer (Applied Biosystems, Foster City, Calif., USA). Subcloned DNA fragments were verified by the same procedure. The sequences of the EGFR-binding polypeptides were clustered using the so-called average-link hierarchical clustering method described in more detail by Orlova et al. (*Cancer Res.* 66, 4339-48 (2006)).

The deduced amino acid sequences of candidate polypeptides exhibiting binding to EGFR in the ELISA screen described in the previous section are examples of EGFR-binding polypeptides according to the invention. They are presented in FIG. 1 and in the sequence listing as SEQ ID NO:174-309. The sequences of the corresponding EGFR-binding motif of each such binding polypeptide are presented in FIG. 1 and in the sequence listing as SEQ ID NO:11-146.

Screening of EGFR-Binding Polypeptides with Biacore

The cell supernatants containing ABD-tagged Z variants produced from the phage pAffi-vector prepared for ELISA was also subjected to a biosensor analysis. Supernatants from 54 clones demonstrating good binding from the ELISA were analyzed with real-time biospecific interaction on a Biacore® 2000 instrument. The target protein EGFR-ECD (diluted in 10 mM NaAc, pH 4.5) was immobilized (~1200 RU) on the carboxylated dextran layer of one flow-cell surface of a CM5 sensor chip (Biacore) by amine coupling, according to the manufacturer's instructions. Another flow-cell surface was activated and deactivated to be used as a reference surface and HSA was immobilized on a separate flow-cell surface on the CM5 sensor chip, to serve as a control of the amount of ABD-tagged Z variant that was expressed. A first generation EGFR-binder, $(Z00955)_2$ of Example 1, was also run as a control.

DNA Constructs

DNA fragments encoding different variants of second generation EGFR-binding Z variants ($Z_{EGFR}$) were subcloned into the expression vectors pAY442. The fragments were amplified from the pAffi1 vector with specific primers introducing an AccI overhang both 3' and 5', and ligated into the pAY442 vector, previously restricted with the same enzyme and dephosphorylated using calf intestine alkaline phosphatase (CIAP; Fermentas, Ontario, Canada). The amplified DNA fragments were purified with QIAquick PCR Purification Kit (Qiagen GmbH, Hilden, Germany) and hybridized prior to ligation with T4 DNA Ligase (New England Biolabs, Ipswich, Mass., USA). The ligations resulted in expression vectors encoding, under the control of the T7 promoter, the different Z variants fused to an N-terminus $His_6$ tag, allowing purification by immobilized metal ion affinity chromatography (IMAC). Dimer constructs of the EGFR-binding Z variants from both vectors were constructed, where a second Z variant gene fragment was introduced head-to-tail, giving rise to $His_6$-$(Z_{EGFR})_2$ variants. All plasmid preparations were, after cultivation of transformed *E. coli* cells overnight, performed using QIAprep Spin Miniprep Kit (Qiagen GmbH) according to manufacturer's instructions.

Protein Expression and Purification

Selected EGFR-binding Z variants were expressed as $His_6$-tagged fusion proteins from the pAY442 plasmid in *E. coli* strain BL21(DE3). Cells were inoculated in 25 ml of TSB medium (30 g/l Tryptic Soy Broth) supplemented with 5 g/l yeast (TSB+YE) and 50 mg/l kanamycin and grown at 37° C. in shake flasks. Fresh TSB+YE containing 50 mg/l kanamycin was inoculated with preculture to $OD_{600}$ ~0.06 and grown 3 h at 37° C. in a batch fermentor, when gene expression was induced by addition of isopropyl-L-thio-β-D-galactopyranoside (IPTG; Apollo Scientific Ltd, Bradbury, UK) to a final concentration of 0.5 mM. After 5 h cultivation the cells were harvested by centrifugation (15000 g, 20 min). The cell pellets were frozen over night, thawed and resuspended in denaturing buffer (7 M urea, 100 mM $NaH_2PO_4$, 10 mM Tris-HCl, pH 8.0). After incubation at RT for 30 min the cells were centrifuged at 25000 g for 15 min and the denatured protein from the supernatant was diluted in denaturing buffer (7 M urea, 100 mM $NaH_2PO_4$, 10 mM Tris-HCl, pH 6.3) and applied to a Ni-NTA Superflow Column (Qiagen). The bound protein was eluted with urea buffer (8 M urea, 100 mM $NaH_2PO_4$, 10 mM Tris-HCl, pH 4.5). The proteins were applied to a PD-10 column (GE Healthcare) and eluted with PBS (pH 7.4). The monomeric proteins are hereafter referred to as $Z_{EGFR:no}$ (pAY442 vector) and the dimeric proteins referred to as $(Z_{EGFR:no})_2$ (pAY442 vector). Protein concentrations were calculated from absorbance measurements at 280 nm, using the appropriate extinction coefficient for each protein. To confirm the purity and correct molecular mass of the protein they were run on a SDS-PAGE gel (NuPAGE 4-12% Bis-Tris Gel; Invitrogen), and on HPLC-MS (HPLC-MS 1100; Agilent Technologies). The purified proteins were further analyzed by CD, where CD spectra of 16 EGFR-binding Z variants were recorded using a Jasco-810 spectropolarimeter. All constructs were diluted with PBS to a final concentration of 0.5 mg/ml and 200 μl of each sample was placed in a 1 mm cuvette and scanned from 195 to 250 nm at 20° C. The thermal stability was examined by applying a temperature gradient from 20 to 90° C. at a fixed wavelength of 220 nm. The melting point, defined as the temperature at which 50% of the protein is unfolded, was interpreted from thermal unfolding spectra. Protein concentrations for selected $Z_{EGFR}$ variants were also determined by amino acid analysis (Aminosyraanalyscentralen, Uppsala, Sweden).

Biosensor Analyses

A Biacore® 2000 instrument (Biacore AB, Uppsala, Sweden) was used for real-time biospecific interaction analysis (BIA) between selected Z variants and the target protein. EGFR-ECD (diluted in 10 mM NaAc, pH 4.5) was immobilized (2400 RU) on the carboxylated dextran layer of one flow-cell surface of a CM5 sensor chip (Biacore) by amine coupling, according to the manufacturer's instructions. Another flow-cell surface was activated and deactivated to be used as a reference surface and HER2-ECD (Horak et al, (2005) Cancer Biother Radiopharm. 20, 603-13) (kindly supplied by Greg Adams, Fox Chase Cancer Center, PA) and ErbB3/Fc (R&D Systems, 348-RB) were immobilized on separate flow-cell surfaces on the CM5 sensor chip, to serve as negative controls. All Z variant samples were diluted in the running buffer HBS (10 mM HEPES, 150 mM NaCl, 3.4 mM EDTA, 0.005% surfactant P20, pH 7.4) before binding analysis was performed at 25° C.

In a first experiment, 500 nM of each Z variant (diluted in HBS) was injected over all surfaces with a flow rate of 30 μl/min. A first generation EGFR-binding molecule $((Z_{EGFR:955})_2$; Example 1) was also injected as a control. After each injection the flow cells were regenerated by the injection of 10 μl of 10 mM HCl.

In a second experiment, five selected monomeric $Z_{EGFR}$ variants were more subjected to kinetic analysis, in which the proteins were injected over an EGFR-ECD surface at concentrations ranging from 6.25 nM to 500 nM with a flow rate of 50 μl/min. The dissociation equilibrium constant ($K_D$), the association rate constant ($k_a$), and the dissociation rate constant ($k_d$) were calculated using BIAevaluation 3.2 software (Biacore). The samples were run in duplicates and after each injection the flow cells were regenerated by the injection of 10 μl of 10 mM HCl.

Immunofluorescence Staining

The cell line A431, obtained from European collection of cell cultures (www.ecacc.org.uk), was grown at 37° C. in 5% $CO_2$ environment in medium suggested by the provider. Media contained Fetal bovine serum (FBS) at concentrations suggested by the cell line providers (from Sigma-Aldrich). Sub-confluent cells were washed once with PBS, detached with a Trypsin/EDTA solution (Cambrex), and were resuspended in complete growth medium. Approximately 10000 cells in 20 μl were added per well of an 8 well, multi-well slide (Histolab) and were incubated over-night. On the following morning the cells were fixed with freshly prepared 3% formaldehyde in PBS for 15 minutes and washed twice with PBS. The cells were stained with 20 μl/well of the Z variants $His_6$-Z01859, $His_6$-Z01865, $His_6$-Z01864, $His_6$-Z01877, $His_6$-Z01868, $His_6$-Z01913, $His_6$-Z01836, $His_6$-$(Z01907)_2$-Cys and $His_6$-$(Z01953)_2$-Cys (2-10 μg/ml) for one hour, or with 1 μg/ml mouse anti-EGFR antibody (Abcam, no. ab30). Slides stained with Z variants were washed in PBS, incubated with goat antibody against Z (prepared in house) mixed with 5 μg/ml anti-goat IgG Alexa Fluor 488 (Molecular Probes) for one hour. The slide stained with antibody was washed in PBS and incubated with goat anti-mouse IgG-Alexa Fluor 488 (Molecular Probes) for one hour. After this second incubation step, the slides were washed again with PBS. The antibody slide was counterstained with 20 μl DAPI (Molecular Probes) at a concentration of 1 μg/ml for 10-20 seconds and washed again. All slides were dried and mounted with anti-fading reagent (Vector Laboratories) and membrane fluorescence was analyzed using a DM-LA microscope, equipped with a Leica DC camera (Leica Microsystems). Images were acquired using the IM1000 software (Leica Microsystems).

Immunohistochemical Staining

A431 xenograft tissues were obtained from biodistribution studies described below. The tumors were snap-frozen in liquid nitrogen and 6 μm thick cryosections were made using a Ljung CM3000 automated cryostat (Leica Microsystems). The sections were fixed with freshly prepared 3% formaldehyde in PBS for 15 minutes and washes twice with PBS. The sections were stained with $His_6$-$(Z01864)_2$-Cys or $His_6$-Z01877 at a concentration of 5 μg/ml, with $His_6$-$(Z01907)_2$-HRP or $His_6$-$(Z01853)_2$-HRP at a dilution of 1/40, approximately 6 μg/ml, for 1 hour. $His_6$-$(Z01864)_2$-Cys and $His_6$-Z01877 were detected with goat antibody against Z (prepared in-house) followed by 5 μg/ml rabbit anti-goat HRP. As a positive control, one slide was stained with 3 μg/ml anti EGFR antibody (Abcam, no. ab2430), washed and detected with rabbit Envision HRP (Dako, no. K4002) The HRP stained sample was washed once with PBS followed by incubation with DAB chromogen substrate (Dako Cytomation) for 7 minutes, followed by washes with PBS and counterstaining with Mayers HTX (Histolab) for 20 seconds. Slides were mounted with Mount-quick (Histolab). The slides were analyzed in a DMLA microscope, equipped with a Leica DC camera (Leica Microsystems). Images were acquired and saved using the IM1000 software (Leica Microsystems).

Binding Specificity and Biodistribution of $^{111}$In-Labeled EGFR-Binding Z Variants Radioactivity Measurements Radioactivity was measured using an automated gamma-counter with 3-inch NaI(T1) detector (1480 WIZARD, Wallac Oy, Turku, Finland). Distribution of radioactivity along ITLC strips was measured on the Cyclone™ Storage Phosphor System and analyzed using the OptiQuant™ image analysis software.

Coupling of p-SCN-benzyl-DTPA to Z Variants and Labeling of Conjugates with $^{111}$In Conjugation of isothiocyanate-benzyl-DTPA to $Z_{EGFR}$ variants was performed according to the method described by Mirzadeh et al. (Bioconjug Chem. 1990; 1:59-65), using a chelator-to-protein molar ratio of 1:1. Briefly, 300 μl of Z variant solution in PBS was mixed with 43 μl of freshly prepared solution (1 mg/ml) of isothiocyanate-benzyl-DTPA in 0.07 M sodium borate buffer, pH 9.2. The total volume was adjusted to 500 μl with 0.07 M borate buffer (pH 8.5-9.0), after which the mixture was vortexed for about 30 s and then incubated overnight at 37° C. After incubation, the reaction mixture was purified on a NAP-5 size exclusion column, pre-equilibrated with 0.2 M acetate buffer, pH 5.3 according to the manufacturer's instructions (high molecular weight fraction was 0.9 ml). The eluate was vortexed, whereafter the fraction containing 50 μg of Z variant conjugate was taken for further labeling and the rests of the solutions were frozen.

For labeling, 50 μg conjugate was mixed with a pre-determined amount of $^{111}$In (18 MBq) and incubated at room temperature for 60 minutes. To benzyl-DTPA-Z01908 conjugate, 37 μl of acetate buffer was added, to balance a high concentration of this Z variant.

For quality control of the labeling, ITLC eluted with 0.2 M citric acid was used. In this system, radiolabeled Z variants remain at the origin, free indium migrates with the front of solvent, and isothiocyanate-DTPA complex has a $R_f$ of 0.4.

Labeled conjugates were purified on NAP-5 columns (high molecular fraction was 0.9 ml), and products were checked for purity on ITLC.

Binding Specificity of $^{111}$In-Labeled Conjugates to EGFR-Expressing A431 Cells Labeled conjugates were added to two groups of Petri dishes (3 dishes per group) with a calculated ratio of one labeled conjugate per one EGFR receptor ($1.5 \times 10^6$ receptors per A431 cell). One group of dishes was pre-saturated with a 100-fold excess of non-labeled Z variant 10 min before the labeled conjugate was added. Cells were incubated for 1 hour at 37° C. and incubation medium was collected. Cell dishes were washed 6 times with cold serum-free medium and treated with 0.5 ml trypsin-EDTA for 10 min at 37° C. When cells were detached, 0.5 ml complete medium was added to every dish and cells were re-suspended. Cell suspension was collected for radioactivity measurements. Cell-associated radioactivity (C) was measured on an automated gamma-counter in parallel with 1 ml corresponding incubation medium (M). The fraction of added radioactivity bound to cells was calculated as % bound radioactivity=$C \times 100\%/(C+M)$.

Animal Tumor Models

The animal study was approved by the local Ethics Committee for Animal Research. Female outbred Balb/c nu/nu mice (10-12 weeks old at arrival) were used in the in vivo experiments. The animals were acclimatized for one week at the Rudbeck laboratory animal facility using standard diet, bedding and environment before tumor implantation. Mice had free access to food and drinking water. A431 tumors were grafted by subcutaneous (s.c.) injection of ~$10^7$ cells in the right hind leg. Xenografts were allowed to develop during 2 weeks.

Biodistribution Studies

Biodistribution of EGFR-binding polypeptides was evaluated in A431 tumor-bearing mice of the Balb/c (nu/nu) strain 4 h pi of indium-111 labeled EGFR Z variant conjugates (sc). Mice were anesthetized by an intraperitoneal injection of ketamine HCl (Ketalar, Pfizer) and xylazine HCl (Rompun; Bayer) mixture (20 µl of solution per gram of body weight; Ketalar-10 mg/ml, Rompun-1 mg/ml) 4 hours post-injection (pi) in all biodistribution experiments. Thereafter, the mice were euthanized through heart puncture with 1 ml syringe rinsed with diluted heparin (5000 IE/ml, from Leo Pharma, Copenhagen, Denmark). Organ samples of blood, lung, liver, spleen, colon, kidney, uterus, salivary glands, muscle, skin, bone, and tumor were collected, weighed and measured for radioactivity with a gamma-counter. Intestines (with content) were measured as whole organs and were not weighed. Organ uptake values were calculated as percent injected activity per gram tissue (% IA/g). In all experiments, the mice were randomly divided into groups with 4 animals in each group.

Results

Affinity Maturation of the First Generation EGFR-Binding Z Variants

An affinity maturation library based on a primary set of EGFR-binding molecules (Example 1) was designed and constructed. The sequences of the three best binders and a fourth sequence from further sequences analysis in Example 1 were aligned. It was considered reasonable to fix 5 positions (24, 25, 27, 28, and 32), and allow a certain bias for N and R in position 17 and 18 and for S and V in position 35 (FIG. 2D). Thus, positions 9, 10, 11, 13, and 14 were targeted for randomization using NNG/T degenerated codons (FIG. 2D). Due to the small size of protein Z, it was possible to use a single 129 nucleotide oligonucleotide with degenerated codons, encoding helices 1 and 2 of the Z-domain, to create a secondary library. The oligonucleotide was PCR-amplified and subsequently ligated into a phagemid vector encoding the third α-helix of protein Z. The resulting library consisted of ~$1 \times 10^9$ members, which should well include a majority of the theoretical variants. Phage stocks were prepared and selections performed essentially as previously described, using decreasing concentrations of target protein and intensive washing, as well as blocking of rebinding of binders with fast off-rate with an excess of non-biotinylated target protein and competition of first generation binders (Example 1) with second generation binders generated, to select for the strongest EGFR-binding variants in the library.

Clones obtained after four rounds of selection were cultivated in 96-well plates, freeze-thawed to release periplasmic content, and subjected to an ELISA screening procedure for EGFR-binding activity. When subjecting 372 randomly picked clones to the ELISA screening a majority of the clones demonstrated high absorbance values, indicating good binding to the target protein. From the clones with highest absorbance value, 186 clones were subjected to DNA sequencing and upon clustering of the sequenced clones the relationship between selected clones was visualized.

Additionally, a biosensor analysis screening was performed on periplasmic content containing ABD-tagged Z variants on 54 clones in order to select for clones with the best binding to EGFR and the slowest off-rate (data not shown).

Based on the values in the ELISA screening, the clustering results from the DNA sequencing and the biosensor analysis screening, 16 clones were selected for further characterization, namely 201836, Z01848, Z01853, Z01859, 201864, Z01865, 201868, Z01877, 201887, 201888, Z01905, Z01907, Z01908, Z01913, Z01917 and 201960 (see FIG. 1 and sequence listing). Virtually all binders were shown to be soluble at concentrations 21.0 mg/ml and showed a characteristic α-helix shaped CD spectrum in the far-UV spectral region (190-250 nm), with absorption maximum at 207 and 220 nm. The melting point was interpreted from thermal unfolding spectra and was determined to 50° C. or higher for virtually all binders. Spectra recorded after thermal denaturation showed a complete refolding into α-helix structure.

Biosensor Screening

To obtain an initial ranking of binding affinities, the 16 selected Z variants as well as the monomeric and dimeric $Z_{EGFR:955}$ (Example 1) were expressed and analyzed for their EGFR binding using a Biacore instrument. The different $Z_{EGFR}$ variants were separately injected over sensor chip flow-cell surfaces containing the immobilized target protein EGFR-ECD and control proteins HER2-ECD and Fc-fused HER3, respectively. Binding affinities in low nanomolar range was observed for all 16 binders (data not shown). Most binders did not show any unspecific binding to HER2-ECD and Fc-fused HER3. Five binders with the best affinity and off-range from biosensor analysis were selected for further characterization, namely Z01853, Z01868, Z01877, Z01907 and Z01908.

Comparing First and Second Generation Binders In Vitro

Figure 9A:
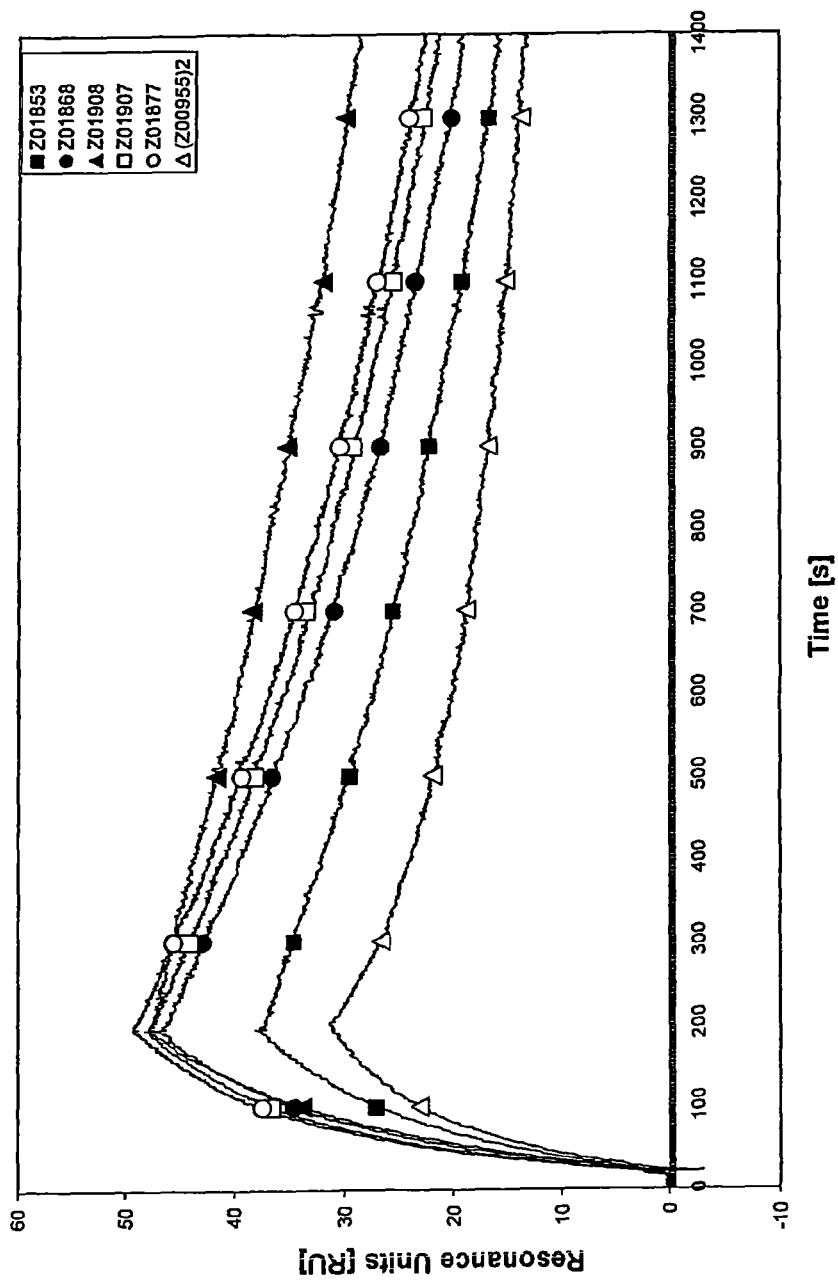
FIG. 9 shows the result of biosensor binding studies conducted using various EGFR-binding polypeptides according to the invention.
Figure 9B:
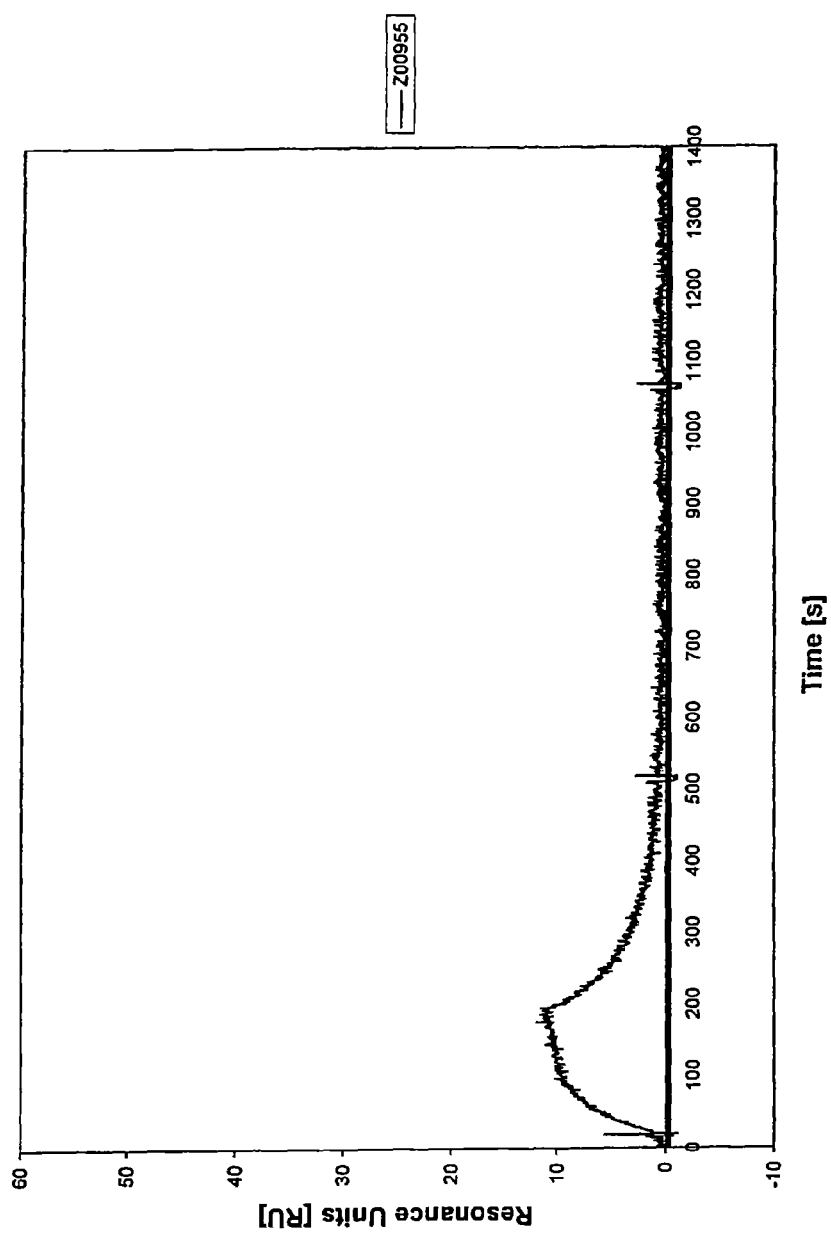

The affinity-matured 201853, Z01868, Z01877, 201907 and Z01908 ($K_D$~10 nM) were compared with a monomeric ($K_D$~185 nM) and dimeric ($K_D$~50 nM) form of Z00955 using Biacore analysis (FIG. 9). The association rate for the affinity matured Z variants are about the same as the monomeric and dimeric first generation binders. The dissociation rate, however, was improved-20-fold.

Fluorescense and Immunohistochemical Analysis

Figure 10A:
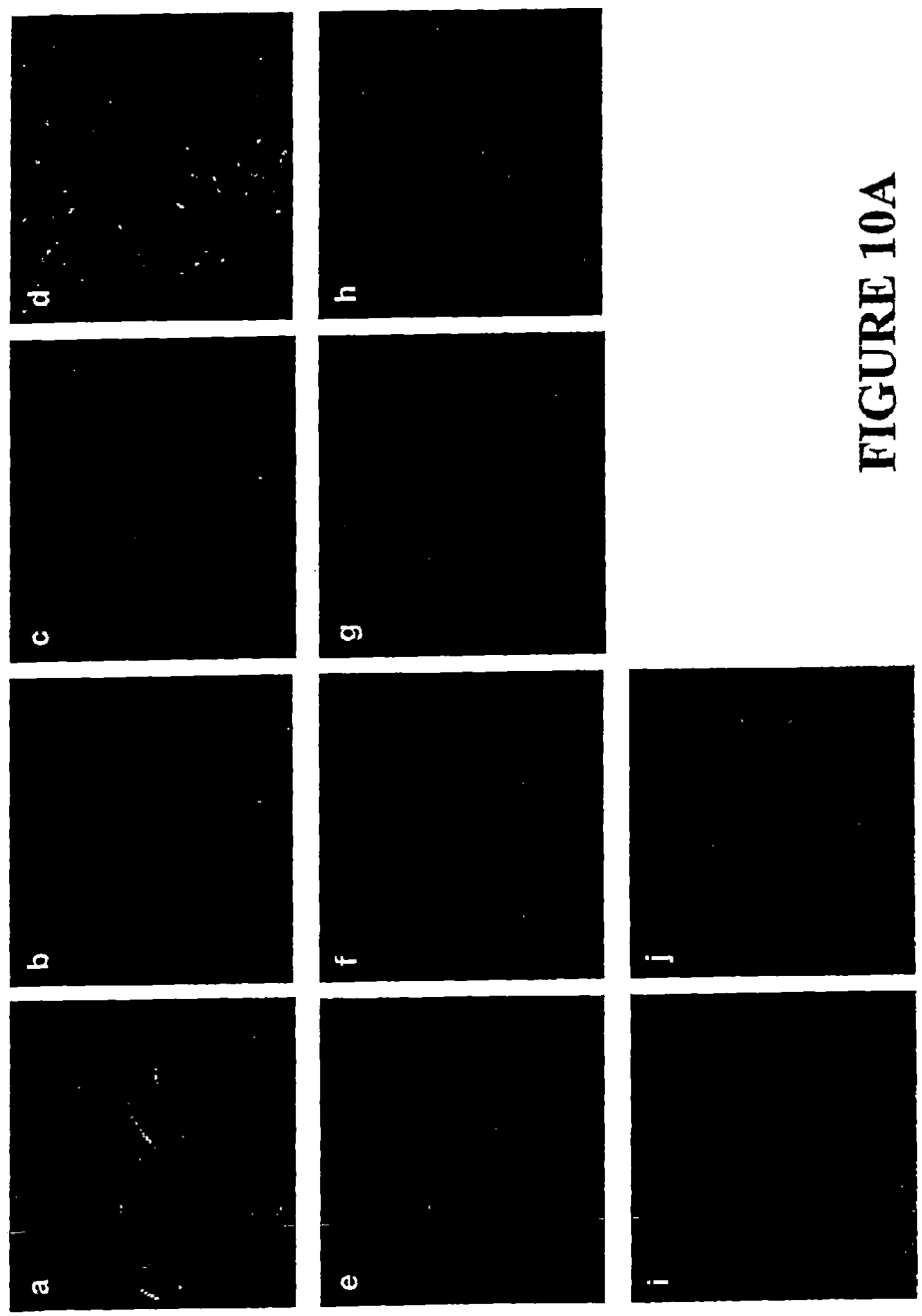
FIG. 10 is a series of images of cells exposed to EGFR-binding polypeptides according to the invention, using A) fluorescent detection and B) enzymatic detection.

The results are shown in FIG. 10. FIG. 10A shows A431 cells stained with the following Z variants specific for EGFR; a) $His_6$-Z01859, b) $His_6$-Z01865, c) $His_6$-Z01864, d) $His_6$-

Z01913, e) His$_6$-Z01877, f) His$_6$-Z01868, g) His$_6$-Z01836, h) His$_6$-(Z01853)$_2$-cys and i) His$_6$-(Z01907)$_2$-cys. The monomeric Z variants were detected with goat antibody against Z, followed by detection with Alexa 488 conjugated anti-goat antibodies. The dimeric Z variants were labeled with Oregon Green. As a positive control, A431 were stained with an anti-EGFR antibody (j).

Figure 10B:
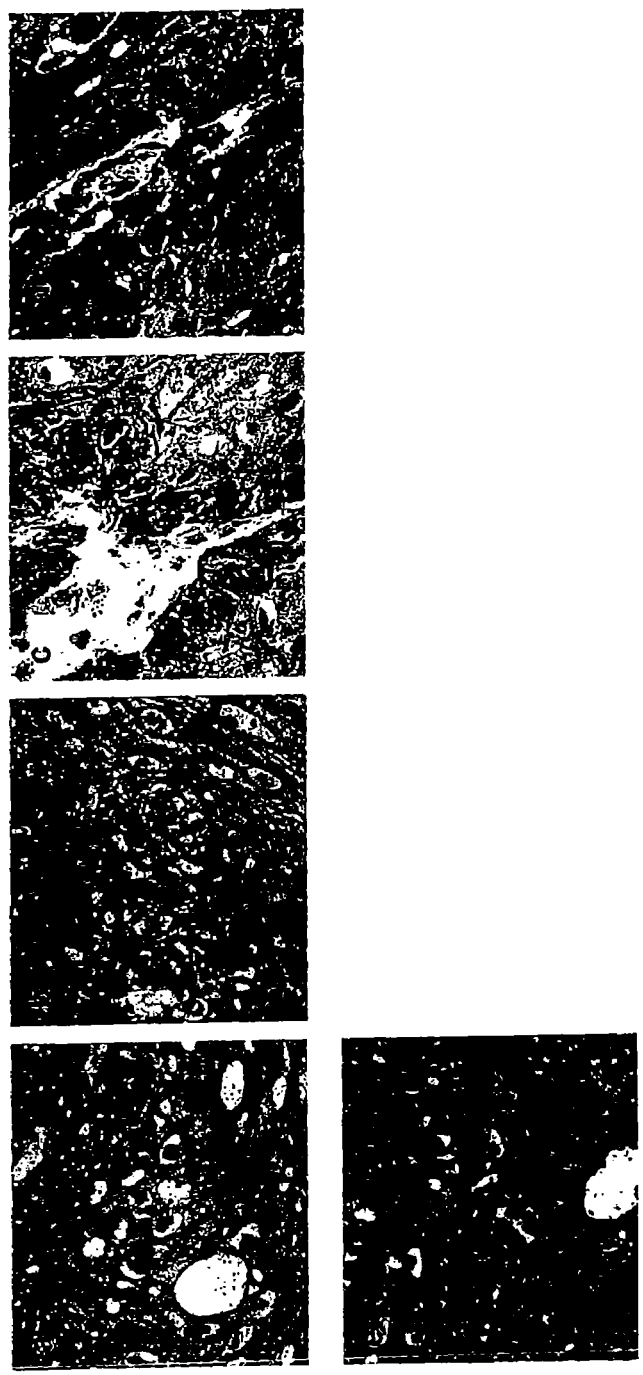

FIG. 10B shows cryosections of A431 xenografts stained with a) His$_6$-(Z01864)$_2$-Cys, b) His$_6$-Z01877, c) His$_6$-(Z01853)$_2$-Cys and d) His$_6$-(Z01907)$_2$-Cys. His$_6$-(Z01864)$_2$-Cys, and His$_6$-Z01877 (a and b) were detected with goat antibody against Z followed by detection with HRP conjugated anti-goat antibodies. The His$_6$-(Z01853)$_2$-Cys (c) and His$_6$-(Z01907)$_2$-Cys (d) molecules were directly conjugated to HPR. As a positive control, A431 were stained with an anti-EGFR antibody (e).

Specificity and Biodistribution of $^{111}$In-Labeled EGFR-Binding Z Variants

All Z variant conjugates were successfully labeled with indium-111 with labeling yields higher than 90%, and after NAP-5 purification, all conjugates had a purity of over 95%.

Figure 11:
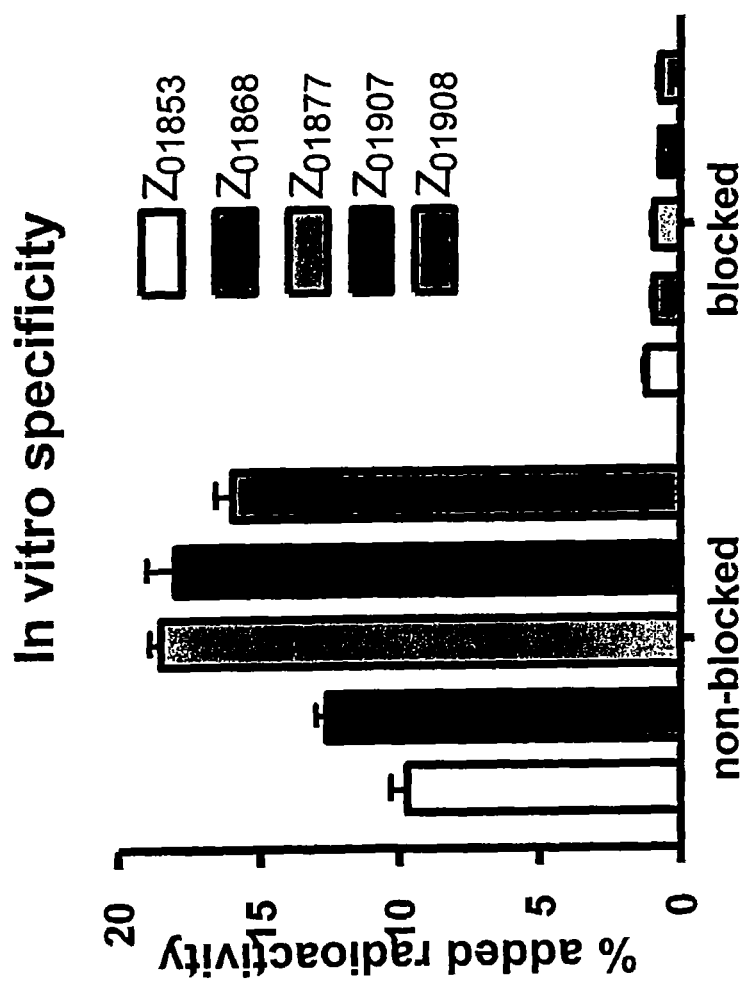
FIG. 11 is a diagram showing the results of an in vitro specificity test of indium-111 labeled benzyl-DTPA conjugates of EGFR-binding polypeptides according to the invention on A431 cells. All data points are mean values of three measurements, and error bars represent SEM.

The binding specificity of the labeled conjugates was evaluated in the EGFR expressing epidermoid carcinoma cell line A431. The results are shown in FIG. 11. In the figure, all data points are mean values of three measurements, and the error bars represent SEM. The binding of all conjugates was found to be EGFR-specific (see FIG. 11), since it was possible to block the uptake by addition of 100-fold excess of non-labeled $Z_{EGFR}$ (p<0.0001).

Figure 12:
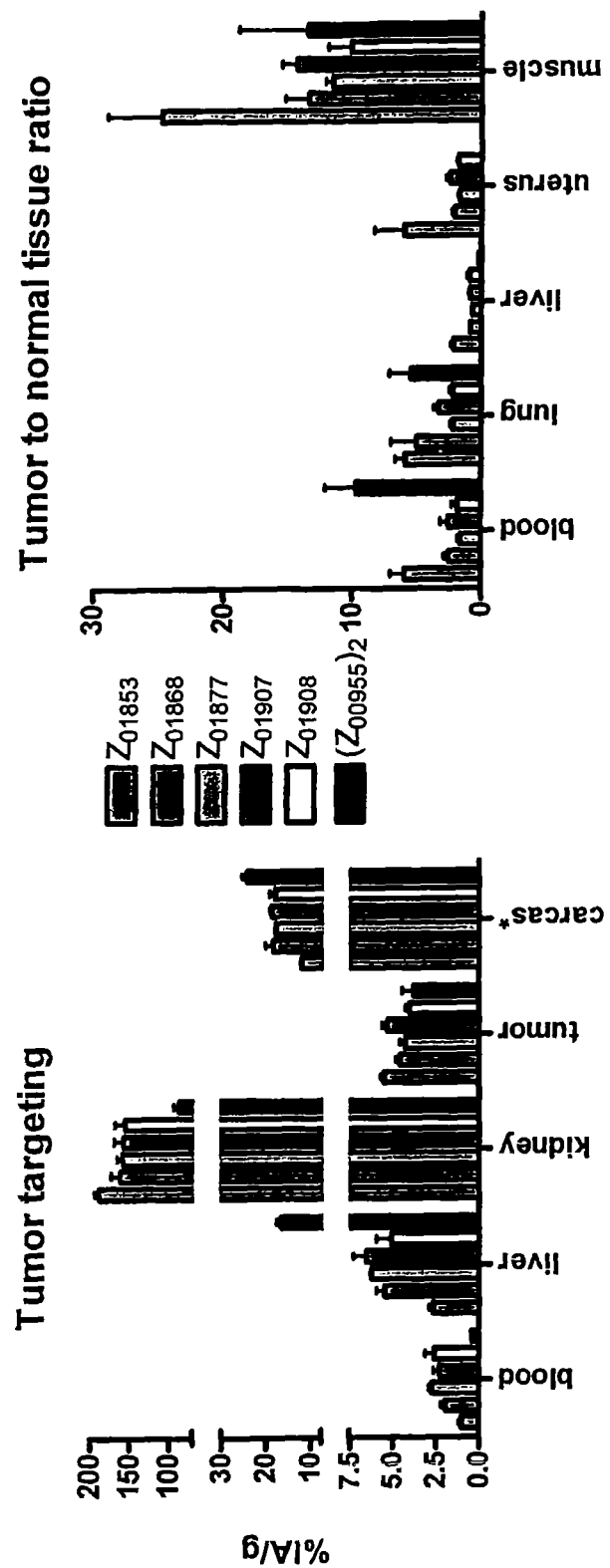
FIG. 12 is a series of diagrams showing biodistribution of $^{111}$In-benzyl-DTPA-EGFR binding conjugates and tumor to normal tissue ratios in mice bearing A431 xenografts. Each data point represents an average from four animals±standard deviation and is expressed as the percent of injected radioactivity per gram organ or tissue.

The biodistribution results for indium-111 labeled Z variant conjugates 4 h pi in A431 tumor bearing mice are summarized in FIG. 12. In the figure, each data point represents an average from four animals±standard deviation and is expressed as the percent of injected radioactivity per gram organ or tissue. Data for $^{111}$In-CHX-DTPA-($Z_{EGFR:955}$)$_2$ were obtained by Erika Nordberg (Biomedical radiation Sciences, Uppsala University) in collaboration with Affibody AB (VINNOVA) and included for comparison.

Tumor targeting in vivo was successful, with all five new Z variants on the level of 4-6% IA/g, but was not improved in comparison to non-maturated dimer (4% IA/g).

The main differences between the first-generation dimer (Z00955)$_2$ and all maturated monomers could be observed in the blood clearance, liver uptake and kidney accumulation: for the new monomers selected in the maturation experiment, the blood concentration of radioactivity was higher, the liver uptake was lower and the kidney uptake was higher than for (Z00955)$_2$. Most likely, these observations are related: the new monomers have a weaker binding to EGFR receptors in the liver, due to lower cross-reactivity to murine receptors and/or due to monovalent binding to the receptor, which does not trigger internalization and binding is reversible.

Example 3

Third Selection of EGFR-Binding Polypeptides According to the Invention

Based on a statistical analysis of the selection results from Example 2, a third library of putative EGFR binding polypeptides was prepared essentially as described above. Following phage display selection using EGFR as target and ELISA screening of the selected variants, 17 additional sequences of EGFR binding Z variants were identified. Their amino acid sequences are presented in FIG. 1 and in the sequence listing as SEQ ID NO:310-326. The deduced EGFR binding motifs of these EGFR binding Z variants are presented in FIG. 1 and in the sequence listing as SEQ ID NO:147-163.

The invention claimed is:

1. A method of treatment of an EGFR-related condition in a mammalian subject or in material derived from a mammalian subject, in which the subject or material is treated with an EGFR-binding polypeptide alone or in combination with a therapeutic agent, said polypeptide comprising an epidermal growth factor receptor binding motif, EBM, which motif consists of an amino acid sequence selected from:

i) $EX_2X_3X_4AX_6X_7EIR$ $X_{11}LPNLNGWQX_{20}TAFIX_{25}SLX_{28}D$, wherein, independently of each other, $X_2$ is selected from M, V, L, and I;

$X_3$ is selected from W, D, and E;

$X_4$ is selected from I, V, G, S, M, L, A, T, N, and D;

$X_6$ is selected from W, V, and I;

$X_7$ is selected from D, E, N, and K;

$X_{11}$ is selected from D, N, E, Y, and S;

$X_{20}$ is selected from M, L, and F;

$X_{25}$ is selected from A, S, and G; and $X_{28}$ is selected from L, V, and F; and ii) an amino acid sequence which has at least 85% identity to the sequence defined in i);
the EGFR-binding polypeptide binding to EGFR such that the KD value of the interaction is at most 10 μM;
wherein the EGFR-related condition is a cancer.

2. The method of treatment according to claim 1, in which binding of said EGFR-binding polypeptide or said combination to an EGFR of the subject, or in the material, inhibits or stimulates activation of the receptor.

3. The method of treatment according to claim 1, in which binding of the EGFR-binding polypeptide to an EGFR of the subject, or in the material, inhibits cell signaling.

4. The method of treatment according to claim 1, in which the cancer is selected from lung, breast, prostate, colon, ovary, head and neck cancers.

5. The method according to claim 1, in which said subject is human.

6. The method according to claim 1, wherein $X_2$ in said EBM is M.

7. The method according to claim 1, wherein $X_3$ in said EBM is W.

8. The method according to claim 1, wherein $X_4$ in said EBM is selected from I, V, G, and S.

9. The method according to claim 1, wherein $X_6$ in said EBM is selected from V and W.

10. The method according to claim 1, wherein $X_n$ in said EBM is selected from D, N, and E.

11. The method according to claim 1, wherein $X_{20}$ in said EBM is M.

12. The method according to claim 1, wherein $X_{25}$ in said EBM is selected from A and S.

13. The method according to claim 1, wherein $X_{28}$ in said EBM is L.

14. The method according to claim 1, wherein the amino acid sequence i) fulfils at least two of the following four conditions I, III, VII, and IX:
I) $X_2$ is M;
III) $X_6$ is W;
VII) $X_{20}$ is M;
IX) $X_{28}$ is L.

15. The method according to claim 14, wherein said amino acid sequence i) fulfils at least three of the four conditions I, III, VII, and IX.

16. The method according to claim 15, wherein the amino acid sequence i) is

EMWX$_4$AWX$_7$EIR X$_{11}$LPNLNGWQM TAFIX$_{25}$SLLD.

17. The method according to claim 1, wherein the amino acid sequence i) fulfils the following conditions:
VII) $X_{20}$ is M;
X) $X_{25}$ is A.

18. The method according to claim 1, wherein the amino acid sequence i) is selected from the group consisting of SEQ ID NOs: 48, 57, 87, 146-148, 150-153, and 156-161.

19. The method according to claim 18, wherein the amino acid sequence i) is selected from the group consisting of SEQ ID NO:48, SEQ ID NO:57, SEQ ID NO:87, and SEQ ID NO:147.

20. The method according to claim 1, wherein said EGFR-binding motif forms part of a three-helix bundle protein domain.

21. The method according to claim 20, wherein said EGFR-binding motif essentially forms part of two alpha helices and a loop connecting them, within said three-helix bundle protein domain.

22. The method according to claim 21, wherein said three-helix bundle protein domain is selected from domains of bacterial receptor proteins.

23. The method according to claim 22, wherein said three-helix bundle protein domain is selected from domains of protein A from *Staphylococcus aureus* or derivatives thereof.

24. The method according to claim 1, wherein said EGFR-binding polypeptide binds to EGFR such that the $K_D$ value of the interaction is at most $1 \times 10^{-6}$ M.

25. The method according to claim 24, wherein said EGFR-binding polypeptide binds to EGFR such that the $K_D$ value of the interaction is at most $1 \times 10^{-7}$ M.

26. The method according to claim 1, wherein said EGFR-binding polypeptide binds to the extra-cellular domain of EGFR.

27. The method according to claim 26, wherein said EGFR-binding polypeptide binds to a portion of the extra-cellular domain of EGFR corresponding to SEQ ID NO: 329.

28. The method according to claim 1, wherein said EGFR-binding polypeptide is present in multimeric form, comprising at least at least two EGFR-binding polypeptide monomer units, whose amino acid sequences may be the same or different.

29. The method according to claim 28, wherein said EGFR-binding polypeptide monomer units are covalently coupled together.

30. The method according to claim 29, wherein said EGFR-binding polypeptide monomer units are expressed as a fusion protein.

31. The method according to claim 28, wherein said EGFR-binding polypeptide is present in a dimeric form.

32. The method according to claim 1, wherein said EGFR-binding polypeptide is present in combination with a therapeutic agent.

33. The method according to claim 32, wherein said EGFR-binding polypeptide and therapeutic agent are covalently coupled together.

34. The method according to claim 32, wherein said EGFR-binding polypeptide and therapeutic agent are expressed as a fusion protein.

* * * * *